United States Patent [19]
Yoshimura et al.

[11] Patent Number: 5,612,356
[45] Date of Patent: Mar. 18, 1997

[54] HETEROCYCLE-CONTAINING CARBONIC ACID DERIVATIVES

[75] Inventors: Hiroyuki Yoshimura; Mitsuo Nagai; Shigeki Hibi; Koichi Kikuchi, all of Tsukuba; Ieharu Hishinuma, Kitasouma-gun; Junichi Nagakawa, Tsuchiura; Makoto Asada, Tsukuba; Norimasa Miyamoto, Tsukuba; Takayuki Hida, Tsukuba; Aichi Ogasawara, Tsukuba; Isao Yamatsu, Ushiku, all of Japan

[73] Assignee: Eisai Co., Ltd., Japan

[21] Appl. No.: 295,636

[22] PCT Filed: Dec. 20, 1993

[86] PCT No.: PCT/JP93/01841

§ 371 Date: Apr. 25, 1995

§ 102(e) Date: Apr. 25, 1995

[87] PCT Pub. No.: WO94/14777

PCT Pub. Date: Jul. 7, 1994

[30] Foreign Application Priority Data

Dec. 28, 1992 [JP] Japan .................................. 4-358616
Jan. 20, 1993 [JP] Japan .................................. 5-023450

[51] Int. Cl.$^6$ .................................................. A61K 31/415
[52] U.S. Cl. ........................ 514/338; 514/339; 514/406; 546/275.7; 546/276.7; 546/176; 546/159; 546/77; 548/358.5; 548/149; 548/242; 548/426; 548/181; 549/42; 549/457; 544/331; 544/372; 544/131; 544/140

[58] Field of Search ................... 548/358.5; 546/270, 546/271, 272; 514/338, 339, 406

[56] References Cited

U.S. PATENT DOCUMENTS

| | | | |
|---|---|---|---|
| 3,119,819 | 1/1964 | Robinson et al. | 546/41 |
| 4,874,747 | 10/1989 | Shroot et al. | 514/23 |
| 5,004,730 | 4/1991 | Philippe et al. | 514/29 |
| 5,061,705 | 10/1991 | Wuest et al. | 514/236.5 |
| 5,397,785 | 3/1995 | Ninomiya et al. | 514/291 |

FOREIGN PATENT DOCUMENTS 1071124 6/1967 United Kingdom.

*Primary Examiner*—Margaret W. Glass
*Attorney, Agent, or Firm*—Nixon & Vanderhye

[57] ABSTRACT

A heterocycle-containing carbonic acid derivative represented by the following general formula (I):

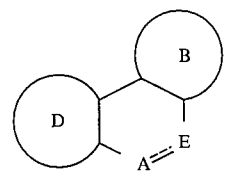

(I)

or a physiologically acceptable salt thereof which exhibits an excellent preventive and therapeutic effect against various diseases, and an intermediate which is useful for the production of the heterocycle-containing carbonic acid derivative.

7 Claims, No Drawings

HETEROCYCLE-CONTAINING CARBONIC ACID DERIVATIVES

BACKGROUND OF THE INVENTION

Field of the Invention

The present invention relates to heterocycle-containing carbonic acid derivatives and intermediates used for the production of the heterocycle-containing carbonic acid derivatives. More particularly, the present invention relates to novel heterocycle-containing carbonic acid derivatives which exhibit an excellent preventive or therapeutic effect against various diseases.

Description of the Related Art

Retinoic acid (vitamin A acid) is a substance essential for the growth and life-preservation of human beings and other mammals. It is known that this acid acts as a morphogenic factor in the ontogenesis and also variously acts on the differentiation and multiplication with respect to the adults. For example, it is known that the acid participates in cornification, formation of hair or function of sebaceous gland with respect to the epidermis; in the metabolism of bone and cartilage with respect to the connective tissue; in the regulation of immune function with respect to the immune system; in the differentiation of nerve cell with respect to the nervous system; in the differentiation and multiplication of blood cell with respect to the blood system; and in the secretion of thyroid and parathyroid hormones and the function thereof in target organs. Thus, retinoic acid is a substance which much participates in the mineral and basal metabolism. These various physiological activities of retinoic acid are exhibited by directly controlling the gene expression through a retinoid receptor family ($RAR_S$, $RXR_S$) present in the nucleus of a cell. With respect to retinoid acid, there have been known not only hypovitaminosis but also hypervitaminosis such as cornification disorder, alopecia and metabolic disorder of bone and cartilage. Further, it has recently been reported that the disorder of retinoid receptor is found in acute promyelocytic leukemia, squamous cell carcinoma of the head and neck, pulmonary carcinoma and so on, i.e., the disorder thereof participates in the sideration and evolution of these diseases. Under these circumstances, the development of a compound antagonistic to retinoids is believed to contribute to the elucidation of detailed mechanism of these various activities of retinoids and the investigation of clinical applicability thereof. Up to this time, TD-550, TD-560 and Ro41-5253 have been known as compounds antagonistic to retinoids [see Cell Biol. Rev., 25, 209 (1991), and Proc. Natl. Acad. Sci. USA., 89, 7129 (1992)]. However, these compounds are thought to be poor in the RARs-binding power and the antagonism against retinoids.

DISCLOSURE OF THE INVENTION

Summary of the Invention

In view of the above problem, the present inventors have extensively studied and have found that the heterocycle-containing carbonic acid derivatives which will be described below have an extremely high RARs-binding power and exhibit potent antagonism against retinoids. The present invention has been accomplished on the basis of this finding.

Thus, the present invention relates to a compound, i.e., a heterocycle-containing carbonic acid derivative, represented by the following general formula (I) or a physiologically acceptable salt thereof:

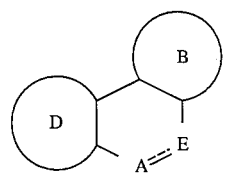

wherein
the ring D represents a group represented by the following formula:

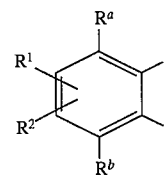

[wherein $R^1$ and $R^2$ may be the same or different from each other and each represents a hydrogen atom, a lower alkyl group, a lower alkoxy group, a cycloalkyloxy group which may have a substituent, a halogen atom, an aryl group which may have a substituent, an aryloxy group which may have a substituent or a heteroaryl group which may have a substituent, or alternatively $R^1$ and $R^2$ together form a 5- to 7-membered cycloalkyl ring which is substituted with one or more lower alkyl groups or a 5- to 7-membered saturated heterocycle containing S, O, SO, $SO_2$ or $NR^3$ (wherein $R^3$ represents a hydrogen atom or a lower alkyl group) as the hereto atom which is substituted with one or more lower alkyl groups; and $R^a$ and $R^b$ may be the same or different from each other and each represents a hydrogen atom, a lower alkyl group or a lower alkoxy group];

A represents O, S, $SO_2$, $NR^3$ ($R^3$ is as defined above) or $CR^4R^5$ (wherein $R^4$ and $R^5$ may be the same or different from each other and each represents a hydrogen atom or a lower alkyl group);

E represents $(CH_2)_n$ (wherein n is 0, 1 or 2), $CHCH_3$ or $C(CH_3)_2$;

the symbol "----" represents a single or double bond; and the ring B represents a group selected from the group consisting of the groups of the following formula:

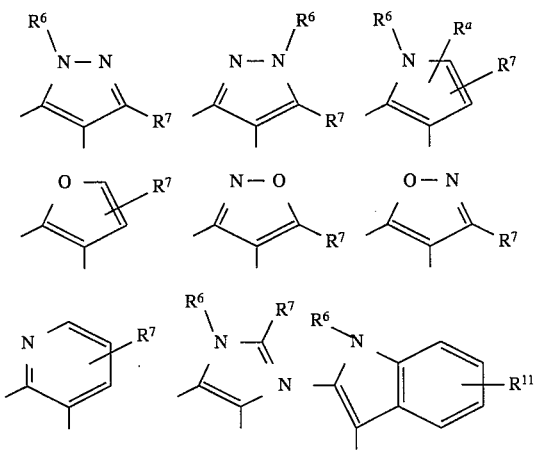

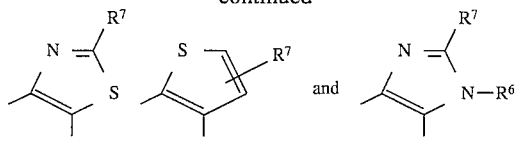 and

[wherein R⁶ represents a hydrogen atom, a lower alkyl group, an alkenylalkyl group, an alkynylalkyl group, a bridged cyclic hydrocarbon group, a cycloalkyl group which may have a substituent, a cycloalkylalkyl group which may have a substituent, a lower alkoxyalkyl group, an aryl group which may have a substituent, a heteroaryl group which may have a substituent, an arylalkyl group which may have a substituent or a heteroarylalkyl group which may have a substituent; R⁷ represents a group represented by the following formula:

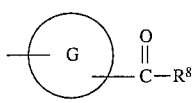

(wherein the ring G represents a phenylene group which may have a substituent or a 5- or 6-membered heterocyclic group having one or two hereto atom(s) which may have a substituent; and R⁸ represents a hydrogen atom, a hydroxyl group, a lower alkoxy group, a morpholylalkyloxy group or a group represented by the formula: —NR⁹R¹⁰ (wherein R⁹ and R¹⁰ may be the same or different from each other and each represents a hydrogen atom, a hydroxyl group, a lower alkyl group, a lower alkoxy group, a hydroxyalkyl group, an aryl group or a heteroaryl group, or alternatively R⁹ and R¹⁰ may form a ring, which may contain a nitrogen atom, an oxygen atom or a sulfur atom, together with the nitrogen atom to which R⁹ and R¹⁰ are bonded)), R^a is as defined above and R¹¹ represents a group represented by the formula: —COR⁸ (R⁸ is as defined above)].

The compounds and physiologically acceptable salts thereof described above include compounds represented by the following general formula (I-A) and physiologically acceptable salts thereof:

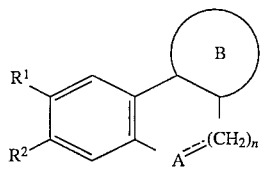

(I-A)

wherein R¹ and R² together form a 5- to 7-membered cycloalkyl ring which is substituted with one or more lower alkyl groups and which may contain S, O, SO, SO₂ or NR³ (wherein R³ represents a hydrogen atom or a lower alkyl group); A represents O, S, SO₂, NR³ or C(R⁴)R⁵ (wherein R⁴ and R⁵ may be the same or different from each other and each represensts a hydrogen atom or a lower alkyl group); n is 0, 1 or 2; the symbol "----" represents a single or double bond; and B represents an unsaturated 5- or 6-membered heterocyclic group which is substituted and contains one or two heteroatoms selected from the group consisting of N, O and S and which may be condensed with a substituted benzene ring to form a dicyclic heterocycle structure, while the heterocyclic group includes the following groups:

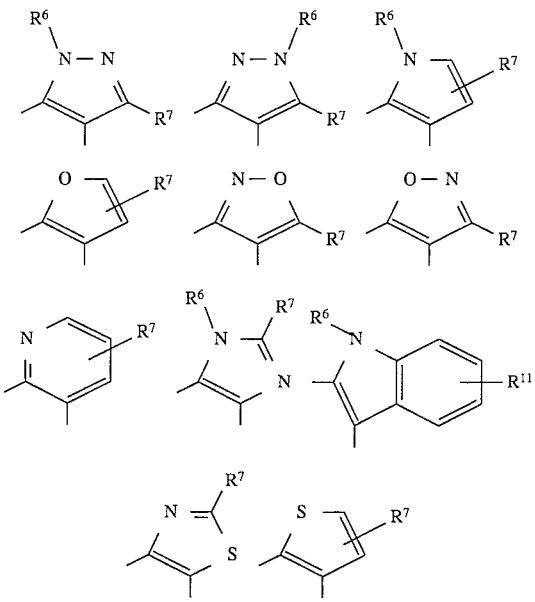

wherein R⁶ represents a hydrogen atom, a lower alkyl group, an alkenylalkyl group, an alkynylalkyl group, a cycloalkyl group, a cycloalkylalkyl group, a lower alkoxyalkyl group, an aryl group, a heteroaryl group, an arylalkyl group or a heteroarylalkyl group; R⁷ represents a group represented by the following general formula:

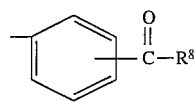

[wherein R⁸ represents a hydrogen atom, a hydroxyl group, a lower alkoxy group or a group represented by the general formula: —NR⁹R¹⁰ (wherein R⁹ and R¹⁰ may be the same or different from each other and each represents a hydrogen atom, a hydroxyl group, a lower alkyl group, a lower alkoxy group, a hydroxyalkyl group, an aryl group or a heteroaryl group, or alternatively R⁹ and R¹⁰ may form a ring, which may contain a nitrogen, oxygen or sulfur atom, together with the nitrogen atom to which R⁹ and R¹⁰ are bonded)], and R¹¹ represents a group represented by the general formula:

.

Some heterocycle-containing carbonic acid derivatives have been disclosed in, e.g., Japanese Patent Publication-A No. 240058/1990 as compounds which act as an agonist and which is improved in the prevention of side effects caused by the excess of retinolds. However, they are different from the compounds of the present invention in chemical structure and activities.

Further, the present inventors have found intermediates used for the production of the above-described carbonic acid derivatives.

Thus, the present invention relates to a compound, as an intermediate, represented by the following general formula (II) or a physiologically acceptable salt thereof:

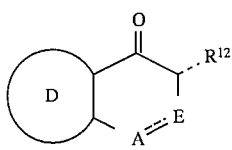

(II)

wherein
the ring D represents a group represented by the following formula:

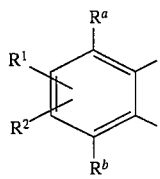

[wherein $R^1$ and $R^2$ may be the same or different from each other and each represents a hydrogen atom, a lower alkyl group, a lower alkoxy group, a cycloalkyloxy group which may have a substituent, a halogen atom, an aryl group which may have a substituent, an aryloxy group which may have a substituent or a heteroaryl group which may have a substituent, or alternatively $R^1$ and $R^2$ together form a 5- to 7-membered cycloalkyl ring which is substituted with one or more lower alkyl groups or a 5- to 7-membered saturated heterocycle containing S, O, SO, $SO_2$ or $NR^3$ (wherein $R^3$ represents a hydrogen atom or a lower alkyl group) as the hereto atom which is substituted with one or more lower alkyl groups; and $R^a$ and $R^b$ may be the same or different from each other and each represents a hydrogen atom, a lower alkyl group or a lower alkoxy group];

A represents O, S, $SO_2$, $NR^3$ ($R^3$ is as defined above) or $CR^4R^5$ (wherein $R^4$ and $R^5$ may be the same or different from each other and each represents a hydrogen atom or a lower alkyl group);

E represents $(CH_2)_n$ (wherein n is 0, 1 or 2), $CHCH_3$ or $C(CH_3)_2$;

the symbol "----" represents a single or double bond; and $R^{12}$ represents two hydrogen atoms, a group selected from the group consisting of groups represented by the following formulas:

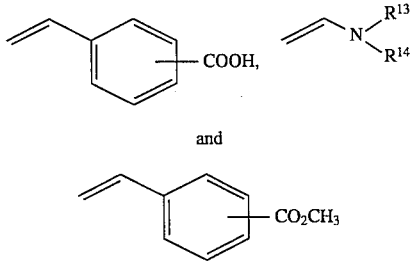

(wherein $R^{13}$ and $R^{14}$ may be the same or different from each other and each represents a hydrogen atom or a lower alkyl group), or a hydrogen atom and a group selected from the group consisting of groups represented by the following formulas:

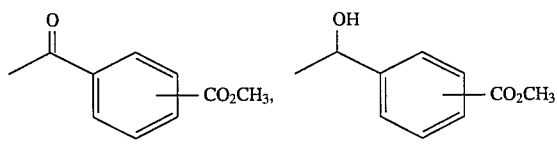

and

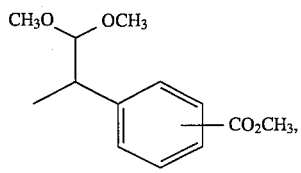

with the proviso that the symbol "----" represents two single bonds or a double bond.

The intermediates described above include compounds represented by the following formulas:

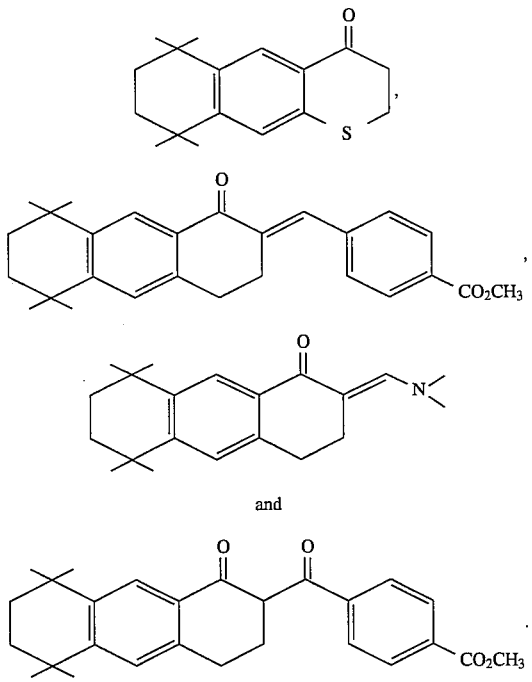

Furthermore, the present invention relates to (1) a therapeutic and preventive agent for disease for which antagonism against retinoids is efficacious, which comprises the compound represented by the above general formula (I) or the physiologically acceptable salt thereof as an active ingredient; (2) a pharmacological composition which comprises a therapeutically effective amount of the compound represented by the above general formula (I) or the physiologically acceptable salt thereof and a pharmacologically acceptable vehicle; (3) a use of the compound represented by the above general formula (I) or the physiologically acceptable salt thereof for making the medicament for treating a disease for which antagonism against retinoids is efficacious; and (4) a method for treating a disease which comprises administering a therapeutically effective amount of the compound represented by the above general formula (I) or the physiologically acceptable salt thereof to a patient suffering from a disease for which antagonism against retinoids is efficacious.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DISCLOSURE OF THE INVENTION

Detailed Description of the Invention

The present invention relates to heterocycle-containing carbonic acid derivatives represented by the above general formula (I) and physiologically acceptable salts thereof.

The lower alkyl group defined with respect to the Formula (I) is a linear or branched alkyl group having 1 to 6 carbon atoms, and examples thereof include a methyl group, an ethyl group, a propyl group, an isopropyl group, a butyl group, an isobutyl group, a sec-butyl group, a tert-butyl group, an amyl group, an isopentyl group and a neopentyl group. Among them, a methyl group, an ethyl group, a propyl group and an isopropyl group are preferable. The lower alkoxy group includes, for example, a methoxy group, an ethoxy group, a n-propoxy group, an isopropoxy group and a n-butoxy group.

The cycloalkyloxy group which may have a substituent, which is defined with respect to $R^1$ and $R^2$, is a cycloalkyl group having 3 to 7 carbon atoms which may have a substituent. Examples thereof include a cyclopropyloxy group, a cyclobutyloxy group, a cyclopentyloxy group, a cyclohexyloxy group and a cycloheptyloxy group, which may have a substituent.

The aryl group defined with respect to $R^9$ and $R^{10}$ is a phenyl group or a naphthyl group. The aryl group which may have a substituent, which is defined with respect to $R^1$, $R^2$ and $R^6$, is a phenyl group or a naphthyl group which may be substituted with a lower alkyl group such as a methyl group and an ethyl group, a halogen atom, a lower alkoxy group or the like.

The aryloxy group which may have a substituent, which is defined with respect to $R^1$ and $R^2$, is a phenyloxy group or a naphthyloxy group which may be substituted with a lower alkyl group such as a methyl group and an ethyl group, a halogen atom, a lower alkoxy group or the like.

The heteroaryl group defined with respect to $R^9$ and $R^{10}$ is one derived from a heterocycle and examples thereof include a pyridyl group, a thiazolyl group, a pyrimidyl group, a furyl group and a thienyl group. The heteroaryl group which may have a substituent, which is defined with respect to $R^1$, $R^2$ and $R^6$, is one derived from a heterocycle and may have a substituent on the heterocycle.

The cycloalkyl group which may have a substituent, which is defined with respect to $R^6$, is a cycloalkyl group having 3 to 7 carbon atoms such as a cyclopropyl group, a cyclobutyl group, a cyclopentyl group, a cyclohexyl group and a cycloheptyl group, which may have a substituent.

The cycloalkylalkyl group which may have a substituent, which is defined with respect to $R^6$, is a group derived from the above cycloalkyl group which may have a substituent, and representative examples thereof include a cyclopropylmethyl group, a cyclopentylmethyl group, a cyclohexylmethyl group and a cyclohexylethyl group.

The lower alkoxyalkyl group defined with respect to $R^6$ is a group derived from the above lower alkoxy group, and representative examples thereof include a methoxyethyl group, a methoxypropyl group and an ethoxyethyl group.

The arylalkyl group which may have a substituent, which is defined with respect to $R^6$, is one derived from the above aryl group which may have a substituent, and preferable examples thereof include a benzyl group and a phenethyl group.

The heteroarylalkyl group which may have a substituent, which is defined with respect to $R^6$, is one derived from the above heteroaryl group which may have a substituent, and examples thereof include a pyridylmethyl group and a pyridylethyl group.

The morpholylalkyloxy group defined with respect to $R^8$ includes, for example, a morpholylethyloxy group, a morpholylmethyloxy group and a morpholylpropyloxy group.

The hydroxyalkyl group defined with respect to $R^9$ and $R^{10}$ is the alkyl group described above wherein one to three hydroxyl group(s) is(are) substituted for the hydrogen atom.

The alkenylalkyl group defined with respect to $R^6$ comprises an alkylene group and at least one alkenyl group bonded to the carbon atom of the alkylene group.

The alkynylalkyl group defined with respect to $R^6$ comprises an alkylene group and at least one alkenyl group bonded to the carbon atom of the alkylene group.

In the definition with respect to $R^1$ and $R^2$, "$R^1$ and $R^2$ together form a 5- to 7-membered cycloalkyl which is substituted with one or more lower alkyl groups or a 5- to 7-membered saturated heterocycle containing S, O, SO, $SO_2$ or $NR^3$ ($R^3$ is as defined above) as the hetero atom which is substituted with one or more lower alkyl groups" means that the $R^1$ and $R^2$ together form, for example, those represented by the following formulas:

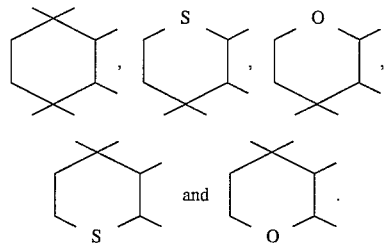

In the definition with respect to $R^9$ and $R^{10}$, "$R^9$ and $R^{10}$ may form a ring which may contain a nitrogen atom, an oxygen atom or a sulfur atom, together with the nitrogen atom to which $R^9$ and $R^{10}$ are bonded" means that the $R^9$ and $R^{10}$ together form, for example, those represented by the following formulas:

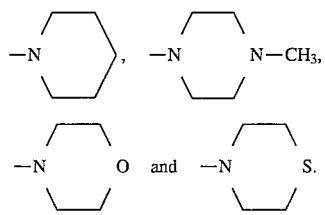

The phenylene group which may have a substituent defined with respect to $R^7$ includes a phenylene group wherein a lower alkyl group such as a methyl group and an ethyl group, a halogen atom or a lower alkoxy group may be substituted for the hydrogen atom constituting the phenylene group. The dihydric heterocyclic group which may have a substituent defined with respect to $R^7$ is a dihydric group derived from, for example, pyridine, furan, pyrimidine or pyradine, which may have a substituent.

The bridged cyclic hydrocarbon group defined with respect to $R^6$ includes, for example, an adamantyl group and an adamantylmethyl group.

The physiologically acceptable salt according to the present invention may be a conventional nontoxic one, and examples thereof include inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as argininate, aspartate and glutamate. Further, the compound of the present invention may form a metal salt such as sodium, potassium, calcium or magnesium salt. The physiologically acceptable salt of the present invention includes these metal salts.

The compound of the present invention described above includes those represented by the following formula:

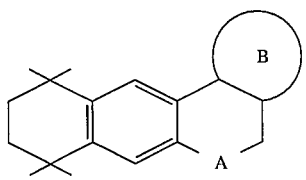

(wherein A and the ring B are as defined above).

Preferable examples of the compounds according to the present invention include those represented by the following formulas:

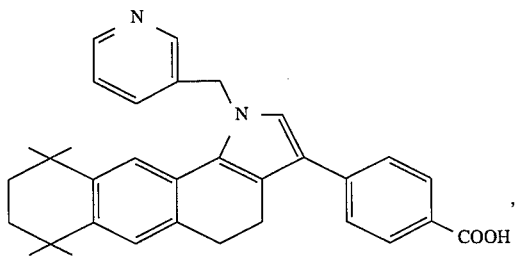

,

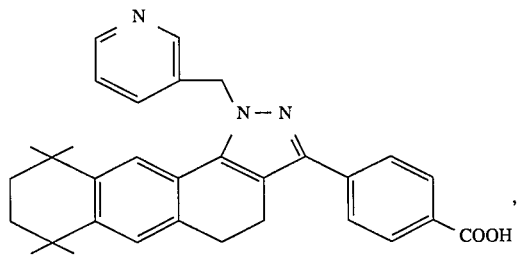

,

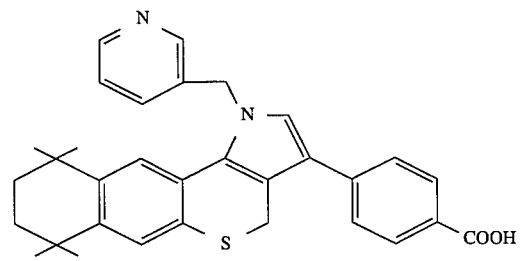

and

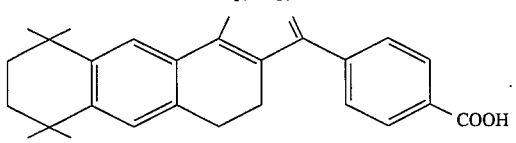

Representative processes for preparing the compound of the present invention will now be described.

[Preparation process 1]

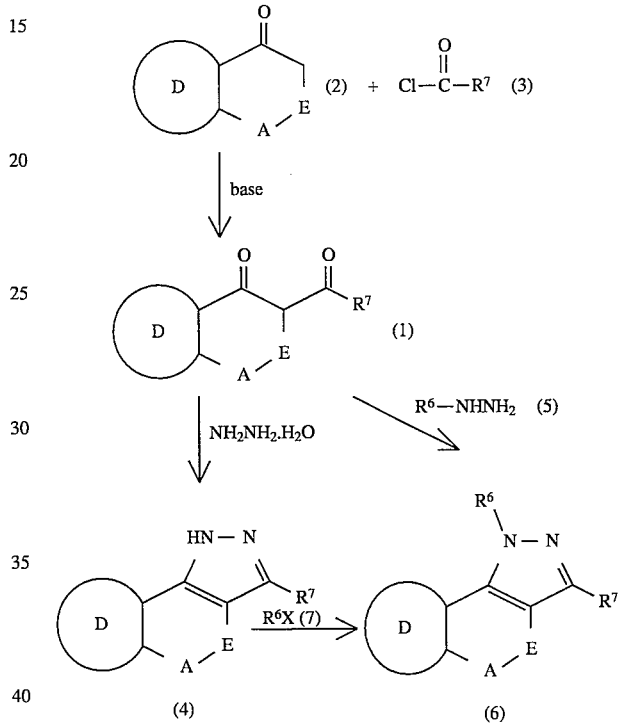

wherein the ring D, $R^6$, $R^7$, A and E are each as defined above; and X represents a halogen atom.

A diketone compound represented by the general formula (1) can be prepared by reacting a ketone compound (2) with an acid chloride (3) in the presence of a base. The use of lithium diisopropylamide or lithium bistrimethylsilylamide as the base gives good results. The solvent to be used in this reaction includes ethers such as diethyl ether, tetrahydrofuran and 1,2-dimethoxyethane. The reaction temperature may range from −78° C. to the boiling point of the solvent used, preferably −78° to +20° C.

Then, the diketone compound (1) is reacted with hydrazine hydrate to give a pyrazole compound represented by the general formula (4). Alternatively, the diketone compound (1) is reacted with a monosubstituted hydrazine (5) to give an isomer mixture containing a pyrazole compound represented by the general formula (6). The isomer mixture is subjected to crystallization or column chromatography to give a pyrazole compound represented by the general formula (6) which is freed from simultaneously formed undesirable isomers.

The above reaction may be accelerated by the addition of an acid (such as hydrochloric acid, sulfuric acid, acetic acid or polyphosphoric acid) which is used also as a dehydrating agent, though the reaction can proceed in the absence of any catalyst.

The solvent to be used in the above reaction may be any one which is unreactive with hydrazine. Examples of the solvent include alcohols such as methanol, ethanol and isopropanol; aromatic hydrocarbons such as benzene, toluene and xylene; aprotic solvents such as N,N-dimethylformamide and dimethyl sulfoxide; and chlorinated hydrocarbons such as dichloromethane, chloroform and 1,2-dichloroethane. Although the reaction temperature may range from 0° C. to the boiling point of the solvent used, it is preferably from room temperature to the boiling point of the solvent.

The pyrazole compound represented by the general formula (4) is reacted with a halide (7) represented by the formula: $R^6X$ in the presence of a base to give an isomer mixture containing a pyrazole compound represented by the general formula (6). The isomer mixture is subjected to crystallization or column chromatography to give a pyrazole compound represented by the general formula (6) which is freed from simultaneously formed undesirable isomers.

The base to be used in this reaction includes alkali metal compounds such as potassium carbonate, sodium hydride and potassium hydride; and alkali metal alkoxides such as sodium methoxide, sodium ethoxide and potassium t-butoxide. The solvent to be used therein includes N,N-dimethylformamide, tetrahydrofuran and 1,2-dimethoxyethane and the reaction temperature may range from 0° C. to the boiling point of the solvent used.

[Preparation process 2]

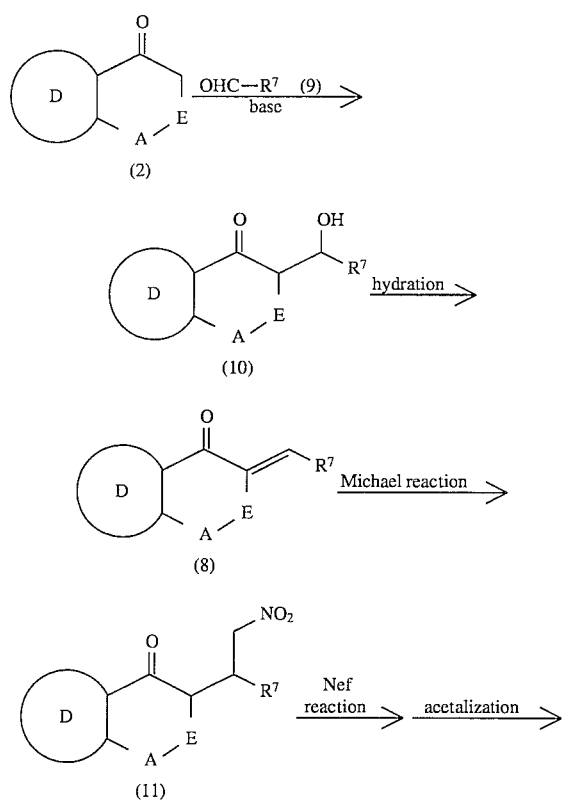

-continued
[Preparation process 2]

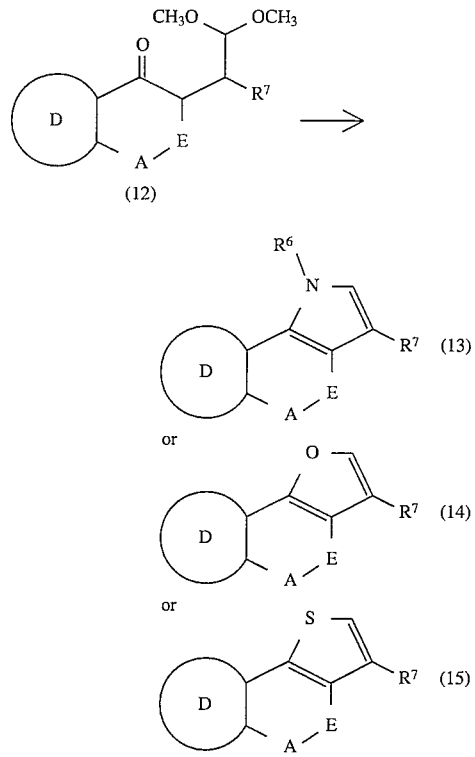

wherein the ring D, $R^6$, $R^7$, A and E are each as defined above.

A compound represented by the general formula (8) can be prepared by reacting a ketone compound represented by the general formula (2) with an aldehyde represented by the general formula (9) in the presence of a catalytic amount of a base to form an alcohol compound (10) and dehydrating this alcohol (10) in the presence of an acid.

The base to be used in the preparation of the alcohol compound (10) is preferably an alkali metal hydroxide such as sodium hydroxide or potassium hydroxide, while the solvent to be used therein includes methanol, ethanol, propanol, tetrahydrofuran and N,N-dimethylformamide. Although the reaction temperature may range from 0° C. to the boiling point of the solvent used, it is preferably 20° to 40° C.

The acid to be used in the above dehydration includes hydrochloric acid, sulfuric acid, p-toluenesulfonic acid, trifluoroacetic acid, oxalic acid and phosphoric acid, while the solvent to be used therein includes ethers such as diethyl ether, tetrahydrofuran, 1,4-dioxane and 1,2-dimethoxyethane; and aromatic hydrocarbons such as benzene, toluene and xylene. The above dehydration is conducted at a temperature ranging from 0° C. to the boiling point of the solvent used. Some compounds represented by the general formula (8) can be prepared directly from the compounds (2) without dehydration.

Then, the compound (8) is converted into a compound represented by the general formula (11) by treating it with a catalytic amount of a base in a nitomethane solvent (which may contain tetrahydrofuran, methanol or ethanol at need when the compound (8) is difficultly soluble therein). The base to be used in this reaction includes N-benzyltrimethylammonium hydroxide, triethylamine and diisopropylethylamine, while the reaction temperature is preferably from 0°

C. to room temperature, though it may range from 0° C. to the boiling point of the solvent used.

An acetal compound represented by the general formula (12) can be prepared by converting the compound (11) into a γ-keto aldehyde compound through the Nef reaction [see Chem. Rev., 55, 137 (1955)] and acetalizing this aldehyde. This acetalization is conducted by adding a mineral acid such as sulfuric acid or hydrochloric acid to methanol and adding the keto aldehyde to the obtained mixture. The reaction temperature is preferably −40° C. to room temperature, though it may range from −78° C. to the boiling point of the solvent used.

A pyrrole compound represented by the general formula (13) can be prepared by reacting the dimethyl acetal compound (12) with a primary amine represented by the general formula: $R^6$—$NH_2$.

The solvent to be used in this reaction may be any one which is inert to the reaction, and examples thereof include aromatic hydrocarbons such as benzene, toluene and xylene; ethers such as tetrahydrofuran and 1,2-dimethoxyethane; and alcohols such as methanol and ethanol. The above reaction is conducted in the presence of an acid. The acid to be used in the reaction is one which is used also as a dehydrating agent, and examples thereof include hydrochloric acid, sulfuric acid, glacial acetic acid and polyphosphoric acid.

Further, the dimethyl acetal (12) can be converted into a furan compound represented by the general formula (14) by treating it with an acid.

The acid to be used in this reaction includes sulfuric acid and polyphosphoric acid. This reaction is conducted at a temperature of 0° to 100° C. Furthermore, the dimethyl acetal (12) can also be converted into a thiophene compound represented by the general formula (15) by reacting it with a sulfide such as phosphorus pentasulfide or hydrogen sulfide. The solvent to be used includes aromatic hydrocarbons such as benzene, toluene and xylene; and pyridine, while the reaction temperature is preferably from 50° C. to the boiling point of the solvent used, though it may range from 0° C. to the boiling point of the solvent.

[Preparation process 3]

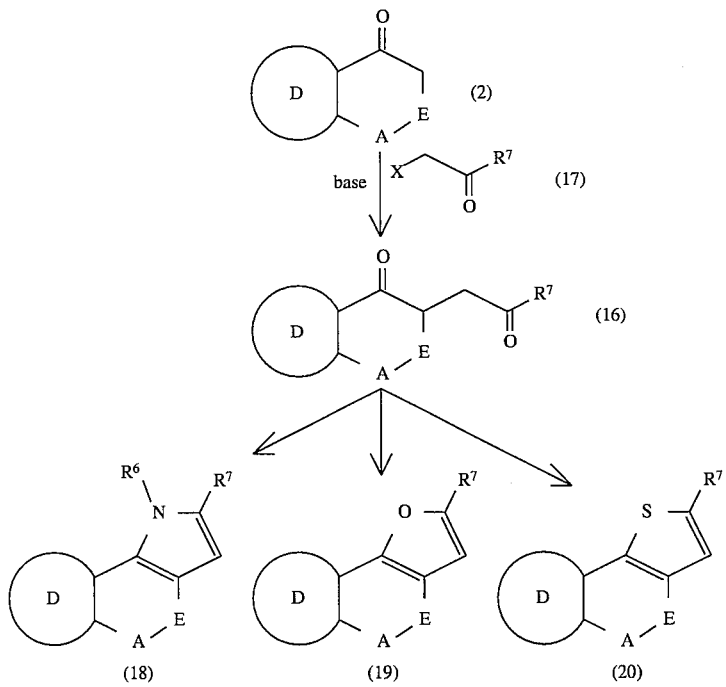

wherein the ring D, $R^6$, $R^7$, A and E are each as defined above; and X represents a halogen atom.

A γ-dikatone compound represented by the general formula (16) can be prepared by reacting a ketone compound (2) with a 2-haloacetophenone represented by the general formula (17) in the presence of a base. The use of lithium diisopropylamide or lithium bistrimethylsilylamide as the base gives good results. The solvent to be used in this reaction includes ethers such as diethyl ether, tetrahydrofuran and 1,2-dimethoxyethane. The reaction temperature is preferably −78° C. to room temperature, though it may range from −78° C. to the boiling point of the solvent used.

The γ-diketone compound (16) thus obtained can be converted into a pyrrole compound (18), a furan compound (19) and a thiophene compound (20) by the same processes as those employed in the Preparation process 2 for converting the compound (12) into the compounds (13), (14) and (15), respectively.

15

[Preparation process 4]

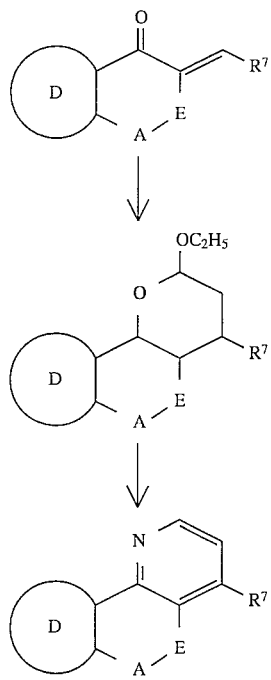

wherein the ring D, R⁷, A and E are each as defined above.

A pyridine derivative represented by the general formula (21) can be prepared from a compound represented by the general formula (8) according to the process described in J. Chem. Soc., Chem. Commun., 1230 (1988) and J. Am. Chem. Soc. USA., 113, 8016 (1991). Specifically, a dihydropyran compound represented by the general formula (22) can be prepared by dissolving a compound (8) in 1,2-dichloroethane and reacting the compound (8) with ethyl vinyl ether in the presence of a catalytic amount of a ytterbium complex; and the obtained dihydropyran compound can be converted into the objective compound by dissolving it in acetonitrile, adding hydroxylamine hydrochloride to the solution, and heating the obtained mixture under reflux.

[Preparation process 5]

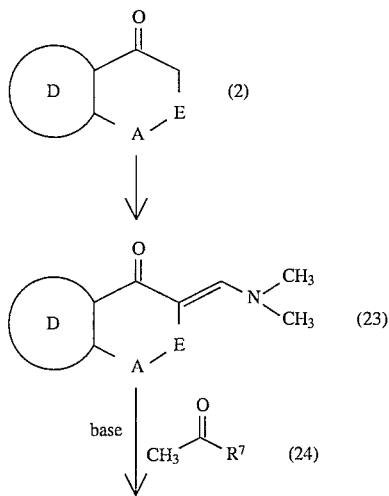

16

-continued
[Preparation process 5]

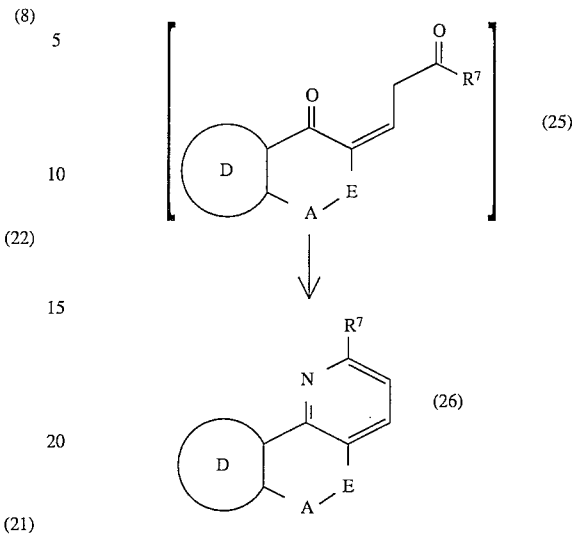

wherein the ring D, R⁷, A and E are each as defined above.

A ketone compound (2) can be converted into a compound represented by the general formula (23) by reacting it with N,N-dimethylformamide dimethyl acetal. The solvent to be used in this reaction may be selected from among aromatic hydrocarbons such as benzene, toluene and xylene; aprotic solvents such as N,N-dimethylformamide and dimethyl sulfoxide; and chlorinated hydrocarbons such as dichloromethane, chloroform and 1,2-dichloroethane. The reaction temperature may range from 0° C. to the boiling point of the solvent used.

Then, a compound represented by the general formula (25) can be prepared by reacting the compound (23) with an acetylated compound represented by the general formula (24) in the presence of a base.

The base to be used in this reaction includes alkali metal hydroxides such as sodium hydroxide and potassium hydroxide; and alkali metal alkoxides such as sodium methoxide, sodium ethoxide and potassium t-butoxide. The solvent to be used in this reaction may be any one which is inert to the reaction, and preferable examples of the solvent include methanol, ethanol, tetrahydrofuran and N,N-dimethylformamide. It is preferable that the reaction be conducted at a temperature near room temperature, though the reaction temperature may range from 0° C. to the boiling point of the solvent used.

The obtained compound (25) can be converted into a pyridine derivative represented by the general formula (26) by reacting it with ammonia or an ammonium salt such as ammonium acetate or ammonium chloride. This reaction can be accelerated by the addition of an acid which is used also as a dehydrating agent, for example, acetic acid.

[Preparation process 6]

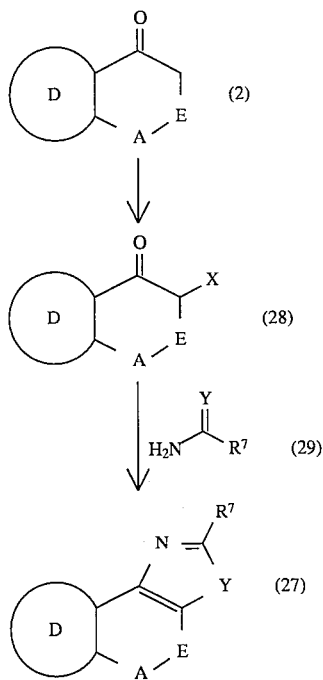

wherein the ring D, $R^7$, A and E are each as defined above; X represents a halogen atom such as Cl, Br or I; and Y represents S or NH.

A thiazole or imidazole derivative represented by the general formula (27) can be prepared by halogenating the α-position of a ketone compound (2) and reacting the obtained compound (28) with a thioamide or amidine represented by the general formula (29). The halogenating reagent to be used in the halogenation includes bromine, copper bromide, N-bromosuccinimide, chlorine, N-chlorosuccinimide and bromine. The conversion of the compound (28) into the heterocycle compound (27) is conducted in the presence of a base such as pyridine, triethylamine or potassium carbonate in a solvent such as methanol, ethanol, isopropanol, tetrahydrofuran or N,N-dimethylformamide at a temperature ranging from 0° C. to the boiling point of the solvent used.

[Preparation process 7]

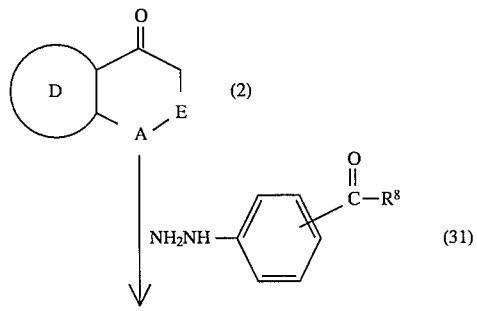

-continued
[Preparation process 7]

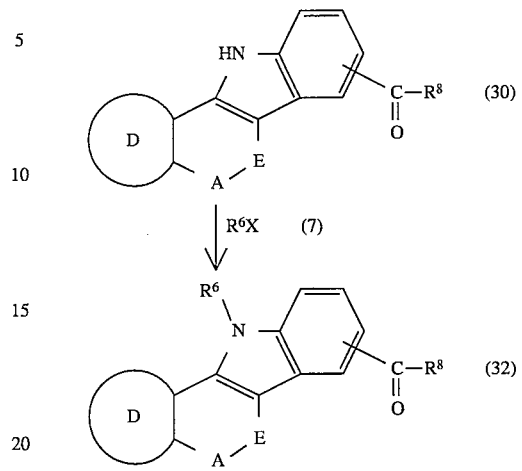

wherein the ring D, $R^6$, $R^8$, A and E are each as defined above; and X represents a halogen atom.

An indole derivative represented by the general formula (30) can be prepared by reacting a ketone compound (2) with a hydrazine (31) in the presence of an acid catalyst such as hydrochloric acid, polyphosphoric acid or zinc chloride according to the Fischer process for the synthesis of indoles.

Further, a substituent can be introduced into the indole derivative (30) by reacting the derivative (30) with a halide represented by the general formula (7) in the same manner as that described in the above Preparation process 1.

[Preparation process 8]

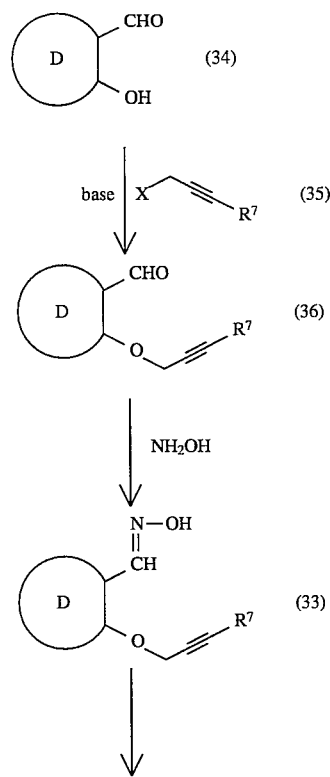

[Preparation process 8]

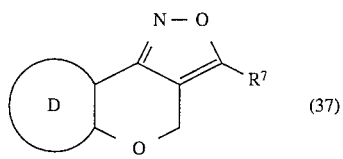

wherein the ring D and $R^7$ are each as defined above; and X represents a halogen atom.

An oxime compound represented by the general formula (33) can be prepared by reacting a salicylaldehyde represented by the general formula (34) with a halide represented by the general formula (35) to form a compound represented by the general formula (36) and reacting the compound (36) with hydroxylamine. The above alkylation can be conducted in the same manner as that described in the Preparation process 1. The obtained oxime compound (33) can he converted into an objective isoxazole compound (37) by adding an oxidizing agent to the oxime compound (33) to cause the conversion into a nitrile oxide and the cyclization through intramolecular 1,3-dipolar addition to acetylene. The oxidizing agent to be used in this process includes sodium hypochlorite, nitrosyl chloride, N-chlorosuccinimide and N-bromosuccinimide. The solvent to be used therein includes methylene chloride and N,N-dimethylformamide and it is preferable that the reaction temperature be near room temperature.

[Preparation process 9]

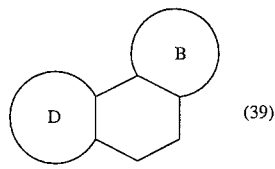

↓ dehydrogenation

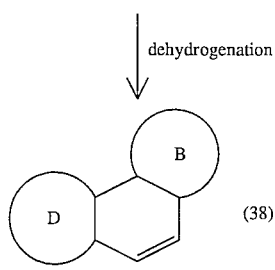

wherein the rings D and B are each as defined above.

A compound represented by the general formula (38) can be prepared by dehydrogenating a compound represented by the general formula (39). The dehydrogenating agent to be used in this process includes 2,3-dichloro-5,6-dicyano-1,4-benzoquinone, palladium-carbon, sulfur and selenium dioxide. This dehydrogenation may be conducted in the absence of any solvent or in the presence of an aromatic hydrocarbon such as benzene, toluene or xylene at a temperature of 0° to 300° C., preferably 80° to 300° C.

[Preparation process 10]

The compounds prepared by the above Preparation processes 1 to 9 or other processes can be converted into other compounds of the present invention represented by the general formula (I) by the conventional replacement of $R^7$.

For example, a carbonic ester represented by the general formula (I) wherein $R^7$ is a group having a carboalkoxy group can be converted into a free carboxylic acid or a physiologically acceptable salt thereof by alkaline hydrolysis. This alkaline hydrolysis is conducted in the presence of an excess of an alkali metal hydroxide, particularly sodium hydroxide or potassium hydroxide in a mixture of water with an alcohol such as methanol, ethanol or propanol, tetrahydrofuran or 1,4-dioxane at a temperature ranging from room temperature to the boiling point of the solvent used.

The amide compound of the present invention can be prepared by converting the corresponding carboxylic acid compound into the corresponding acid chloride, acid azide or acid anhydride and reacting the chloride, azide or anhydride with an amine represented by the general formula: $NR^9R^{10}$ (wherein $R^9$ and $R^{10}$ are each as defined above) in a known method.

The ester compound of the present invention can be prepared by transesterification in a known method. Alternatively, the ester compound of the present invention can be prepared by reacting the corresponding carboxylic acid compound with an alcohol compound represented by the general formula: $HO-R^{8a}$ (wherein $R^{8a}$ represents a lower alkyl group or a morpholylalkyl group) in the presence of a condensing agent such as dicyclohexylcarbodiimide; or by converting the corresponding carboxylic acid compound into the corresponding acid chloride, acid azide or acid anhydride and reacting the chloride, azide or anhydride with an alcohol compound represented by the general formula: $HO-R^{8a}$ (wherein $R^{8a}$ is as defined above).

[Preparation of starting material]

The compound represented by the general formula (2) which is used in the above Preparation processes as the starting material can be prepared by the following process:

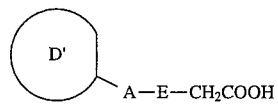

↓ cyclization

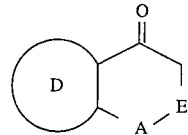

wherein the ring D, A and E are each as defined above, and the ring D' represents the following formula:

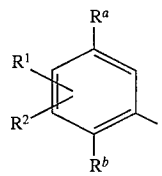

(wherein $R^1$, $R^2$, $R^a$ and $R^b$ are each as defined above).

That is, the compound (2) can be prepared directly from a carboxylic acid compound represented by the general formula (40) by cyclizing it in polyphosphoric acid. Alternatively, the compound (2) can be prepared by converting the carboxylic acid compound (40) into a corresponding acid chloride by the use of thionyl chloride or phosphorus pentachloride and cyclizing the acid chloride in the presence of a Lewis acid such as aluminum chloride, titanium tetrachloride or stannic chloride in a solvent such as carbon disulfide or dichloromethane at a temperature ranging from 0° C. to the boiling point of the solvent used.

The starting material or the intermediate which is preferably used for the production of the compounds represented by the general formula (I) according to the present invention, is represented by the following general formula (II):

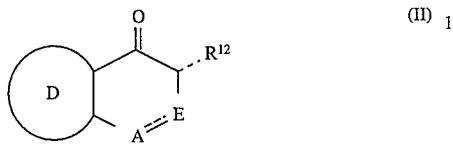

wherein the ring D, A, E and $R^{12}$ are each as defined above.

Preferably examples of the starting material or the intermediate represented by the above general formula (II) include those represented by the following formulas:

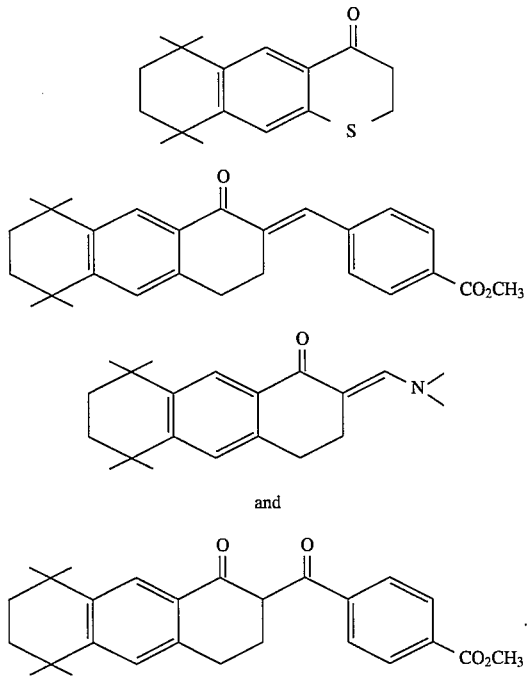

and

Further, salts of the compound represented by the above general formula (II) can also be used as the starting material or the intermediate for the production of the compounds represented by the general formula (I) according to the present invention.

These compounds (the starting material or intermediate) are novel compounds and important for the preparation of the compounds of the present invention which are useful as medicines.

A pharmacological experimental example will now be given to illustrate the effects of the present invention.

EXPERIMENTAL EXAMPLE

Receptor binding assay using human promyelocytic leukemia cell, HL60

It has been known that a receptor for all-trans retionic acid [i.e., retinoic acid receptor (RAR)] is present in the nucleus of HL 60 cell (see Clara Nervi et al., Proc. Natl. Acad. Sci. USA, 86, 5854 (1989)). Therefore, the extent of specific binding of all-trans retionic acid to RAR was determined by the use of an extract from HL 60 cell nuclei; and the ability of each compound to bind to RAR was determined based on the inhibitory activity of the compound against the above specific binding.

The above cell nucleus extract was prepared as follows.

HL 60 cells ($5 \times 10^8$) were suspended in 15 ml of a solution A [comprising 5 mM of sodium phosphate (pH: 7.4), 10 mM of monothioglycerol, 10% (v/v) of glycerol, 1 mM of phenylmethylsulfonyl fluoride (PMSF), 10 µg/ml of aprotinin and 25 µg/ml of leupeptin). The obtained suspension was homogenized with a homogenizer and centrifuged to remove a formed supernatant. The obtained sediment was suspended in 15 ml of a solution B [comprising 10 mM of Tris-HCl (pH: 8.5), 10 mM of monothioglycerol, 10% (v/v) of glycerol, 1 mM of PMSF, 10 µg/ml of aprotinin, 25 µg/ml of leupeptin and 0.8 M of KCl]. The obtained suspension was allowed to stand at 4° C. for one hour and ultracentrifuged (under the conditions of 100,000×g and 4° C. for one hour). The supernatant thus obtained was stored in a state freezed at −80° C. and used as the cell nucleus extract [see Methods in Enzymology, 189: 248).

The receptor binding assay was conducted as follows.

180 µl of the above extract and 10 µl of a dilution of all-trans retionic acid or a compound to be tested were put in each well of a 96-well polypropylene plate, followed by the addition thereto of $^3$H-all-trans retionic acid in an amount of 10 µl/well. The plate was allowed to stand at 4° C. for 16 hours. A solution containing 3% of charcoal and 0.3% of dextran was added to the reaction mixture in the well and the obtained mixture was centrifuged to remove free $^3$H-all-trans retionic acid. The intensity of radiation of the supernatant was determined with a scintillation counter. The extent of specific binding of all-trans retinoic acid to RAR was determined by taking the intensity of radiation, observed when 200-fold excess of all-trans retinoic acid was added, as that of a nonspecific binding, and substracting the intensity of radiation thus taken from that of the one determined above. The following compounds inhibited the binding of $^3$H-all-trans retionic acid to RAR depending on the concentration. The 50% inhibitory concentration of each compound was calculated and given in Table 1.

Antagonism against all-trans retinoic acid in inducing the differentiation of HL60 cell It has been known that a human promyelocytic leukemia cell strain HL60 is differentiated into granulocytic cells in the presence of all-trans retinoic acid (see Breitman, T., Selonick, S., and Collins, S., Proc. Natl. Acad. Sci. USA, 77, 2936(1980)). Generally, a cell forms a specific differentiation antigen on its surface, when it has achieved differentiation. When an HL60 cell is differentiated into a granulocytic cell, CD11b which is an antigen discriminating granulocyte or monocute is formed on the surface of the cell (see Fontana, J. A., Reppuci, A., Durham, J. P., and Mirand, D., Cancer Res. 46, 2469 to 2473 (1986)). The antagonism against the differentiation of HL60 into granulocytic cell which is induced by all-trans retionic acid was studied by utilizing the above phenomenon.

HL60 cells were cultured and maintained in a culture medium prepared by adding 10% of inactivated bovine fetus serum, 1 mM of sodium pyruvate, 50 µM of β-mercaptoethanol, 100 I.U./ml of penicillin and 100 µg/ml of streptomycin to RPMI1640 (a culture medium formulated in Rosewell Park Memorial Institute).

An HL60 cell suspension ($1 \times 10^5$ cells/ml) was put in a 24-well plate in an amount of 1 ml/well, followed by the addition thereto of 30 mM of all-trans retionic acid and a retinoid antagonist in various amounts. The resulting plate was incubated in an incubator (5% $CO_2$/air) for 5 days. After the incubation, the cells of each well were recovered into a test tube, followed by the addition thereto of an FITC-labeled monoclonal antibody reactive with CD11b which is an antigen specific to granulocyte or monocute. The resulting cells were immobilized with 0.2% paraformaldehyde. The immobilized cell suspension was examined by flow cytometry for the proportion of CD11b-positive cells in the above HL60 cell group in each well (see Miller, L. J., Schwarting, R., and Springer, T. A., J. Immunol. 137, 2891 to 2900 (1986)). The following compounds lowered the proportion of CD11b-positive cells induced by all-trans retionic acid (30 M) depending on the concentration and the 50% inhibitory concentration of each compound was calculated and given in the Table 1.

TABLE 1

| Ex. No. | Receptor binding assay using HL60 IC50 (nM) | Antagonism against all-trans retinoic acid (30 nM) in inducing the differentiation of HL 60 cell $IC_{50}$ (μM) |
| --- | --- | --- |
| 1 | 4 | 0.7 |
| 2 | 50 | 6.7 |
| 4 | <0.5 | 1.0 |
| 7 | 22 | 0.56 |
| 11 | 9 | 1.2 |
| 14 | 50 | 2.2 |
| 16 | <0.5 | 0.12 |
| 18 | 4.2 | 2.7 |
| 19 | 0.5 | 0.48 |
| 22 | 32 | 14 |
| 106 | 26 | 3.8 |
| TD-550 1) | 50 | >10 (2.1 against all-trans retinoic acid (3 nM)) |
| TD-650 1) | >50 | >10 (2.6 against all-trans retinoic acid (3 nM)) |
| R041-5253 2) | 9 | 7.2 |

1) Cell Biol. Rev., 25, 209 (1991)
2) Proc. Natl. Acad. Sci., 89, 7129 (1992)

It can be understood from the results of the above Experimental Example that the compound of the present invention has an extremely high RARs-binding power and exhibits all-trans retinoic acid antagonism and therefore the compound is expected to be efficacious against the following diseases:

various cornification disorders, psoriasis, acne, leukoplakia, and xeroderma pigmentosum, various alopecia such as alopecia areata, seborrheic alopecia, and cachectic alopecia, postmenopausal, senile and sudden osteoporoses, diabetic osteoporosis, osteoporosis resulting from rheumatoid arthritis, renal osteomalacia, and ectopic bone formation, rheumatoid arthritis, osteoarthritis, and periarthritis of the shoulder, activation of immune function in immunodeficiency, cytomegalovirus infection diseases in low immune function or of fetus, and opportunistic infection, hyperthyroidism, vital infections such as HIV infection, HVB infection, HCV infection and HILV-I infection, squamous cell carcinoma, bladder cancer, pulmonary carcinoma, esophageal carcinoma, and cancer of head or neck, hypercalcemia, and pulmonary fibrosis, hepatic fibrosis, and hepatic cirrhosis.

In using the compounds of the present invention as therapeutic and preventive agents for these diseases, they may be each administered orally as a tablet, powder, granule, capsule or syrup, or parenterally as a suppository, injection, external preparation or drop.

The compounds of the present invention can be converted into medicines for oral and parenteral administration by the use of the conventional pharmaceutically acceptable fillers or carriers according to the conventional processes.

An injection or drop according to the present invention is prepared by adding a pH modifier, buffer, stabilizer and/or solubilizing agent to an active ingredient, followed by freeze drying at need, and formulating the obtained mixture into a subcutaneous, intramuscular or intravenous injection or a drop by the conventional processes.

EXAMPLES

The present invention will now be described in more detail with reference to the following Examples which should not be considered to limit the present invention. The preparation of the starting materials used in the Examples will also be described in Referential Examples.

With respect to some compounds, no peak assignable to carboxylic acid was observed in nuclear magnetic resonance (NMR) spectroscopy.

The melting point of each compound was determined by the use of a melting-point apparatus for trace samples (mfd. by Yanagimoto Manufacturing Co., Ltd.)

[Example 1]
4-(1-Ethyl-4,5,7,8,9,10-hexahydro-7,7,10,10-tetramethylanthra[2,1-d]pyrazol-3yl)benzoic acid

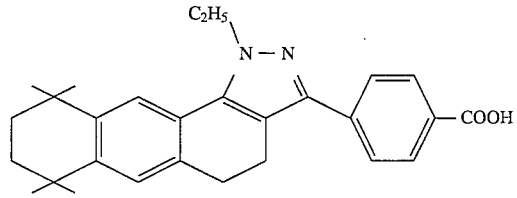

(1) Methyl 4-(3,4,5,6,7,8-hexahydro-5,5,8,8-tetramethyl-1(2H)-anthracenon-2-ylcarbonyl)benzoate

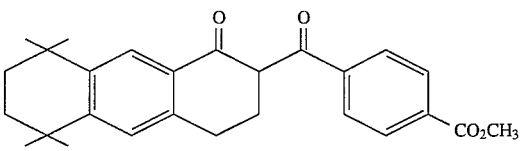

1.5 g of diisopropylamine was dissolved in 50 ml of anhydrous tetrahydrofuran, followed by the addition thereto of 8.8 ml of a 1.6 M solution of n-butyllithium in hexane at 0° C. The obtained mixture was stirred for 10 minutes and cooled to −78° C., followed by the addition thereto of 20 ml of a solution of 3.0 g of 3,4,5,6,7,8-hexahydro-5,5,8,8-tetramethyl-1(2H)-anthracenone in anhydrous tetrahydrofuran. The obtained mixture was stirred for 30 minutes, followed by the dropwise addition thereto of 20 ml of a solution of 2.8 g of monomethyl terephthalate chloride in anhydrous tetrahydrofuran. The reaction mixture was brought to room temperature and poured into cool dilute hydrochloric acid. The obtained mixture was extracted with ethyl acetate. The organic phase was washed with water, a saturated aqueous solution of sodium hydrogencarbonate and a saturated aqueous solution of common salt successively and dried over anhydrous magnesium sulfate. The solvent was distilled off under reduced pressure and the residue was purified by silica gel column chromatography (developer: 5% ethyl acetate/n-hexane). The obtained solid was washed with methanol to give 2.5 g of the title compound as a pale-yellow solid.

m.p.; 131°–132° C. $^1$H-NMR (400 MHz, CDCl$_3$) δ (ppm); 1.30(s, 6H), 1.34(s, 6H), 1.70(s, 4H), 2.67–2.80(m, 4H), 3.95(s, 3H), 7.14(s, 1H), 7.63(d, J=8.4 Hz, 2H), 7.99(s, 1H), 8.12(d, J=8.4 Hz, 2H)

(2) Methyl 4-(4,5,7,8,9,10-hexahydro-7,7,10,10-tetramethylanthra[2,1-d]pyrazol-3-yl)benzoate

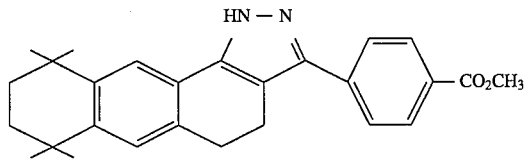

2.5 g of methyl 4-(3,4,5,6,7,8-hexahydro-5,5,8,8-tetramethyl-1(2H)-anthracenon-2-ylcarbonyl)benzoate was suspended in 80 ml of methanol, followed by the addition thereto of 0.4 g of hydrazine monohydrate. The obtained mixture was heated under reflux for 2 hours and cooled to room temperature by allowing to stand. The precipitated solid was recovered by filtration and washed with methanol. 2.0 g of the title compound was obtained as a pale-yellow solid.

m.p. 241°–243° C. $^1$H-NMR (400 MHz, DMSO-D$_6$) δ (ppm); 1.22(s, 6H), 1.26(s, 6H), 1.62(s, 4H), 2.80–2.96(m, 4H), 3.85(s, 3H), 7.24(s, 1H), 7.66(s, 1H), 7.84(d, J=8.4 Hz, 2H), 8.02(d, J=8.4 Hz, 2H)

(3) Methyl 4-(1-ethyl-4,5,7,8,9,10,hexahydro-7,7,10,10-tetramethylanthra[2,1,d]pyrazol-3-yl)benzoate

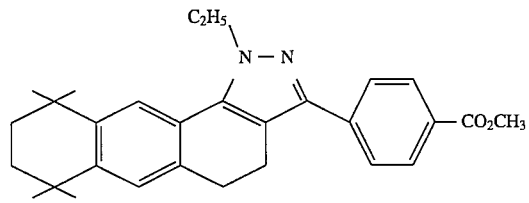

0.45 g of methyl 4-(4,5,7,8,9,10-hexahydro-7,7,10,10-tetramethylanthra[2,1-d]pyrazol-3-yl)benzoate was dissolved in 20 ml of N,N-dimethylformamide, followed by the addition thereto of 0.05 g of sodium hydride (as a 60% solution in oil) under cooling with ice. The obtained mixture was stirred for 10 minutes, followed by the addition thereto of 0.13 ml of ethyl iodide. The obtained mixture was stirred for 10 minutes and further stirred at room temperature for 30 minutes. The reaction mixture was poured onto ice-water. The resulting mixture was extracted with ethyl acetate. The organic phase was washed with a saturated aqueous solution of common salt and dried over anhydrous magnesium sulfate. The solvent was distilled off under reduce pressure. The solid residue was washed with methanol to give 0.25 g of the title compound as a white solid.

m.p.; 180°–181° C. $^1$H-NMR (400 MHz, CDCl$_3$) δ (ppm); 1.31(s, 6H), 1.33(s, 6H), 1.62 ( t, J=6.8 Hz, 3H), 1.70(s, 4H), 2.90(s, 4H), 3.93(s, 3H), 4.55(q, J=6.8 Hz, 2H), 7.26(s, 1H), 7.48(s, 1H), 7.78(d, J=8.4 Hz, 2H), 8.10(d, J=8.4 Hz, 2H)

(4) 4-(1-Ethyl-4,5,7,8,9,10-hexahydro-7,7,10,10-tetramethylanthra[2,1-d]pyrazol-3-yl)benzoic acid

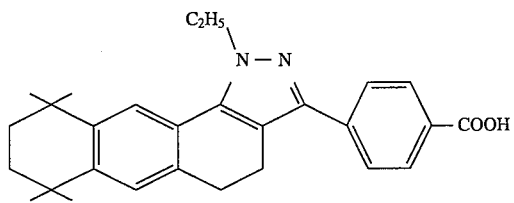

0.25 g of methyl 4-(1-ethyl-4,5,7,8,9,10-hexahydro-7,7,10,10-tetramethylanthra[2,1-d]pyrazol-3-yl)benzoate was dissolved in a mixture comprising 10 ml of methanol and 10 ml of tetrahydrofuran, followed by the addition thereto of 5 ml of a 5N aqueous solution of sodium hydroxide. The obtained mixture was heated under reflux for 30 minutes and cooled to room temperature by allowing to stand, followed by the addition thereto of 20 ml of water. The pH of the obtained mixture was adjusted to 4 with dilute hydrochloric acid to precipitate a solid. This solid was recovered by filtration and washed with water. 0.22 g of the title compound was obtained as a white solid.

m.p.; 278°–279° C. $^1$H-NMR (400 MHz, DMSO-d$_6$) δ (ppm); 1.23(s, 6H), 1.26(s, 6H), 1.47(t, J=6.8 Hz, 3H), 1.64(s, 4H), 2.82(brs, 4H), 4.50(q, J=6.8 Hz, 2H), 7.33(s, 1H), 7.44(s, 1H), 7.77(d, J=8.4 Hz, 2H), 7.99(d, J=8.4 Hz, 2H)

The compounds of Examples 2 to 5, of which structural formulas or the like will be described in Table 2, were prepared in the same manner as that of the Example 1.

TABLE 2

| Ex. | structural formula | $^1$H-NMR(400MHz,DMSO-d6)δ | m.p. (C.°) |
|---|---|---|---|
| 2 | ![structure] | 1.23(s, 6H), 1.27(s, 6H), 1.56(d, J=6.5Hz, 6H), 1.63(s, 4H), 2.76(brs, 4H), 4.88–4.98(m, 1H), 7.30(s, 1H), 7.40(s, 1H), 7.60(d, J=8.4Hz, 2H), 7.92(d, J=8.4Hz, 2H) | 236–238 |

TABLE 2-continued

| Ex. | structural formula | ¹H-NMR(400MHz,DMSO-d6)δ | m.p. (C.°) |
|---|---|---|---|
| 3 | 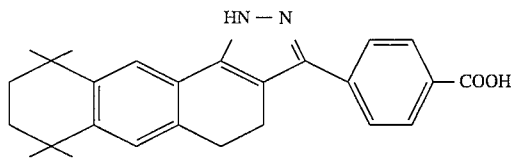 —COOH | 0.34~0.41(m, 2H), 0.48~0.55(m, 2H), 1.23(s, 6H), 1.30(s, 6H), 1.64 (s, 4H), 2.83(brs, 4H), 4.40(d, J=6.5 Hz, 2H), 7.32(s, 1H), 7.57(s, 1H), 7.77(d, J=8.4Hz, 2H), 7.99(d, J=8.4Hz, 2H) | 266~269 |
| 4 | (structure with benzyl-N—N) —COOH | 0.90(s, 6H), 1.18(s, 6H), 1.52(s, 4H) 2.78~2.96(m, 4H), 5.73(s, 2H) 7.00~7.40(m, 7H), 7.82(d, J=8.4Hz, 2H), 8.00(d, J=8.4Hz, 2H) | >290 |
| 5 | (structure with pyridylmethyl-N—N) —COOH | 0.97(s, 6H), 1.20(s, 6H), 1.53(s, 4H) 2.79~2.95(m, 4H)5.82(s, 2H), 7.08(s, 1H), 7.30(s, 1H), 7.33~7.47 (m, 2H), 7.82(d, J=8.4Hz, 2H), 8.00(d, J=8.4Hz, 2H), 8.42(brs, 1H) 8.49(brs, 1H) | 294~295 |

[Example 6]

4-(4,5,7,8,9,10-Hexahydro-7,7,10,10-tetramethylanthra[2,1-d]pyrazol-3-yl)benzoic acid 0.5 g of methyl 4-(4,5,7,8,9,10-hexahydro-7,7,10,10-tetramethylanthra[2,1-d]pyrazol-3-yl)benzoate was suspended in 10 ml of methanol, followed by the addition thereto of 5 ml of a 5N aqueous solution of sodium hydroxide. The obtained mixture was heated under reflux for one hour and cooled by allowing to stand, followed by the addition thereto of 20 ml of water. The pH of the resulting mixture was adjusted to 4 with dilute hydrochloric acid to precipitate a solid. This solid was recovered by filtration and washed with water. 0.35 g of the title compound was obtained as a white solid.

m.p.; >300° C. ¹H-NMR (400 MHz, DMSO-d₆) δ (ppm); 1.23(s, 6H), 1.26(s, 6H), 1.64(s, 4H), 2.82–2.96(m, 4H), 7.24(s, 1H), 7.65(s, 1H), 7.80(d, J=8.4 Hz, 2H), 8.00(d, J=8.4 Hz, 2H)

[Example 7]

4-(4,5,7,8,9,10-Hexahydro-1,7,7,10,10-pentamethylanthra[2,1-d]pyrazol-3-yl)benzoic acid

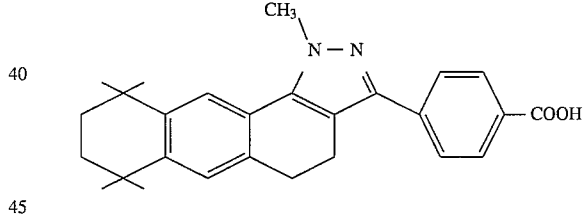

Methyl 4-(4,5,7,8,9,10-hexahydro-1,7,7,10,10-pentamethylanthra[2,1-d]pyrazol-3-yl)benzoate

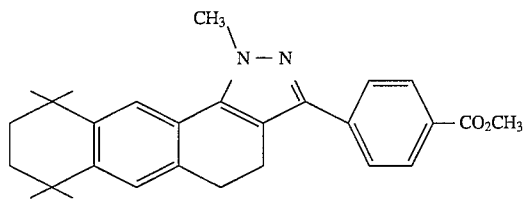

4.5 g of methyl 4-(3,4,5,6,7,8-hexahydro-5,5,8,8-tetramethyl-1(2H)-anthracenon-2-ylcarbonyl)benzoate was suspended in 100 ml of methanol, followed by the addition thereto of 0.64 g of monomethylhydrazine. The obtained mixture was heated under reflux for 2 hours and cooled by allowing to stand to precipitate a solid. This solid was recovered by filtration and washed with methanol. 3.0 g of the title compound was obtained as a pale-yellow solid.

m.p.; 233°–235° C. ¹H-NMR (400 MHz, CDCl₃) δ (ppm); 1.30(s, 6H), 1.33(s, 6H), 1.70(s, 4H), 2.89(brs, 4H), 3.93(s, 3H), 4.22(s, 3H), 7.26(s, 1H), 7.52(s, 1H), 7.78(d, J=8.4 Hz, 2H), 8.08(d, J=8.4 Hz, 2H)

4-(4,5,7,8,9,10-Hexahydro-1,7,7,10,10-pentamethylanthra[2,1-d]pyrazol-3-yl)benzoic acid

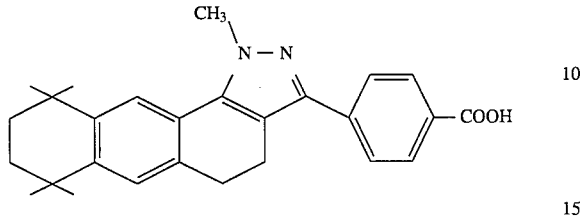

3.0 g of methyl 4-(4,5,7,8,9,10-hexahydro-1,7,7,10,10-pentamethylanthra[2,1-d]pyrazol-3-yl)benzoate was dissolved in a mixture comprising 30 ml of methanol and 30 ml of tetrahydrofuran, followed by the addition thereto of 20 ml of a 5N aqueous solution of sodium hydroxide. The obtained mixture was heated under reflux for 40 minutes and cooled to room temperature by allowing to stand, followed by the addition thereto of 50 ml of water. The pH of the resulting mixture was adjusted to 4 with dilute hydrochloric acid to precipitate a solid. This solid was recovered by filtration and washed with water. 2.7 g of the title compound was obtained as a white solid.

m.p.; 284° C. (dec.) ¹H-NMR (400 MHz, DMSO-d₆) δ (ppm); 1.23(s, 6H), 1.30(s, 6H), 1.64(s, 4H), 2.82(s, 4H), 4.17(s, 3H), 7.31(s, 1H), 7.54(s, 1H), 7.77(d, J=8.4 Hz, 2H), 7.98(d, J=8.4 Hz, 2H)

The compounds of Examples 8 and 9, of which structural formulas or the like will be described in Table 3, were prepared in the same manner as that of the Example 7.

TABLE 3

| Ex. | structural formula | ¹H-NMR(400MHz, DMSO-d6)δ | m.p. (C.°) |
| --- | --- | --- | --- |
| 8 | ![structure] | 1.24(s, 6H), 1.29(s, 6H), 1.66(s, 4H), 1.28~2.06(m, 10H), 2.80(brs, 4H), 4.45~4.56(m, 1H), 7.35(s, 1H), 7.37(s, 1H), 7.78(d, J=8.4Hz, 2H), 7.98(d, J=8.4Hz, 2H) | 284–286 |
| 9 | ![structure] | 0.83(s, 6H), 1.21(s, 6H), 1.45~1.58 (m, 4H), 2.94(s, 4H), 6.58(s, 1H), 7.30(s, 1H), 7.51~7.62(m, 5H), 7.83(d, J=8.4Hz, 2H), 8.00(d, J=8.4Hz, 2H). | 277–279 |

The compounds of Examples 10 to 13, of which structural formulas or the like will be described in Table 4, were prepared from the ketone compounds prepared in Referential Examples 1, 2 and 7 in the same manners as those of the Examples 1, 6 and 7.

TABLE 4

| Ex. | structural formula | $^1$H-NMR(400MHz, DMSO-d6)δ | m.p. (C.°) |
|---|---|---|---|
| 10 | | 1.22(s, 6H), 1.27(s, 6H), 1.63(s, 4H), 4.21(s, 2H), 7.27(s, 1H) 7.75(s, 1H), 7.78(d, J=8.4Hz, 2H), 8.01(d, J=8.4Hz, 2H) | >300 |
| 11 | | 1.23(s, 6H), 1.30(s, 6H), 1.64(s, 4H) 4.08(s, 2H), 4.15(s, 3H), 7.40(s, 1H) 7.65(s, 1H), 7.74(d, J=8.4Hz, 2H), 7.98(d, J=8.4Hz, 2H) | >300 |
| 12 | | 1.28(s, 6H), 1.30(s, 6H), 1.65(s, 4H) 2.08~2.20(m, 2H), 2.44~2.56 (m, 4H), 3.95(s, 3H), 7.33(s, 1H), 7.42(s, 1H), 7.71(d, J=8.4Hz, 2H), 8.00(d, J=8.4Hz, 2H) | 274–275 |
| 13 | | 1.20(s, 6H), 1.28(s, 6H), 1.62(s, 4H) 2.48(brs, 2H), 3.14(t, J=7.0Hz, 2H), 4.39(t, J=7.0Hz, 2H), 6.92(s, 1H), 7.81(d, J=8.4Hz, 2H), 7.98(s, 1H), 8.00(d, J=8.4Hz, 2H) | >300 |

[Example 14]

4-(7,8,9,10-Tetrahydro-1,7,7,10,10-pentamethylanthra-[2,1-d]pyrazol-3-yl)benzoic acid

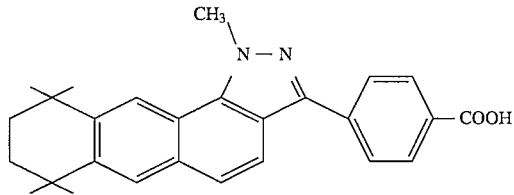

0.48 g of methyl 4-(4,5,7,8,9,10-hexahydro-1,7,7,10,10-pentamethylanthra[2,1-d]pyrazol-3-yl)benzoate was dissolved in 30 ml of benzene, followed by the addition thereto of 0.51 g of 2,3-dichloro-5,6-dicyano-1,4-benzoquinone. The obtained mixture was heated under reflux for 20 hours and cooled to room temperature by allowing to stand, followed by the addition thereto of ethyl acetate. The organic phase was washed with a 1N aqueous solution of sodium hydroxide and water successively, dried over anhydrous magnesium sulfate and concentrated under reduced pressure. The obtained residue was purified by silica gel column chromatography (developer: 8% ethyl acetate/n-hexane) to give 0.2 g of a white solid.

This solid was dissolved in a mixture comprising 5 ml of methanol and 5 ml of tetrahydrofuran, followed by the addition thereto of 5 ml of a 5N aqueous solution of sodium hydroxide. The obtained mixture was heated under reflux for 30 minutes and cooled to room temperature by allowing to stand, followed by the addition thereto of 10 ml of water. The pH of the resulting mixture was adjusted to 4 with dilute hydrochloric acid to precipitate a solid. This solid was recovered by filtration and washed with water. 0.15 g of the title compound was obtained as a white solid.

m.p.; 272°–274° C. $^1$H-NMR (400 MHz, DMSO-d$_6$) δ (ppm); 1.37(s, 6H), 1.43(s, 6H), 1.76(s, 4H), 4.58(s, 3H), 7.59(d, J=8.8 Hz, 1H), 7.93(d, J=8.8 Hz, 1H), 8.03(s, 1H), 8.06(d, J=8.4 Hz, 2H), 8.11 (d, J=8.4 Hz, 2H), 8.43(s, 1H)

[Example 15]

The compound of Example 15 was prepared in the same manner as that of the Example 14.

4-(7,8,9,10-Tetrahydro-7,7,10,10-tetramethylanthra-[2,1-d]pyrazol-3-yl)benzoic acid

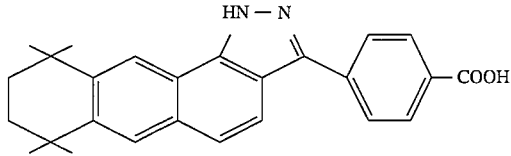

m.p.; >300° C. ¹H-NMR (400 MHz, DMSO-d₆) δ (ppm); 1.34(s, 6H), 1.40(s, 6H), 1.74(s, 4H), 7.54 ( d, J=8.8 Hz, 1H), 7.95 ( d, J=8.8 Hz, 1H), 7.98(s, 1H), 8.07(d, J=8.4 Hz, 2H), 8.14(d, J=8.4 Hz, 2H), 8.50(s, 1H)

[Example 16]
4-[4,5,7,8,9,10-Hexahydro-7,7,10,10-tetramethyl-1(3-pyridylmethyl)anthra[1,2-b]pyrrol-3-yl]benzoic acid

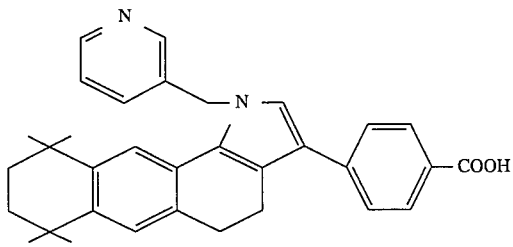

Methyl    4-[(3,4,5,6,7,8-hexahydro-5,5,8,8-tetramethyl-1(2H)-anthracenon-2-yl)hydroxymethyl]benzoate

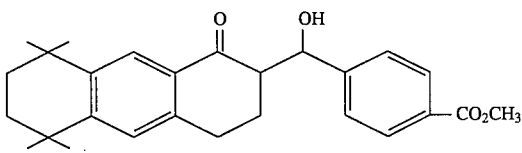

8.0 g of 3,4,5,6,7,8-hexahydro-5,5,8,8-tetramethyl-1(2H)-anthracenone and 5.1 g of methyl terephthalaldehydate were dissolved in 200 ml of methanol, followed by the addition thereto of 0.3 g of sodium hydroxide. The obtained mixture was stirred at room temperature for 24 hours to precipitate a solid. This solid was recovered by filtration and washed with methanol. 8.4 g of the title compound was obtained as a white solid.

m.p.; 186°–187° C. ¹H-NMR (400 MHz, CDCl₃) δ (ppm); 1.28(s, 6H), 1.32(s, 3H), 3H), 1.33(s, 3H), 1.75–1.84(m, 1H), 1.98–2.13(m, 1H), 2.76–2.92(m, 3H), 3.08(d, J=5.0 Hz, 1H), 3.93(s, 3H) , 5.70–5.76(m, 1H), 7.13(s, 1H), 7.45(d, J=8.4 Hz, 2H), 8.02(s, 1H), 8.04(d, J=8.4Hz, 2H)

Methyl 4-(3,5,6,7,8-pentahydro-5,5,8,8-tetramethyl-1(4H)-anthracenon-2-ylidene)benzoate

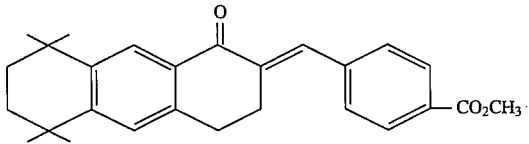

8.4 g of methyl 4-[(3,4,5,6,7,8-hexahydro-5,5,8,8-tetramethyl-1(2H)-anthracenon-2-yl)-hydroxymethyl]benzoate was suspended in 100 ml of 1,4-dioxane, followed by the addition thereto of 5 ml of concentrated sulfuric acid. The obtained mixture was stirred at room temperature for 3 hours and extracted with 300 ml of ethyl acetate. The organic phase was washed with water, a saturated aqueous solution of sodium hydrogencarbonate and a saturated aqueous solution of common salt successively, dried over anhydrous magnesium sulfate and concentrated under reduced pressure. The obtained residue was washed with n-hexane to give 7.1 g of the title compound as a white solid.

m.p.; 137° C. ¹H-NMR (400 Hz, CDCl₃) δ (ppm); 1.30(s, 6H), 1.33(s, 6H), 1.70(s, 4H), 2.90(t, J=6.4 Hz, 2H), 3.08(t, J=6.4Hz, 2H ), 3.93(s, 3H), 7.17(s, 1H), 7.48(d, J=8.4 Hz, 2H ), 7.81(s, 1H), 8.08(d, J=8.4 Hz, 2H), 8.10(s, 1H)

Methyl    4-[1-(3,4,5,6,7,8-hexahydro-5,5,8,8-tetramethyl-1(2H)-anthracenon-2-yl)-2,2-dimethoxyethyl]-benzoate

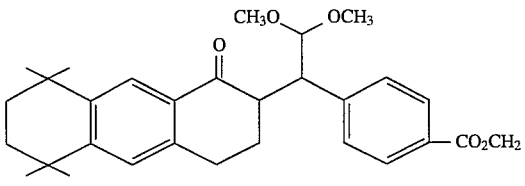

5.0 g of methyl 4-(3,5,6,7,8-pentahydro-5,5,8,8-tetramethyl-1(4H)-anthracenon-2-ylidene)benzoate was dissolved in a mixture comprising 40 ml of nitromethane and 20 ml of tetrahydrofuran, followed by the addition of 0.5 g of a 40% methanolic solution of benzyltrimethylammonium hydroxide. The obtained mixture was stirred at room temperature for 4 hours, followed by the addition of ethyl acetate to conduct extraction. The organic phase thus obtained was washed with dilute hydrochloric acid, water, a saturated aqueous solution of sodium hydrogencarbonate and a saturated aqueous solution of common salt successively, dried over anhydrous magnesium sulfate and concentrated under reduced pressure to give 6.3 g of a pale-orange powder.

This powder was dissolved in a mixture comprising 20 ml of methylene chloride and 20 ml of tetrahydrofuran, and the obtained solution was dropwise added to a sodium methoxide solution (prepared by adding 6.6 ml of a 28% solution of sodium methoxide in methanol to 40 ml of methanol) at –35° C.

The obtained solution was dropwise added at –35° C. to a separately prepared mixture comprising 35 ml of concentrated sulfuric acid and 100 ml of methanol. The obtained mixture was stirred at room temperature for 30 minutes and poured into a cool saturated aqueous solution of sodium hydrogencarbonate. The obtained mixture was extracted with ethyl acetate. The organic phase was washed with water, dried over anhydrous magnesium sulfate and concentrated under reduced pressure. 6.2 g of the title compound was obtained as a light-brown powder in a crude state. This powder was used in the subsequent reaction without being further purified.

4-[4,5,7,8,9,10-Hexahydro-7,7,10,10-tetramethyl-1(3-pyridylmethyl)anthra[1,2-d]pyrrol-3-yl]benzoic acid

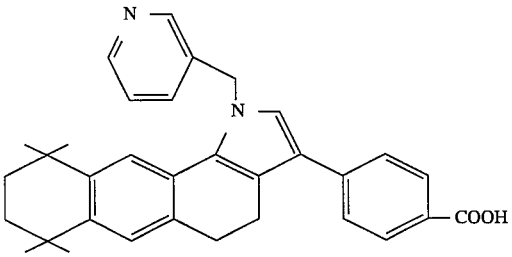

A mixture comprising 0.5 g of methyl 4-[1-(3,4,5,6,7,8-hexahydro-5,5,8,8-tetramethyl-1(2H)-anthracenon-2-yl)-2,2-dimethoxyethyl]benzoate and 0.14 g of 3-aminomethylpyridine was added to 10 ml of acetic acid. The resulting mixture was heated to 100° C., maintained at that temperature for 30 minutes, cooled to room temperature by allowing to stand, and poured into a saturated aqueous solution of sodium hydrogencarbonate. The obtained mixture was extracted with ethyl acetate. The organic phase was washed with a saturated aqueous solution of common salt, dried over anhydrous magnesium sulfate and concentrated under reduced pressure. The obtained solid was washed with diisopropyl ether to give 0.34 g of a waxy-white solid.

This solid was dissolved in a mixture comprising 10 ml of methanol and 20 ml of tetrahydrofuran, followed by the addition thereto of 5 ml of a 5N aqueous solution of sodium hydroxide. The obtained mixture was heated under reflux for 30 minutes and cooled to room temperature by allowing to stand, followed by the addition thereto of 30 ml of water. The pH of the resulting mixture was adjusted to 4 with dilute hydrochloric acid to precipitate a solid. This solid was recovered by filtration and washed with water. 0.25 g of the title compound was obtained as a waxy-white solid.

m.p.; 282° C. (dec.) $^1$H-NMR (400 MHz, DMSO-$d_6$) δ (ppm); 0.91(s, 6H), 1.17(s, 6H), 1.50(s, 4H), 2.68–2.85(m, 4H), 5.58(s, 2H), 6.90(s, 1H), 7.15(s, 1H), 7.34–7.43(m, 3H), 7.53(d, J=8.4 Hz, 2H), 7.92(d, J=8.4 Hz, 2H), 8.37(brs, 1H), 8.46(brs, 1H)

The compounds of Examples 17 to 48, of which structural formulas or the like will be described in Tables 5 to 14, were prepared in the same manner as that of the Example 16.

TABLE 5

| Ex. | structural formula | $^1$H-NMR(400MHz, DMSO-d6)δ | m.p. (C.°) |
|---|---|---|---|
| 17 | 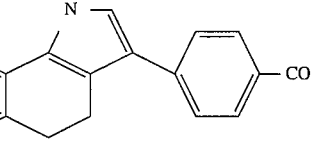 | 1.22(s, 6H), 1.25(s, 6H), 1.61(s, 4H) 2.73(s, 4H), 3.90(s, 3H), 7.20(s, 1H) 7.21(s, 1H), 7.40(s, 1H), 7.47(d, J=8.4Hz, 2H), 7.90(d, J=8.4Hz, 2H) | 291 (dec.) |
| 18 | 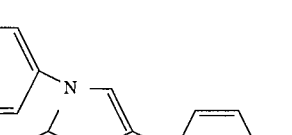 | 0.76(s, 6H), 1.18(s, 6H), 1.43–1.56 (m, 4H), 2.84(brs, 4H), 6.30(s, 1H), 7.16(s, 1H), 7.39(s, 1H), 7.43–7.56 (m, 5H), 7.58(d, J=8.4Hz, 2H), 7.92(d, J=8.4Hz, 2H) | 217–218 |
| 19 | 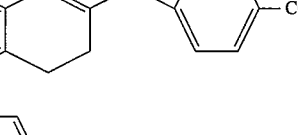 | 0.78(s, 6H), 1.18(s, 6H), 1.42–1.56 (m, 4H), 2.77–2.92(m, 4H), 6.25(s, 1H), 7.19(s, 1H), 7.46(s, 1H) 7.55–7.65(m, 3H), 7.88–7.98 (m, 3H), 8.63–8.74(m, 2H) | 226–227 |
| 20 | 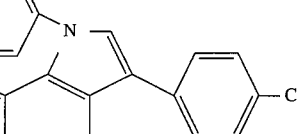 | 0.91(s, 6H), 1.20(s, 6H), 1.45–1.58 (m, 4H), 2.82(brs, 4H), 6.38(s, 1H), 7.20(s, 1H), 7.58(s, 1H), 7.62(d, J=8.4Hz, 2H), 7.83(d, J=3.4Hz, 1H), 7.90(d, J=3.4Hz, 1H), 7.95(d, J=8.4Hz, 2H) | 251–254 |

TABLE 6

| Ex. | structural formula | ¹H-NMR(400MHz, DMSO-d6)δ | m.p. (C.°) |
|---|---|---|---|
| 21 | | 1.21(s, 6H), 1.28(s, 6H), 1.62(s, 4H), 2.72(s, 4H), 3.61(t, J=2.5Hz, 1H), 5.04(d, J=2.5Hz, 2H), 7.18(s, 1H), 7.24(s, 1H), 7.42(d, J=8.4Hz, 2H), 7.60(s, 1H), 7.90(d, J=8.4Hz, 2H) | 217~219 |
| 22 | | 0.84(t, J=6.5Hz, 3H), 1.21(s, 6H), 1.24(s, 6H), 1.27~1.40(m, 4H), 1.62(s, 4H), 1.73~1.86(m, 2H), 2.73(s, 4H), 4.19(t, J=6.5Hz, 2H), 7.19(s, 1H), 7.24(s, 1H), 7.25(s, 1H) 7.48(d, J=8.4Hz, 2H), 7.90(d, J=8.4Hz, 2H) | 236~238 |
| 23 | | 0.99~1.12(m, 4H), 1.24(s, 6H), 1.29(s, 6H), 1.63(s, 4H), 2.74(s, 4H) 3.70~3.78(m, 1H), 7.16(s, 1H), 7.22(s, 1H), 7.50(d, J=8.4Hz, 2H), 7.84(s, 1H), 7.89(d, J=8.4Hz, 2H) | 262 (dec.) |
| 24 | | 0.84(s, 6H), 1.18(s, 6H), 1.50(s, 4H) 2.68~2.88(m, 4H), 5.50(s, 2H), 6.90 (s, 1H), 7.02~7.42(m, 7H), 7.53(d, J=8.4Hz, 2H), 7.92(d, J=8.4Hz, 2H) | >295 |

TABLE 7

| Ex. | structural formula | ¹H-NMR(400MHz, DMSO-d6)δ | m.p. (C.°) |
|---|---|---|---|
| 25 | | 1.23(s, 12H), 1.61(s, 4H), 2.72(s, 4H), 3.04~3.13(m, 2H), 4.42~4.54(m, 2H), 7.12~7.36(m, 8H), 7.44(d, J=8.4Hz, 2H), 7.90(d, J=8.4Hz, 2H) | 255~256 |
| 26 | | 1.22(s, 6H), 1.30(s, 6H), 1.38~1.92 (m, 15H), 2.70(s, 4H), 4.07(s, 2H), 7.10(s, 1H), 7.17(s, 1H), 7.47(s, 1H) 7.50(d, J=8.4Hz, 2H), 7.91(d, J=8.4Hz, 2H). | 264~266 |

TABLE 7-continued

| Ex. | structural formula | $^1$H-NMR(400MHz, DMSO-d6)δ | m.p. (C.°) |
|---|---|---|---|
| 27 | (3-methoxyphenyl substituted tetrahydro-tetramethyl-naphtho-pyrrole with 4-COOH-phenyl) | 0.86(s, 6H), 1.18(s, 6H), 1.51(s, 4H) 2.69~2.85(m, 4H), 3.70(s, 3H) 5.46(s, 2H), 6.60(d, J=7.6Hz, 1H), 6.69(s, 1H), 6.83(dd, J=7.6, 2.0Hz, 1H), 6.90(s, 1H), 7.13(s, 1H), 7.26(t, J=7.6Hz, 1H), 7.36(s, 1H), 7.49(d, J=8.4Hz, 2H), 7.91(d, J=8.4Hz, 2H) | 259~261 |
| 28 | (pyridin-2-yl-methyl substituted) | 0.86(s, 6H), 1.18(s, 6H), 1.50(s, 4H) 2.66~2.85(m, 4H), 5.54(s, 2H), 6.87(d, J=8.0Hz, 1H), 6.94(s, 1H), 7.15(s, 1H), 7.28~7.34(m, 1H), 7.45(s, 1H), 7.53(d, J=8.4Hz, 2H), 7.77(t, J=8.0Hz, 1H), 7.93(d, J=8.4 Hz, 2H), 8.60~8.64(m, 1H) | 287 (dec.) |

TABLE 8

| Ex. | structural formula | $^1$H-NMR(400MHz, DMSO-d6)δ | m.p. (C.°) |
|---|---|---|---|
| 29 | (pyridin-4-yl-methyl substituted) | 0.83(s, 6H), 1.17(s, 6H), 1.48(s, 4H) 2.69~2.86(m, 4H), 5.56(s, 2H), 6.74(s, 1H), 7.06(brs, 2H), 7.15(s, 1H), 7.39(s, 1H), 7.53(d, J=8.4Hz, 2H), 7.93(d, J=8.4Hz, 2H), 8.54(brs, 2H) | 264~265 (dec.) |
| 30 | (2-methoxyethyl substituted) | 1.22(s, 6H), 1.26(s, 6H), 1.62(s, 4H) 2.72(s, 4H), 3.28(s, 3H), 3.77(t, J=6.5Hz, 2H), 4.36(t, J=6.5 Hz, 2H), 7.19(s, 1H), 7.26(s, 1H), 7.43(s, 1H), 7.48(d, J=8.4Hz, 2H), 7.90(d, J=8.4Hz, 2H) | 227 |

TABLE 9

| example No. | Structural formula | $^1$H-NMR(400MHz, DMSO-d$_6$)δ(ppm) | m.p. (°C.) |
|---|---|---|---|
| 31 | (pyrazin-2-yl substituted) | 0.84(s, 6H), 1.20(s, 6H), 1.47~1.59(m, 4H) 2.77~2.90(m, 4H), 6.21(s, 1H), 7.22(s, 1H) 7.56(d, J=8.4Hz, 2H), 7.64(s, 1H) 7.93(d, J=8.4Hz, 2H), 8.65(s, 1H), 8.72(s, 1H) 8.87(s, 1H) | 223 |

TABLE 9-continued

| example No. | Structural formula | ¹H-NMR(400MHz, DMSO-d₆)δ(ppm) | m.p. (°C.) |
|---|---|---|---|
| 32 | | 0.95(s, 6H), 1.23(s, 6H), 1.52~1.62(m, 4H) 2.72~2.86(m, 4H), 6.51(s, 1H), 7.18(s, 1H) 7.52(t, J=4.5Hz, 1H), 7.58(d, J=8.4Hz, 2H) 7.77(s, 1H), 7.92(d, J=8.4Hz, 2H) 8.87(d, J=4.5Hz, 2H) | 226~227 |
| 33 | | 0.77(s, 6H), 1.21(s, 6H), 1.42~1.57(m, 4H) 2.75~2.92(m, 4H), 6.70(s, 1H), 7.22(s, 1H) 7.46~7.62(m, 4H), 7.70(s, 1H) 7.93(d, J=8.4Hz, 2H), 8.16(d, J=6.3Hz, 1H) | 200~202 |

TABLE 10

| example No. | Structural formula | ¹H-NMR(400MHz, DMSO-d₆)δ(ppm) | m.p. (°C.) |
|---|---|---|---|
| 34 | | 1.21(s, 6H), 1.24(s, 6H), 1.60(s, 4H), 2.72(s, 4H) 3.30(t, J=6.3Hz, 2H), 4.61(t, J=6.3Hz, 2H) 7.20(s, 1H), 7.22~7.31(m, 3H), 7.45(d, J=8.4Hz, 2H) 7.50(s, 1H), 7.69~7.76(m, 1H), 7.90(d, J=8.4Hz, 2H) 8.50~8.56(m, 1H) | 247~249 |
| 35 | | 0.91(s, 6H), 1.19(s, 6H), 1.52(brs, 4H), 2.82(s, 4H) 6.40(s, 1H), 6.47(s, 1H), 7.12(s, 1H), 7.30(s, 1H) 7.58(d, J=8.4Hz, 2H), 7.91(d, J=8.4Hz, 2H) 7.94(s, 1H), 13.12(brs, 1H) | 296 (dec.) |
| 36 | | 0.63(s, 3H), 1.07(s, 3H), 1.16(s, 6H) 1.43~1.57(m, 4H), 1.90(d, J=6.2Hz, 3H) 2.62~2.85(m, 4H), 5.83(q, J=6.2Hz, 1H), 6.84(s, 1H) 7.08~7.17(m, 3H), 7.21~7.28(m, 1H) 7.33~7.40(m, 2H), 7.52~7.62(m, 3H) 7.93(d, J=8.4Hz, 2H) | 270~272 |

TABLE 11

| example No. | Structural formula | ¹H-NMR(400MHz, DMSO-d₆)δ(ppm) | m.p. (°C.) |
|---|---|---|---|
| 37 | | 0.63(s,3H), 1.07(s, 3H), 1.16(s, 6H) 1.43~1.57(m, 4H), 1.90(d, J=6.2Hz, 3H) 2.62~2.85(m, 4H), 5.83(q, J=6.2Hz, 1H), 6.84(s, 1H) 7.08~7.17(m, 3H), 7.21~7.28(m, 1H) 7.33~7.40(m, 2H), 7.52~7.62(m, 3H) 7.93(d, J=8.4Hz, 2H) | 281~282 |
| 38 | | 1.13(s, 6H), 1.22(s, 6H), 1.60(s, 4H), 2.73(s, 4H) 5.43(s, 2H), 6.24(s, 1H), 6.45(s, 1H), 7.18(s, 1H) 7.28(s, 1H), 7.30(s, 1H), 7.46(d, J=8.4Hz, 2H) 7.68(s, 1H), 7.92(d, J=8.4Hz, 2H) | 262~264 (dec.) |
| 39 | | 0.93(s, 6H), 1.20(s, 6H), 1.55(brs, 4H), 2.80(s, 4H) 6.38(s, 1H), 7.16(s, 1H), 7.42(s, 1H), 7.58(d, J=8.4Hz, 2H), 7.92(d, J=8.4Hz, 2H) 8.76(brs, 1H) | 220~222 |

TABLE 12

| example No. | Structural formula | ¹H-NMR(400MHz, DMSO-d₆)δ(ppm) | m.p. (°C.) |
|---|---|---|---|
| 40 | | 0.82(s,6H), 1.19(s, 6H), 1.44~1.58(m, 4H) 2.74~2.87(m, 4H), 3.90(s, 3H), 6.30(s, 1H) 6.98(d, J=6.3Hz, 1H), 7.14(s, 1H), 7.28(s, 1H) 7.43(d, J=8.4Hz, 2H), 7.81(dd, J=6.3Hz, 1.2Hz, 1H) 8.29(d, J=1.2Hz, 1H) | 269 (dec.) |
| 41 | | 0.84(s, 6H), 1.20(s, 6H), 1.46~1.58(m, 4H) 2.78~2.90(m, 4H), 6.24(s, 1H), 7.21(s, 1H) 7.50(s, 1H), 7.58(d, J=8.4Hz, 2H) 7.72(d, J=6.3Hz, 1H), 7.93(d, J=8.4Hz, 2H) 8.00(dd, J=6.3Hz, 1.2Hz, 1H), 8.59(d, J=1.2Hz, 1H) | 291~292 |

TABLE 12-continued
| example No. | Structural formula | $^1$H-NMR(400MHz, DMSO-$d_6$)δ(ppm) | m.p. (°C.) |
|---|---|---|---|
| 42 | 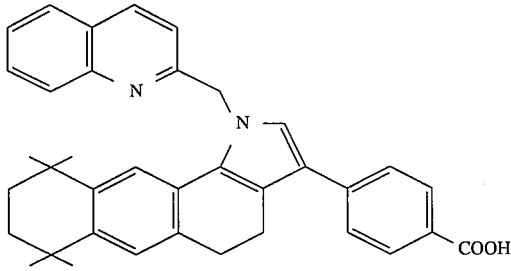 | 0.78(s, 6H), 1.13(s, 6H), 1.40~1.48(m, 4H) 2.71~2.85(m, 4H), 5.74(m, 4H), 7.06(s, 1H) 7.09(d, J=5.5Hz, 1H), 7.13(s, 1H), 7.55~7.60(m, 4H) 7.79(t, J=5.5Hz, 1H), 7.90~7.97(m, 3H) 8.03(d, J=5.5Hz, 1H), 8.35(d, J=5.5Hz, 1H) | 275~276 |
TABLE 13
| example No. | Structural formula | $^1$H-NMR(400MHz, DMSO-$d_6$)δ(ppm) | m.p. (°C.) |
|---|---|---|---|
| 43 | 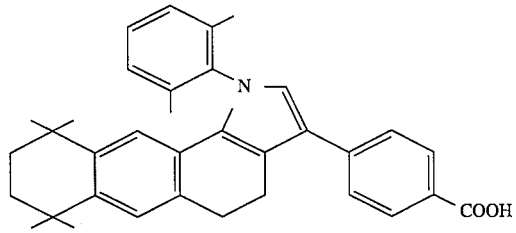 | 0.73(s, 6H), 1.17(s, 6H), 1.40~1.56(m, 4H) 1.98(s, 6H), 2.80~2.95(m, 4H), 6.18(s, 2H) 7.10(s, 1H), 7.17(s, 1H), 7.25~7.40(m, 3H) 7.58(d, J=8.4Hz, 2H), 7.90(d, J=8.4Hz, 2H) | 286~287 |
| 44 | 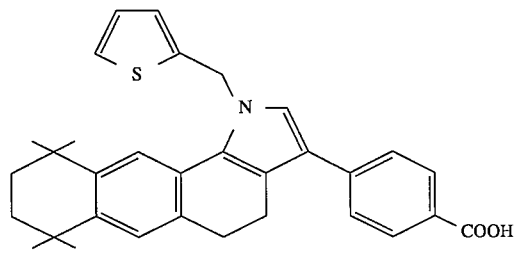 | 1.03(s, 6H), 1.20(s, 6H), 1.55(s, 4H) 2.70~2.82(m, 4H), 5.64(s, 2H), 6.87~6.92(m, 1H) 6.98~7.05(m, 1H), 7.10(s, 1H), 7.16(s, 1H) 7.18(s, 1H), 7.45~7.56(m, 3H), 7.92(d, J=8.4Hz, 2H) | 288 (dec.) |
| 45 | 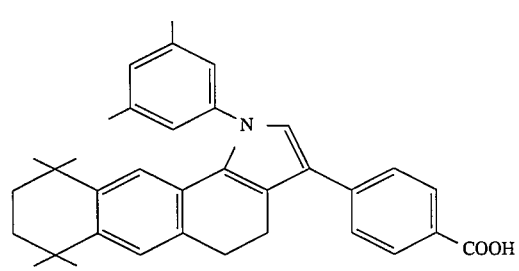 | 0.81(s, 6H), 1.20(s, 6H), 1.45~1.54(m, 4H) 2.30(s, 6H), 2.80~2.86(m, 4H), 6.40(s, 1H) 7.06(d, J=1.5Hz, 2H), 7.12(d, J=1.5Hz, 1H) 7.15(s, 1H), 7.34(s, 1H), 7.58(d, J=8.4Hz, 2H) 7.92(d, J=8.4Hz, 2H) | 278~280 |

TABLE 14

| example No. | Structural formula | $^1$H-NMR(400MHz, DMSO-d$_6$)δ(ppm) | m.p. (°C.) |
|---|---|---|---|
| 46 | (structure with pyrazinylmethyl group) | 0.94(s, 6H), 1.17(s, 6H), 1.52(s, 4H) 2.68–2.82(m, 4H), 5.66(s, 2H), 7.00(s, 1H) 7.15(s, 1H), 7.43(s, 1H), 7.51(d, J=8.4Hz, 2H) 7.92(d, J=8.4Hz, 2H), 8.28(s, 1H), 8.57(s, 1H) 8.67(s, 1H) | 287 (dec.) |
| 47 | (structure with isoquinolinyl group) | 0.50(s, 6H), 1.17(s, 6H), 1.33–1.52(m, 4H) 2.80–2.93(m, 4H), 6.23(s, 1H), 7.20(s, 1H) 7.50–7.60(m, 3H), 7.64–7.72(m, 1H) 7.80–7.85(m, 1H), 7.95(d, J=8.4Hz, 2H) 8.02–8.08(m, 1H), 8.10–8.16(m, 1H), 8.54(s, 1H) 9.00(s, 1H) | 284 (dec.) |
| 48 | (structure with 3-CF$_3$-benzyl group) | 0.82(s, 6H), 1.17(s, 6H), 1.43–1.55(m, 4H) 2.69–2.84(m, 4H), 5.62(s, 2H), 6.78(s, 1H) 7.15(s, 1H), 7.20–7.25(m, 1H), 7.43(s, 1H) 7.54(d, J=8.4Hz, 2H), 7.56–7.66(m, 3H) 7.92(d, J=8.4Hz, 2H), 12.77(brs, 1H) | 270–271 |

The compounds of Examples 49 to 55, of which structural formulas or the like will be described in Tables 15 and 16, were prepared from the ketone compounds prepared in Referential Examples 1, 3, 4, 5 and 6 in the same manner as that of the Example 16.

TABLE 15

| Ex. | structural formula | $^1$H-NMR(400MHz, DMSO-d6)δ | m.p. (C.°) |
|---|---|---|---|
| 49 | (structure with N-CH$_3$, S-containing ring) | 1.27(s, 6H), 1.84–1.92(m, 2H), 2.72(s, 4H), 2.96–3.03(m, 2H), 3.85(s, 3H), 7.12(s, 1H), 7.19(s, 1H) 7.30(s, 1H), 7.46(d, J=8.4Hz, 2H), 7.90(d, J=8.4Hz, 2H) | 267–268 |
| 50 | (structure with pyridylmethyl, S-containing ring) | 1.22(s, 6H), 1.78–1.84(m, 2H), 2.68–2.80(m, 4H), 2.88–2.94(m, 2H), 5.53(s, 2H), 6.82(s, 1H), 7.24(s, 1H), 7.30–7.44(m, 2H), 7.40(s, 1H), 7.50(d, J=8.4Hz, 2H), 7.91(d, J=8.4Hz, 2H), 8.35(brs, 1H) 8.45(brs, 1H) | 270–271 |

TABLE 15-continued

| Ex. | structural formula | $^1$H-NMR(400MHz, DMSO-d6)δ | m.p. (C.°) |
|---|---|---|---|
| 51 | (structure) | 0.89(s, 6H), 1.19(s, 6H), 1.53(brs, 4H), 4.02(s, 2H), 5.54(s, 2H), 6.99(s, 1H), 7.30(s, 1H), 7.42(brs, 2H), 7.45(s, 1H), 7.50(d, J=8.4Hz, 2H), 7.95 (d, J=8.4Hz, 2H), 8.37(brs, 1H), 8.50(brs, 1H) | 289~290 (dec.) |
| 52 | (structure) | 1.28(s, 6H), 1.76(t, J=7.0Hz, 2H), 2.71(brs, 4H), 3.88(s, 3H), 4.12(t, J=7.0Hz, 2H), 6.89(s, 1H), 7.17(s, 1H), 7.19(s, 1H), 7.43(d, J=8.4Hz, 2H), 7.88(d, J=8.4Hz, 2H) | 208~209 |

TABLE 16

| Ex. | structural formula | H-NMR(400MHz, DMSO-d6)δ | m.p. (C.°) |
|---|---|---|---|
| 53 | (structure) | 1.21(s, 6H), 1.68(t, J=7.0Hz, 2H), 2.68~2.80(m, 4H), 4.03(t, J=7.0Hz, 2H), 5.54(s, 2H), 6.54(s, 1H), 7.18(s, 1H), 7.34~7.43(m, 3H), 7.52(d, J=8.4Hz, 2H), 7.92(d, J=8.4Hz, 2H), 8.34(brs, 1H), 8.46(dd, J=4.4, 2.0Hz, 1H) | 205~206 (dec.) |
| 54 | (structure) | 0.89(s, 6H), 1.17(brs, 12H), 1.52(brs, 4H), 2.73(s, 2H), 5.60(s, 2H), 6.92(s, 1H), 7.20(s, 1H), 7.34(brs, 2H), 7.39(s, 1H), 7.49(d, J=8.4Hz, 2H), 7.92(d, J=8.4Hz, 2H), 8.33(brs, 1H), 8.44(brs, 1H) | 272~273 (dec.) |
| 55 | (structure) | 0.95(s, 6H), 1.16(s, 6H), 1.52(s, 4H), 5.36(s, 2H), 5.61(s, 2H), 6.80(s, 1H), 6.90(s, 1H), 7.40(brs, 2H), 7.43(d, J=8.4Hz, 2H), 7.58(s, 1H), 7.92(d, J=8.4HZ, 2H), 8.40(brs, 1H), 8.46(brs, 1H) | 271 (dec.) |

The compounds of Examples 56 to 62, of which structural formulas or the like will be described in Tables 17 to 19, were prepared from the ketone compound prepared in the similar manner as that of the Referential Example 3 in the same manner as that of the Example 16.

TABLE 17

| example No. | Structural formula | ¹H-NMR(400MHz, DMSO-d₆)δ(ppm) | m.p. (°C.) |
|---|---|---|---|
| 56 | | 2.48~2.50(m, 4H), 5.68(s, 2H), 7.28~7.40(m, 9H) 7.46~7.50(m, 2H), 7.55(d, J=8.4Hz, 2H) 7.95(d, J=8.4Hz, 2H), 8.42(d, J=2Hz, 1H) 8.47(dd, J=4.8Hz, 2Hz, 1H) | 275~277 |
| 57 | | 0.79(d, J=6.5Hz, 6H), 1.96(s, 6H), 2.81~2.94(m, 4H) 6.11(d, J=1.6Hz, 1H), 6.79(dd, J=7.6Hz, 1.6Hz, 1H) 7.08(d, J=7.6Hz, 1H), 7.17(s, 1H) 7.28(d, J=7.6Hz, 2H), 7.35(t, J=7.6Hz, 1H) 7.53(d, J=8.4Hz, 2H), 7.90(d, J=8.4Hz, 2H) | 153~154 |
| 58 | | 0.74(d, J=6.5Hz, 6H), 0.88(d, J=6.5Hz, 6H) 1.12(d, J=6.5Hz, 6H), 2.80~2.94(m, 4H) 3.24~3.38(m, 3H), 6.09(d, J=1.6Hz, 1H) 6.76(dd, J=7.6Hz, 1.6Hz, 1H), 7.06(d, J=7.6Hz, 1H) 7.25(s, 1H), 7.38(d, J=7.6Hz, 2H), 7.53(t, J=7.6Hz, 1H) 7.58(d, J=8.4Hz, 2H), 7.96(d, J=8.4Hz, 2H) | 215~217 |

TABLE 18

| example No. | Structural formula | ¹H-NMR(400MHz, DMSO-d₆)δ(ppm) | m.p. (°C.) |
|---|---|---|---|
| 59 | | 2.71~2.86(m, 4H), 5.48(s, 2H), 6.67(dd, J=8.0Hz, 2.4Hz, 1H), 6.85(d, J=8Hz, 2H) 6.89(d, J=2.4Hz, 1H), 7.08(t, J=8.0Hz, 1H) 7.21~7.27(m, 3H), 7.30(t, J=8.0Hz, 2H), 7.45(s, 1H) 7.54(d, J=8.4Hz, 2H), 7.93(d, J=8.4Hz, 2H) 8.15(brs, 1H), 8.39(dd, J=4.8Hz, 1.6Hz, 1H) | 141~143 |
| 60 | | 2.12(s, 3H), 2.21(s, 3H), 2.68(t, J=3Hz, 2H) 2.74(t, J=3.0Hz, 2H), 5.58(s, J=7.6Hz, 2H), 6.74(brs, 1H) 7.01(brs, 1H), 7.33(dd, J=7.6Hz, 5.2Hz, 1H), 7.43(s, 1H) 7.42~7.46(m, 1H), 7.53(d, J=8.4Hz, 2H) 7.93(d, J=8.4Hz, 2H), 8.38(d, J=2Hz, 1H) 8.43(dd, J=4.8Hz, 2Hz, 1H) | 176~179 |

TABLE 19

| example No. | Structural formula | ¹H-NMR(400MHz, DMSO-d₆)δ(ppm) | m.p. (°C.) |
|---|---|---|---|
| 61 | | 1.21(d, J=6.5Hz, 6H), 1.53(d, J=6.5Hz, 6H), 2.70(brs, 4H), 2.83~2.94(m, 1H), 4.82~4.92(m, 1H) 6.96(dd, J=7.6Hz, 1.2Hz, 1H), 7.19(d, J=7.6Hz, 1H) 7.22(brs, 1H), 7.48(s, 1H), 7.52(d, J=8.4Hz, 2H) 7.90(d, J=8.4Hz, 2H) | 199–201 |
| 62 | | 0.91(t, J=7.4Hz, 3H), 1.09(t, J=7.4Hz, 3H) 2.42(q, J=7.4Hz, 2H), 2.47(q, J=7.4Hz, 2H) 2.69~2.80(m, 4H), 5.60(s, 2H), 7.00(s, 1H), 7.02(s, 1H) 7.30~7.35(m, 1H), 7.37~7.44(m, 2H) 7.52(d, J=8.4Hz, 2H), 7.91(d, J=8.4Hz, 2H) 8.35~8.46(m, 2H) | 241–243 |

The compounds of Examples 63 to 73, of which structural formulas or the like will be described in Tables 20 to 23, were prepared from the ketone compounds prepared in Referential Example 8 and in the similar manner as that of the Referential Example 8 in the same manner as that of the Examples 1 or 16.

TABLE 20

| example No. | Structural formula | ¹H-NMR(400MHz, DMSO-d₆)δ(ppm) | m.p. (°C.) |
|---|---|---|---|
| 63 | | 1.02(d, J=6.5Hz, 6H), 1.10(d, J=6.5Hz, 6H) 2.78~2.93(m, 4H), 3.08~3.20(m, 1H), 4.16~4.27(m, 1H) 5.86(s, 2H), 6.72(s, 1H), 7.18(s, 1H), 7.34~7.46(m, 2H) 7.83(d, J=8.4Hz, 2H), 8.00(d, J=8.4Hz, 2H), 8.41(brs, 1H) 8.46~8.50(m, 1H) | 249–251 |
| 64 | | 0.96(d, J=6.5Hz, 6H), 1.07(d, J=6.5Hz, 6H) 2.68~2.82(m, 4H), 3.05~3.14(m, 1H), 3.98~4.07(m, 1H) 5.62(s, 2H), 6.55(s, 1H), 7.04(s, 1H), 7.35~7.39(m, 2H) 7.41(s, 1H), 7.52(d, J=8.4Hz, 2H), 7.91(d, J=8.4Hz, 2H) 8.37(brs, 1H), 8.46(brs, 1H) | 265–266 |

TABLE 20-continued

| example No. | Structural formula | $^1$H-NMR(400MHz, DMSO-$d_6$)δ(ppm) | m.p. (°C.) |
| --- | --- | --- | --- |
| 65 | | 1.07(d, J=6.5Hz, 6H), 1.11(t, J=6.7Hz, 3H) 2.68~2.81(m, 4H), 3.06~3.16(m, 1H), 3.60(q, J=6.7Hz, 2H), 5.62(s, 2H), 6.57(s, 1H) 7.03(s, 1H), 7.34~7.44(m, 3H), 7.53(d, J=8.4Hz, 2H) 7.93(d, J=8.4Hz, 2H), 8.40(brs, 1H), 8.44~8.50(m, 1H) 12.75(brs, 1H) | 258~259 |

TABLE 21

| example No. | Structural formula | $^1$H-NMR(400MHz, DMSO-$d^6$)δ(ppm) | m.p. (°C.) |
| --- | --- | --- | --- |
| 66 | | 1.10(d, J=6.5Hz, 6H), 1.35~1.60(m, 8H) 2.69~2.83(m, 4H), 3.02~3.11(m, 1H), 4.29~4.35(m, 1H) 5.62(s, 2H), 6.53(s, 1H), 7.04(s, 1H), 7.35~7.42(m, 3H) 7.54(d, J=8.4Hz, 2H), 7.93(d, J=8.4Hz, 2H), 8.40(s, 1H) 8.48(brs, 1H) | 277~280 |
| 67 | | 0.96(d, J=6.5Hz, 6H), 1.04(t, J=6.7Hz, 3H) 2.42(q, J=6.7Hz, 2H), 2.67~2.82(m, 4H) 4.00~4.08(m, 1H), 5.62(s, 2H), 6.57(s, 1H), 7.00(s, 1H) 7.38(brs, 2H), 7.40(s, 1H), 7.52(d, J=8.4Hz, 2H) 7.93(d, J=8.4Hz, 2H), 8.37(brs, 1H), 8.46(brs, 1H) | 255~257 |
| 68 | | 0.87(d, J=6.5Hz, 6H), 1.09(d, J=6.5Hz, 6H) 1.80~1.92(m, 1H), 2.64~2.82(m, 4H), 3.05~3.15(m, 1H) 3.17(d, J=6.5Hz, 2H), 5.60(s, 1H), 6.48(s, 1H) 7.03(s, 1H), 7.37(s, 1H), 7.37~7.52(m, 4H) 7.91(d, J=8.4Hz, 2H), 8.38(brs, 1H), 8.46(brs, 1H) | 240~241 |

TABLE 22

| example No. | Structural formula | $^1$H-NMR(400MHz, DMSO-d$_6$)δ(ppm) | m.p. (°C.) |
|---|---|---|---|
| 69 | | 1.00(d, J=6.5Hz, 6H), 2.67~2.83(m, 4H) 4.11~4.20(m, 1H), 5.64(s, 2H), 6.72(s, 1H), 7.28(s, 1H) 7.37(brs, 2H), 7.47(s, 1H), 7.52(d, J=8.4Hz, 2H) 7.93(d, J=8.4Hz, 2H), 8.38(brs, 1H), 8.46(brs, 1H) | 272~273 |
| 70 | | 0.89(d, J=6.5Hz, 6H), 2.76~2.88(m, 4H) 3.97~4.06(m, 1H), 5.68(s, 2H), 6.70(s, 1H), 7.20(s, 1H) 7.20~7.27(m, 1H), 7.33~7.50(m, 7H) 7.56(d, J=8.4Hz, 2H), 7.94(d, J=8.4Hz, 2H), 8.40(brs, 1H) 8.48(brs, 1H) | 275~278 |
| 71 | | 0.97(d, J=6.5Hz, 6H), 2.01(s, 3H), 2.62~2.85(m, 4H) 4.00~4.12(m, 1H), 5.62(s, 2H), 6.57(s, 1H), 6.99(s, 1H) 7.37(brs, 2H), 7.40(s, 1H), 7.52(d, J=8.4Hz, 2H) 7.92(d, J=8.4Hz, 2H), 8.37(brs, 1H), 8.46(brs, 1H) | 261~263 |

TABLE 23

| example No. | Structural formula | $^1$H-NMR(400MHz, DMSO-d$_6$)δ(ppm) | m.p. (°C.) |
|---|---|---|---|
| 72 | | 1.03(t, J=6.8Hz, 3H), 1.12(t, J=6.8Hz, 3H)2.44(q, J=6.8Hz, 2H), 2.64~2.81(m, 4H)3.61(q, J=6.8Hz, 2H), 5.61(s, 2H), 6.57(s, 1H) 6.98(s, 1H), 7.32~7.42(m, 3H), 7.52(d, J=8.4Hz, 2H) 7.92(d, J=8.4Hz, 2H), 8.40(brs, 1H), 8.47(brs, 1H) | 271~272 |

TABLE 23-continued

| example No. | Structural formula | ¹H-NMR(400MHz, DMSO-d₆)δ(ppm) | m.p. (°C.) |
|---|---|---|---|
| 73 | (pyridin-3-ylmethyl-substituted pentyloxy-isopropyl-dihydrobenzo-indole with 4-carboxyphenyl) | 0.86(t, J=7.6Hz, 3H), 1.10(d, J=6.5Hz, 6H)1.20~1.34(m, 4H), 1.48~1.58(m, 2H), 2.68~2.82(m, 4H)3.06~3.16(m, 1H), 3.48(t, J=6.5Hz, 2H), 5.62(s, 2H)6.53(s, 1H), 7.04(s, 1H), 7.32~7.45(m, 3H)7.53(d, J=8.4Hz, 2H), 7.92(d, J=8.4Hz, 2H), 8.40(s, 1H) | 238~240 |

The compounds of Examples 74 to 80, of which structural formulas or the like will be described in Tables 24 and 25, were prepared from the ketone compounds prepared in Referential Examples 2, 9 and 10 and in the similar manner as that of the Referential Examples 2, 9 or 10 in the same manner as that of the Examples 1, 6, 7 or 16.

TABLE 24

| example No. | Structural formula | ¹H-NMR(400MHz, DMSO-d₆)δ(ppm) | m.p. (°C.) |
|---|---|---|---|
| 74 | (dimethylpyrrolyl-N-methylpyrazolyl-tetrahydronaphthalene with 4-carboxyphenyl) | 2.03(s, 6H), 2.88–3.00(m, 4H), 4.16(s, 3H) 5.80(s, 2H), 7.15(dd, J=8.8Hz, 2.5Hz, 1H) 7.49~7.53(m, 2H), 7.79(d, J=8.4Hz, 2H) 8.00(d, J=8.4Hz, 2H) | 199~200 |
| 75 | (dimethylpyrrolyl-NH-pyrazolyl-tetrahydronaphthalene with 4-carboxyphenyl) | 2.00(s, 6H), 3.01(brs, 4H), 5.80(s, 2H) 7.10(dd, J=8.8Hz, 2.5Hz, 1H), 7.44(d, J=8.8Hz, 1H)7.53(d, J=2.5Hz, 1H), 7.80(d, J=8.4Hz, 2H) 8.02(d, J=8.4Hz, 2H) | 250 (dec.) |
| 76 | (dimethylpyrrolyl-pyridin-3-ylmethyl-pyrazolyl-tetrahydronaphthalene with 4-carboxyphenyl) | 1.80(s, 6H), 2.98(s, 4H), 5.73(s, 2H), 5.85(s, 2H) 7.10(dd, J=8.8Hz, 2.5Hz, 1H), 7.28~7.40(m, 3H) 7.48(d, J=8.8Hz, 1H), 7.83(d, J=8.4Hz, 2H) 8.02(d, J=8.4Hz, 2H), 8.30(brs, 1H), 8.43(brs, 1H) | 223 (dec.) |

TABLE 24-continued

| example No. | Structural formula | ¹H-NMR(400MHz, DMSO-d$_6$)δ(ppm) | m.p. (°C.) |
| --- | --- | --- | --- |
| 77 | (structure) | 1.29(s, 12H), 1.85(s, 2H), 2.72~2.83(m, 4H) 5.53(s, 2H), 6.85(s, 1H), 7.30~7.38(m, 2H) 7.40~7.47(m, 2H), 7.52(d, J=8.4Hz, 2H) 7.92(d, J=8.4Hz, 2H), 8.35(brs, 1H), 8.44(brs, 1H)12.82(brs, 1H) | 263~264 |

TABLE 25

| example No. | Structural formula | ¹H-NMR(400MHz, DMSO-d$_6$)δ(ppm) | m.p. (°C.) |
| --- | --- | --- | --- |
| 78 | (structure) | 0.86(brs, 3H), 1.19(d, J=6.7Hz, 6H), 1.40(brs, 3H) 2.40~2.89(m, 5H), 3.20~3.30(m, 1H), 5.00~5.29(m, 2H)7.03(s, 1H), 7.12(s, 1H), 7.18~7.29(m, 2H), 7.31(s, 1H)7.48(d, J=8.4Hz, 2H), 7.89(d, J=8.4Hz, 2H), 8.13(s, 1H)8.38(brs, 1H) | 145~147 |
| 79 | (structure) | 1.06(s, 6H), 1.22(s, 6H), 1.58(brs, 4H) 2.10~2.21(m, 2H), 2.28~2.50(m, 4H), 5.33(s, 2H) 7.04(s, 1H), 7.22(s, 1H), 7.26(s, 1H) 7.29~7.35(m, 2H), 7.48(d, J=8.4Hz, 2H) 7.92(d, J=8.4Hz, 2H), 8.21(brs, 1H), 8.41(brs, 1H) | 280~281 |
| 80 | (structure) | 0.88(s, 6H), 1.18(s, 6H), 1.51(brs, 4H), 2.80(s, 4H) 5.58(s, 2H), 6.89(s, 1H), 7.10(d, J=3.8Hz, 1H) 7.15(s, 1H), 7.36(brs, 2H), 7.48(s, 1H) 7.64(d, J=3.8Hz, 1H), 8.37(brs, 1H), 8.48(brs, 1H) | 289 (dec.) |

The important intermediates of Examples 81 to 104, of which structural formulas or the like will be described in Tables 26 to 33, were prepared from the ketone compounds prepared in Referential Examples and in the similar manner as that of the Example 16.

TABLE 26

| example No. | Structural formula | ¹H-NMR(400MHz, CDCl₃)δ(ppm) | m.p. (°C.) |
|---|---|---|---|
| 81 | (ethyl, ethyl substituted tetralone benzylidene with CO₂CH₃) | 1.25(t, J=7.5Hz, 3H), 1.27(t, J=7.5Hz, 3H), 2.69(q, J=7.5Hz, 4H), 2.92(t, J=6.4Hz, 2H)3.08(t, J=6.4Hz, 2H), 3.93(s, 3H), 7.04(s, 1H)7.49(d, J=8.4Hz, 2H), 7.81(s, 1H), 7.95(s, 1H) 8.06(d, J=8.4Hz, 2H) | 104.5~105 |
| 82 | (isopropoxy, isopropyl substituted tetralone benzylidene with CO₂CH₃) | 1.22(d, J=6.5Hz, 6H), 1.37(d, J=6.5Hz, 6H)2.88(t, J=6.4Hz, 2H), 3.09(t, J=6.4Hz, 2H)3.32~3.40(m, 1H), 3.94(s, 3H), 4.67~4.47(m, 1H)7.06(s, 1H), 7.48(d, J=8.4Hz, 2H), 7.56(s, 1H)7.80(s, 1H), 8.07(d, J=8.4Hz, 2H) | 102~102.5 |
| 83 | (S-tBu substituted tetralone benzylidene with CO₂CH₃) | 1.42(s, 12H), 1.96(s, 2H), 2.90(t, J=6.4Hz, 2H)3.08(t, J=6.4Hz, 2H), 3.93(s, 3H), 7.26(s, 1H)7.48(d, J=8.4Hz, 2H), 7.81(s, 1H), 7.90(s, 1H)8.07(d, J=8.4Hz, 2H) | 111~112 |

TABLE 27

| example No. | Structural formula | ¹H-NMR(400MHz, CDCl₃)δ(ppm) | m.p. (°C.) |
|---|---|---|---|
| 84 | (cyclopentyloxy, isopropyl substituted tetralone benzylidene with CO₂CH₃) | 1.20(d, J=6.5Hz, 6H), 1.60~2.00(m, 8H)2.89(d, J=6.4Hz, 2H), 3.07(d, J=6.4Hz, 2H)3.25~3.35(m, 1H), 3.93(s, 3H), 4.88~4.95(m, 1H)7.04(s, 1H), 7.48(d, J=8.4Hz, 2H), 7.54(s, 1H) 7.80(s, 1H), 8.06(d, J=8.4Hz, 2H) | 108.5~109 |
| 85 | (isopropyl substituted tetralone benzylidene with CO₂CH₃) | 1.24(d, J=6.5Hz, 6H), 2.92(d, J=6.4Hz, 2H)3.12(t, J=6.4Hz, 2H), 3.49(m, 1H), 3.94(s, 3H)7.19(d, J=7.6Hz, 1H), 7.49(d, J=8.4Hz, 2H), 7.85(brs, 1H)8.01(d, J=2.0Hz, 1H), 8.08(d, J=8.4Hz, 2H) | 101~102 |
| 86 | (O₂S-tBu substituted tetralone benzylidene with CO₂CH₃) | 1.48(s, 12H), 2.33(s, 2H), 3.00(t, J=6.4Hz, 2H)3.13(t, J=6.4Hz, 2H), 3.94(s, 3H), 7.30(s, 1H)7.48(d, J=8.4Hz, 2H), 7.88(s, 1H), 8.08(d, J=8.4Hz, 2H)8.76(s, 1H) | 221~222 |

TABLE 28

| example No. | Structural formula | $^1$H-NMR(400MHz, CDCl$_3$)δ(ppm) | m.p. (°C.) |
|---|---|---|---|
| 87 | (pentyloxy, isopropyl-substituted tetralone with benzylidene-CO$_2$CH$_3$) | 0.93(t, J=6.5Hz, 3H), 1.23(d, J=6.5Hz, 6H)1.35~1.53(m, 2H), 1.78~1.87(m, 2H)2.89(t, J=6.4Hz, 2H), 3.08(t, J=6.4Hz, 2H) 3.32~3.43(m, 1H), 3.92(s, 3H), 4.04(t, J=6.5Hz, 2H)7.04(s, 1H), 7.48(d, J=8.4Hz, 2H)7.53(s, 1H) 7.80(s, 1H), 8.07(d, J=8.4Hz, 2H) | 120.5~121 |
| 88 | (tetramethyl-tetrahydro-tetralone with thiophene-CO$_2$CH$_3$ benzylidene) | 1.31(s, 6H), 1.32(s, 6H), 1.70(s, 4H) 2.98(t, J=6.4Hz, 2H), 3.20(t, J=6.4Hz, 2H), 3.91(s, 3H)7.18(s, 1H), 7.32(d, J=4.0Hz, 1H), 7.77(d, J=4.0Hz, 1H)7.92(s, 1H), 8.06(s, 1H) | 170~170.5 |
| 89 | (isopropoxy, ethyl-substituted tetralone with benzylidene-CO$_2$CH$_3$) | 1.21(t, J=6.5Hz, 3H), 1.36(d, J=6.5Hz, 6H)2.65(q, J=6.5Hz, 2H), 2.87(t, J=6.4Hz, 2H)3.08(t, J=6.4Hz, 2H), 3.39(s, 3H), 4.63~4.74(m, 1H)7.02(s, 1H), 7.48(d, J=8.4Hz, 2H), 7.56(s, 1H) 7.80(s, 1H), 8.05(d, J=8.4Hz, 2H) | 103 |

TABLE 29

| example No | Structural formula | $^1$H-NMR(400MHz, CDCl$_3$)δ(ppm) | m.p. (°C.) |
|---|---|---|---|
| 90 | (ethoxy, isopropyl-substituted tetralone with benzylidene-CO$_2$CH$_3$) | 1.23(d, J=6.8Hz, 6H), 1.45(t, J=7.0Hz, 3H) 2.90(t, J=6.4Hz, 2H), 3.07(t, J=6.4Hz, 2H) 3.32~3.42(m, 1H), 3.93(s, 3H), 4.12(q, J=7.0Hz, 2H)7.05(s, 1H), 7.48(d, J=8.4Hz, 2H), 7.54(s, 1H)7.80(s, 1H), 8.07(d, J=8.4Hz, 2H) | 157 |
| 91 | (ethoxy, ethyl-substituted tetralone with benzylidene-CO$_2$CH$_3$) | 1.21(t, J=6.5Hz, 3H), 1.43(t, J=6.5Hz, 3H) 2.69(q, J=6.5Hz, 2H), 2.89(t, J=6.4Hz, 2H) 3.08(t, J=6.4Hz, 2H), 3.94(s, 3H), 4.12(q, J=6.5Hz, 2H)7.02(s, 1H), 7.48(d, J=8.4Hz, 2H), 7.53(s, 1H)7.80(s, 1H), 8.05(d, J=8.4Hz, 2H) | 127~128 |
| 92 | (methoxy, diisopropyl-substituted tetralone with benzylidene-CO$_2$CH$_3$) | 1.22(d, J=6.5Hz, 6H), 1.38(d, J=6.5Hz, 2H) 2.75(d, J=6.4Hz, 2H), 2.97(d, J=6.4Hz, 2H) 3.26~3.35(m, 1H), 3.69~3.78(m, 1H), 3.76(s, 3H)3.90(s, 3H), 6.95(s, 1H), 7.46(d, J=8.4Hz, 2)7.73(s, 1H), 8.03(d, J=8.4Hz, 2H) | 121~122 |

TABLE 30

| example No. | Structural formula | ¹H-NMR(400MHz, CDCl₃)δ(ppm) | m.p. (°C.) |
|---|---|---|---|
| 93 | | 1.27(d, J=6.7Hz, 6H), 1.29(d, J=6.7Hz, 6H) 2.28~2.95(m, 3H), 3.02(t, J=6.4Hz, 2H), 3.90(s, 3H)3.92~4.02(m, 1H), 6.93(d, J=2.4Hz, 1H)7.22(d, J=2.4Hz, 1H), 7.50(d, J=8.4Hz, 2H), 7.82(s, 1H)8.06(d, J=8.4Hz, 2H) | 120~120.5 |
| 94 | | 1.41(d, J=6.5Hz, 6H), 2.86(t, J=6.4Hz, 2H) 3.08(t, J=6.4Hz, 2H), 3.94(s, 3H), 4.65~4.73(m, 1H), 7.28(s, 1H), 7.48(d, J=8.4Hz, 2H), 7.66(s, 1H)7.82(s, 1H), 8.06(d, J=8.4Hz, 2H) | 150~151 |
| 95 | | 1.31(d, J=6.5Hz, 6H), 2.93(t, J=6.4Hz, 2H) 3.13(t, J=6.4Hz, 2H), 3.94(s, 3H), 4.60~4.67 (m, 1H)7.21(s, 1H), 7.31~7.45(m, 3H), 7.50(d, J=8.4Hz, 2H)7.55~7.60(m, 2H), 7.70(s, 1H), 7.85(s, 1H)8.08(d, J=8.4Hz, 2H) | 149~149.5 |

TABLE 31

| example No. | Structural formula | ¹H-NMR(400MHz, CDCl₃)δ(ppm) | m.p. (°C.) |
|---|---|---|---|
| 96 | | 1.36(d, J=6.5Hz, 6H), 2.25(s, 3H), 2.86(t, J=6.4Hz, 2H)3.07(t, J=6.4Hz, 2H), 3.94(s, 3H), 4.63~4.71(m, 1H), 7.03(s, 1H), 7.48(d, J=8.4Hz, 2H), 7.56(s, 1H)7.80(s, 1H), 8.06(d, J=8.4Hz, 2H) | 141~141.5 |
| 97 | | 3.00(t, J=6.4Hz, 2H), 3.15(t, J=6.4Hz, 2H), 3.96(s, 3H)7.33~7.40(m, 2H), 7.49~7.54(m, 2H)7.50(d, J=8.4Hz, 2H), 7.66(dt, J=7.2Hz, 1.2Hz, 2H)7.76(dd, J=8.0Hz, 2Hz, 1H), 7.89(brs, 1H) 8.09(d, J=8.4Hz, 2H), 8.38(t, J=2Hz, 1H) | 187~188.5 |
| 98 | | 2.94(t, J=6.4Hz, 2H), 3.12(t, J=6.4Hz, 2H), 3.94(s, 3H)7.02(dd, J=7.6Hz, 0.8Hz, 2H), 7.13(tt, J=7.6Hz, 0.8Hz, 1H)7.20(dd, J=7.6Hz, 2.0Hz, 1H), 7.24(s, 1H)7.35(t, J=7.6Hz, 1H), 7.48(d, J=8.4Hz, 2H)7.73(d, J=2.0Hz, 1H), 7.83(brs, 1H), 8.08(d, J=8.4Hz, 2H) | 111~112 |

TABLE 32

| example No. | Structural formula | ¹H-NMR(400MHz, CDCl₃)δ(ppm) | m.p. (°C.) |
|---|---|---|---|
| 99 | (structure with methyl substituents, tetralone, benzylidene-CO₂CH₃) | 2.30(s, 3H), 2.35(s, 3H), 2.84(t, J=6.4Hz, 2H) 3.10(t, J=6.4Hz, 2H), 3.94(s, 3H), 7.21(brs, 1H) 7.48(d, J=8.4Hz, 2H), 7.79(brs, 1H), 7.83(brs, 1H)8.07(d, J=8.4Hz, 2H) | 162~164 |
| 100 | (structure with S-containing ring, tetralone, benzylidene-CO₂CH₃) | 1.35(s, 6H), 1.97(t, J=6.8Hz, 2H), 2.88(d, J=6.4Hz, 2H)3.01~3.12(m, 4H), 3.94(s, 3H), 7.23(s, 1H)7.48(d, J=8.4Hz, 2H), 7.81(s, 1H), 7.86(s, 1H)8.08(d, J=8.4Hz, 2H) | 173~173.5 |
| 101 | (structure with gem-dimethyl groups, S-containing ring, tetralone, benzylidene-CO₂CH₃) | 1.29(s, 6H), 1.33(s, 6H), 1.71(s, 4H), 3.95(s, 3H) 4.04(s, 2H), 7.23(s, 1H), 7.46(d, J=8.4Hz, 2H) 7.72(s, 1H), 8.09(d, J=8.4Hz, 2H), 8.18(s, 1H) | 171~172 |

TABLE 33

| example No. | Structural formula | ¹H-NMR(400MHz, CDCl₃)δ(ppm) | m.p. (°C.) |
|---|---|---|---|
| 102 | (structure with gem-dimethyl groups, O-containing ring, tetralone, benzylidene-CO₂CH₃) | 1.28(s, 6H), 1.32(s, 6H), 1.70(s, 4H), 3.94(s, 3H) 5.25(s, 2H), 6.89(s, 1H), 7.36(d, J=8.4Hz, 2H) 7.83(s, 1H), 7.97(s, 1H), 8.08(d, J=8.4Hz, 2H) | 170~171 |
| 103 | (structure with tetramethyl groups, anthracenone, benzylidene-CO₂CH₃) | 1.30(s, 6H), 1.31(s, 6H), 1.32(s, 6H), 1.70(s, 4H) 2.92(s, 2H), 3.94(s, 3H), 7.32(s, 1H) 7.47(d, J=8.4Hz, 2H), 7.90(s, 1H), 8.04~8.12(m, 3H) | 210~212 |
| 104 | (structure with gem-dimethyl, O-containing ring, tetralone, benzylidene-CO₂CH₃) | 1.35(s, 6H), 1.86(t, J=6.0Hz, 2H), 2.88(t, J=6.4Hz, 2H)3.08(t, J=6.4Hz, 2H), 3.93(s, 3H), 4.22(t, J=6.0Hz, 2H)7.13(brs, 1H), 7.47(d, J=8.4Hz, 2H), 7.53(brs, 1H)7.81(brs, 1H), 8.07(d, J=8.4Hz, 2H) | 132~133 |

EXAMPLE 105

4-(4,5,7,8,9,10-Hexahydro-7,7,10,10-tetramethylanthra-[1,2-b]pyrrol-3-yl)benzoic acid

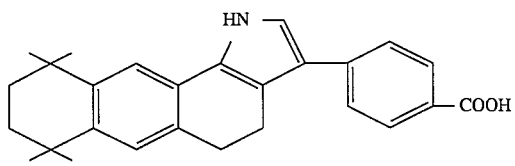

1.0 g of methyl 4-[1-(3,4,5,6,7,8-hexahydro-5,5,8,8-tetramethyl-1(2H)-anthracenon-2-yl)-2,2-dimethoxyethyl] benzoate was dissolved in 20 ml of glacial acetic acid, followed by the addition thereto of 0.8 g of ammonium acetate. The obtained mixture was stirred under heating at 100° C. for 4 hours and cooled to room temperature by allowing to stand, followed by the addition thereto of water. The precipitated solid was recovered by filtration and washed with water and methanol successively.

The resulting solid was dissolved in a mixture comprising 10 ml of methanol and 10 ml of tetrahydrofuran, followed by the addition thereto of 10 ml of a 5N aqueous solution of sodium hydroxide. The obtained mixture was heated under reflux for 30 minutes and cooled to room temperature by allowing to stand, followed by the addition thereto of 20 ml of water. The pH of the resulting mixture was adjusted to 4 with dilute hydrochloric acid to precipitate a pale-yellow solid. This solid was recovered by filtration and washed with water. 0.5 g of the title compound was obtained.

m.p.; 268°–270° C. ¹H-NMR (400 MHz, DMSO-d₆) δ(ppm); 1.20(s, 6H), 1.24(s, 6H), 1.60(s, 4H), 2.80(s, 4H), 7.10(s, 1H), 7.22(s, 1H), 7.44(s, 1H), 7.52(d, J=8.4 Hz, 2H), 7.91(d, J=8.4 Hz, 2H), 11.50 (brs, 1H)

EXAMPLE 106

4-(4,5,7,8,9,10-Hexahydro-7,7,10,10-tetramethylan-thra-[1,2-b]furan-3-yl)benzoic acid

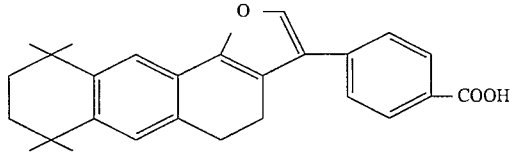

0.6 g of methyl 4-[1-(3,4,5,6,7,8-hexahydro-5,5,8,8-tetramethyl-1(2H)-anthracenon-2-yl)-2,2-dimethoxyethyl]benzoate was added to 10 ml of concentrated sulfuric acid. The obtained mixture was stirred at room temperature for 20 hours and poured onto ice. The obtained mixture was extracted with ethyl acetate. The organic phase was washed with water, a saturated aqueous solution of sodium hydrogencarbonate and a saturated aqueous solution of common salt, dried over anhydrous magnesium sulfate and concentrated under reduced pressure. The residue was purified by silica gel column chromatography (developer: 5% ethyl acetate/n-hexane). 0.1 g of a white solid was obtained.

This solid was dissolved in a mixture comprising 5 ml of methanol and 5 ml of tetrahydrofuran, followed by the addition thereto of 5 ml of a 5N aqueous solution of sodium hydroxide. The obtained mixture was heated under reflux for 30 minutes and cooled to room temperature by allowing to stand, followed by the addition thereto of 20 ml of water. The resulting mixture was acidified with dilute hydrochloric acid to precipitate a white solid. This solid was recovered by filtration and washed with water. 0.09 g of the title compound was obtained.

m.p.; 248° C. (dec.) ¹H-NMR (400 MHz, DMSO-d₆) δ(ppm); 1.23(s, 6H), 1.25(s, 6H), 1.62(s, 4H), 2.84–2.95(m, 4H), 7.22(s, 1H), 7.32(s, 1H), 7.62(d, J=8.4 Hz, 2H), 7.96(d, J=8.4 Hz, 2H), 8.14(s, 1H)

EXAMPLE 107

4-(4,5,7,8,9,10-Hexahydro-7,7,10,10-tetramethylan-thra-[1,2-b]thiophen-3-yl)benzoic acid

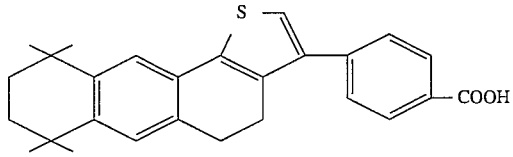

1.0 g of methyl 4-[1-(3,4,5,6,7,8-hexahydro-5,5,8,8-tetramethyl-1(2H)-anthracenon-2-yl)-2,2-dimethoxyethyl]benzoate was dissolved in 50 ml of xylene, followed by the addition thereto of 0.6 g of phosphorus pentasulfide. The obtained mixture was heated under reflux for 20 minutes, cooled to room temperature by allowing to stand, and concentrated under reduced pressure. The residue was purified by silica gel column chromatography (developer: 3% ethyl acetate/n-hexane) to give 0.25 g of a yellow solid.

This solid was dissolved in a mixture comprising 10 ml of methanol and 10 ml of tetrahydrofuran, followed by the addition thereto of 10 ml of a 5N aqueous solution of sodium hydroxide. The obtained mixture was heated under reflux for 30 minutes and cooled to room temperature by allowing to stand, followed by the addition thereto of 10 ml of water. The obtained mixture was acidified with dilute hydrochloric acid to precipitate a pale-yellow solid. This solid was recovered by filtration and washed with water. 0.22 g of the title compound was obtained.

m.p.; 261°–262° C. ¹H-NMR (400 MHz, DMSO-d₆) δ(ppm); 1.24(s, 6H), 1.26(s, 6H), 1.63(s, 4H), 2.75–2.84(m, 4H), 7.23(s, 1H), 7.24(s, 1H), 7.55(d, J=8.4 Hz, 2H), 7.59(s, 1H), 7.99(d, J=8.4 Hz, 2H)

EXAMPLE 108

4-(4,5,7,8,9,10-Hexahydro-7,7,10,10-tetramethylan-thra-[1,2-b]furan-2-yl)benzoic acid

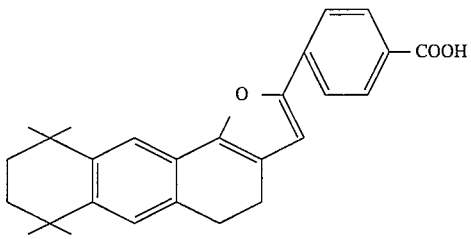

1.0 g of diisopropylamine was dissolved in 30 ml of anhydrous tetrahydrofuran, followed by the addition thereto of 5.8 ml of a 1.6M solution of n-butyllithium in hexane at 0° C. The obtained mixture was stirred for 10 minutes and cooled to –78° C., followed by the addition thereto of 20 ml of a solution of 2.0 g of 3,4,5,6,7,8-hexahydro-5,5,8,8-tetramethyl-1(2H)-anthracenone in anhydrous tetrahydrofuran. The obtained mixture was stirred for 30 minutes, followed by the dropwise addition thereto of 20 ml of a solution of 2.4 g of 4'-carbomethoxy-2-bromoacetophenone in anhydrous tetrahydrofuran. The reaction mixture was brought to room temperature and poured into dilute hydrochloric acid. The obtained mixture was extracted with ethyl acetate. The organic phase was washed with water, a saturated aqueous solution of sodium hydrogencarbonate and a saturated aqueous solution of common salt successively, and dried over anhydrous magnesium sulfate. The solvent was distilled off. Methanol was added to the residue to precipitate a crystal. This crystal was recovered by filtration and washed with methanol to give 0.6 g of a light-brown solid. This solid was dissolved in a mixture comprising 10 ml of methanol and 20 ml of tetrahydro-furan, followed by the addition thereto of 5 ml of a 5N aqueous solution of sodium hydroxide. The obtained mixture was heated under reflux for 30 minutes and cooled to room temperature by allowing to stand, followed by the addition thereto of 20 ml of water. The resulting mixture was acidified with dilute hydrochloric acid to give a precipitate. This precipitate was recovered by filtration and washed with water. 0.5 g of the title compound was obtained as a white solid.

m.p.; 264°–265° C. ¹H-NMR (400 MHz, DMSO-d₆) δ(ppm); 1.23(s, 6H), 1.25(s, 6H), 1.63(s, 4H), 2.84–2.94(m, 4H), 7.22(s, 1H), 7.32(s, 1H), 7.63(d, J=8.4 Hz, 2H), 7.96(d, J=8.4 Hz, 2H), 8.14(s, 1H)

EXAMPLE 109

4-(4,5,7,8,9,10-Hexahydro-7,7,10,10-tetramethylanthra-[2,1-d]thiazol-2-yl)benzoic acid

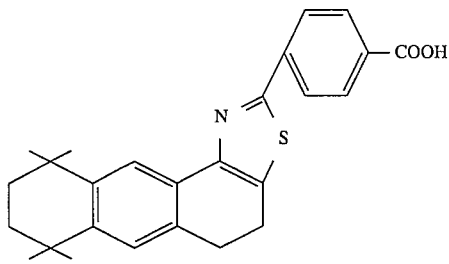

5.0 g of 3,4,5,6,7,8-hexahydro-5,5,8,8-tetramethyl-1(2H)-anthracenone was dissolved in 100 ml of carbon tetrachloride, followed by the dropwise addition thereto of 3.1 g of bromine at room temperature. The obtained mixture was further stirred at room temperature for 30 minutes and concentrated under reduced pressure at a low temperature. The obtained residue was washed with methanol to give 5.0 g of a brown solid.

1.1 g of this brown solid was dissolved in 20 ml of isopropanol, followed by the addition thereto of 0.33 g of 4-carbomethoxybenzthioamide and 0.2 ml of pyridine. The obtained mixture was stirred for 9 hours and cooled by allowing to stand. The precipitated solid was recovered by filtration and purified by silica gel column chromatography (developer: 5% ethyl acetate/n-hexane) to give 0.3 g of a white solid.

This solid was suspended in 20 ml of methanol, followed by the addition thereto of 5 ml of a 5N aqueous solution of sodium hydroxide. The obtained mixture was heated under reflux for 30 minutes and cooled by allowing to stand, followed by the addition thereto of 10 ml of water. The resulting mixture was acidified with dilute hydrochloric acid to give a precipitate. This precipitate was recovered by filtration and washed with water and methanol successively to give 0.24 g of a pale-yellow solid.

m.p.; 275°–278° C. $^1$H-NMR (400 MHz, DMSO-d$_6$) δ(ppm); 1.24(s, 6H), 1.28(s, 6H), 1.64(s, 4H), 2.93–3.08(m, 4H), 7.24(s, 1H), 7.81(s, 1H), 8.04(d, J=8.4 Hz, 2H), 8.08(d, J=8.4 Hz, 2H)

EXAMPLE 110

4-(5,6,8,9,10,11-Hexahydro-8,8,11,11-tetramethylanthra [1,2-b]pyridin-2-yl)benzoic acid

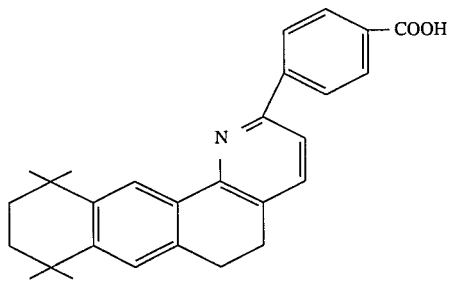

N,N-Dimethyl-(3,5,6,7,8-pentahydro-5,5,8,8-tetramethyl-1(4H)-anthracenon-2-ylidene)amine

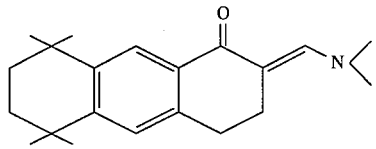

3.0 g of 3,4,5,6,7,8-hexahydro-5,5,8,8-tetramethyl-1(2H)-anthracenone was dissolved in 30 ml of N,N-dimethylformamide, followed by the addition thereto of 3.1 ml of N,N-dimethylformamide dimethyl acetal. The obtained mixture was stirred under heating at 100° C. for 5 hours and cooled by allowing to stand, followed by the addition thereto of 50 ml of water. The formed precipitate was recovered by filtration and washed with water and n-hexane successively to give 2.0 g of a pale-yellow solid.

m.p.; 181°–184° C. $^1$H-NMR (400 MHz, CDCl$_3$) δ(ppm); 1.28(s, 6H), 1.30(s, 6H), 1.66(s, 4H), 2.77(t, J=8.0 Hz, 2H), 2.90(t, J=8.0 Hz, 2H), 3.10(s, 6H), 7.06(s, 1H), 7.68(s, 1H), 7.99(s, 1H) 4-(5,6,8,9,10,11-Hexahydro-8,8,11,11-tetramethylanthra[1,2-b]pyridin-2-yl)benzoic acid

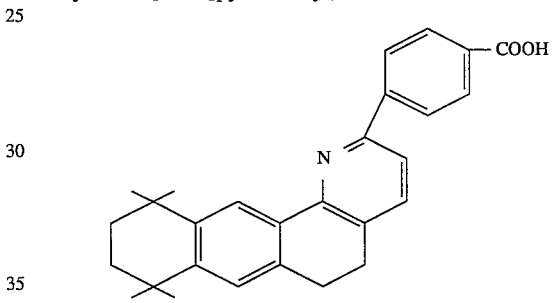

1.4 g of potassium t-butoxide was suspended in 30 ml of anhydrous tetrahydrofuran, followed by the addition thereto of 1.1 g of methyl 4-acetylbenzoate. The obtained mixture was stirred at room temperature for one hour, followed by the addition thereto of 2.0 g of N,N-dimethyl-(3,5,6,7,8-pentahydro-5,5,8,8-tetramethyl-1(4H)-anthracenon-2-ylidene)amine. The obtained mixture was stirred at room temperature for 3 hours, followed by the addition thereto of 20 ml of glacial acetic acid and 5.0 g of ammonium acetate. The obtained mixture was heated under reflux for 5 hours and cooled to room temperature by allowing to stand, followed by the addition thereto of 50 ml of water. The formed precipitate was recovered by filtration and washed with water and methanol successively to give 0.7 g of a pale-yellow solid.

This solid was suspended in 30 ml of methanol, followed by the addition thereto of 10 ml of a 5N aqueous solution of sodium hydroxide. The obtained mixture was heated under reflux for 30 minutes and cooled to room temperature by allowing to stand, followed by the addition thereto of 20 ml of water. The pH of the resulting mixture was adjusted to 4 with hydrochloric acid. The formed precipitate was recovered by filtration and washed with water and methanol successively. 0.5 g of the title compound was obtained as a pale-yellow solid.

m.p.; 267°–270° C. $^1$H-NMR (400 MHz, DMSO-d$_6$) δ(ppm); 1.26(s, 6H), 1.32(s, 6H), 1.64(s, 4H), 2.80–2.98(m, 4H), 7.24(s, 1H), 7.74(d, J=8.0 Hz, 1H), 7.86(d, J=8.0 Hz, 1H), 8.07(d, J=8.4 Hz, 2H), 8.28(d, J=8.4 Hz, 2H), 8.30(s, 1H)

EXAMPLE 111

4-(5,6,8,9,10,11-Hexahydro-8,8,11,11-tetramethylanthra[1,2-b]pyridin-4-yl)benzoic acid

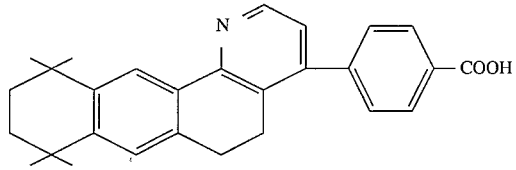

0.5 g of methyl 4-(3,5,6,7,8-pentahydro-5,5,8,8-tetramethyl-1(4H)-anthracenon-2-ylidene)benzoate was dissolved in 15 ml of 1,2-dichloroethane, followed by the addition thereto of 5 ml of ethyl vinyl ether and 0.063 g of tris(6,6,7,7,8,8,8-heptafluoro-2,2-dimethyloctane-3,5-dionato)ytterbium (III). The obtained mixture was heated under reflux for 48 hours and vacuum-distilled to remove the solvent. The obtained residue was dissolved in 20 ml of acetonitrile, followed by the addition thereto of 0.25 g of hydroxylamine hydrochloride. The obtained mixture was heated under reflux for 9 hours, cooled to room temperature by allowing to stand, and extracted with ethyl acetate. The organic phase was washed with a saturated aqueous solution of common salt, dried over anhydrous magnesium sulfate and concentrated under reduced pressure. The residue was purified by silica gel chromatography (developer: 20% ether/n-hexane) to give 0.33 g of a pale-yellow powder. This powder was suspended in 10 ml of methanol, followed by the addition thereto of 5 ml of a 5N aqueous solution of sodium hydroxide. The obtained mixture was heated under reflux for one hour and cooled to room temperature by allowing to stand. The pH of the resulting mixture was adjusted to 4 with dilute hydrochloric acid. The formed precipitate was recovered by filtration and washed with water. 0.19 g of the title compound was obtained as a white solid.

m.p.; 286°–289° C. $^1$H-NMR (400 MHz, DMSO-$d_6$) δ(ppm); 1.24(s, 6H), 1.28(s, 6H), 1.64(s, 4H), 2.68–2.84(m, 4H), 7.18(d, J=5.4 Hz, 1H), 7.20(s, 1H), 7.54(d, J=8.4 Hz, 2H), 8.03(d, J=8.4 Hz, 2H), 8.18(s, 1H), 8.56(d, J=5.4 Hz, 1H)

EXAMPLE 112

4-(7,8,9,10-Tetrahydro-7,7,10,10-tetramethylnaptho[3,2-b]-1-azainden-4-yl)benzoic acid

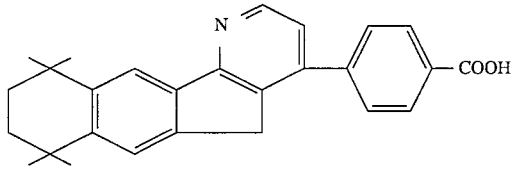

The above compound was prepared in the same manner as that of the Example 111.

m.p.; 283° C. (dec.) $^1$H-NMR (400 MHz, DMSO-$d_6$) δ(ppm); 1.26(s, 6H), 1.32(s, 6H), 1.68(s, 4H), 4.03(s, 2H), 7.36(d, J=5.4 Hz, 1H), 7.60(s, 1H), 7.88(d, J=8.4 Hz, 2H), 7.93(s, 1H), 8.08(d, J=8.4 Hz, 2H), 8.60(d, J=5.4 Hz, 1H)

EXAMPLE 113

4-(4,7,8,9,10-Pentahydro-7,7,10,10-tetramethyl-5-oxoanthra[4,3-c]isoxazol-3-yl)benzoic acid

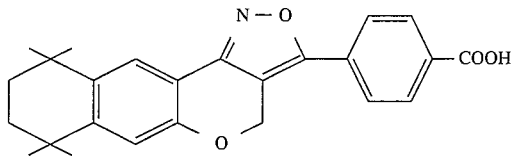

5,6,7,8-Tetrahydro-2-methoxymethoxy-5,5,8,8-tetramethylnaphthalene

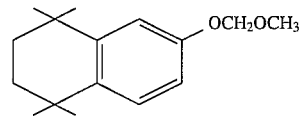

10 ml of a solution of 4.0 g of 5,6,7,8-tetrahydro-5,5,8,8-tetramethyl-2-naphthol in N,N-dimethylformamide was dropwise added to 70 ml of a suspension of 1.01 g of sodium hydride (60% solution in oil) in anhydrous N,N-dimethylformamide at 0° C. The obtained mixture was stirred at room temperature for one hour and cooled to 0° C., followed by the addition thereto of 5 ml of a solution of 2.36 g of chloromethyl methyl ether in N,N-dimethylformamide. The temperature of the mixture was gradually raised to room temperature (in 10 minutes). The resulting mixture was further stirred for one hour, followed by the addition thereto of 30 ml of a saturated aqueous solution of sodium hydrogencarbonate. The obtained mixture was extracted with ethyl acetate. The organic phase was washed with a saturated aqueous solution of common salt, dried over anhydrous magnesium sulfate and distilled to remove the solvent. The residue was purified by silica gel chromatography (developer: 5% ethyl acetate/n-hexane) to give 5.2 g of the title compound as a colorless oil. $^1$H-NMR (400 MHz, CDCl$_3$) δ(ppm); 1.26(s, 6H), 1.29(s, 6H), 1.70(s, 4H), 3.50(s, 3H), 5.18(s, 2H), 6.87(dd, J=8.4, 2.4 Hz, 1H), 6.97(d, J=2.4 Hz, 1H), 7.23(d, J=8.4 Hz, 1H)

3-Formyl-5,6,7,8-tetrahydro-2-methoxymethoxy-5,5,8,8-tetramethylnaphthalene

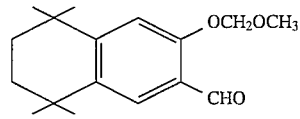

22 ml of a 1.56M solution of n-butyllithium in hexane was dropwise added to 40 ml of a solution of 5.7 g of 5,6,7,8-tetrahydro-2-methoxymethoxy-5,5,8,8-tetramethylnaphthalene in anhydrous diethyl ether at −78° C. The temperature of the mixture was gradually raised to room temperature (in 10 minutes). The resulting mixture was stirred for 5 hours and cooled to −78° C., followed by the dropwise addition thereto of 5 ml of a solution of 2.6 g of N,N-dimethylformamide in diethyl ether. The temperature of the obtained mixture was gradually raised to room temperature (in 10 minutes). The resulting mixture was stirred for 3 hours, followed by the addition thereto of 30 ml of a saturated aqueous solution of ammonium chloride. The obtained mixture was extracted with ethyl acetate. The organic phase was washed with a saturated aqueous solution of common salt, dried over anhydrous magnesium sulfate and distilled to remove the solvent. The residue was purified by silica gel chromatography (developer: 10% ethyl acetate/n-hexane) to give 4.2 g of the title compound as a white solid.

m.p.; 84°–85° C. $^1$H-NMR (400 MHz, CDCl$_3$) δ(ppm); 1.26(s, 6H), 1.28(s, 6H), 1.68(brs, 4H), 3.53(s, 3H), 5.26(s, 2H), 7.12(s, 1H), 7.80(s, 1H), 10.40(s, 1H)

3-Formyl-5,6,7,8-tetrahydro-2-hydroxy-5,5,8,8-tetramethylnaphthalene

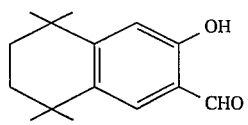

A 10% aqueous solution of hydrochloric acid was added to 30 ml of a solution of 2.4 g of 3-formyl-5,6,7,8-tetrahydro-2-methoxymethoxy-5,5,8,8-tetramethylnaphthalene in tetrahydrofuran at room temperature. The obtained mixture was stirred at 50° C. for 4 hours, followed by the addition thereto of 30 ml of water. The obtained mixture was extracted with ethyl acetate. The organic phase was washed with a saturated aqueous solution of common salt, dried over anhydrous magnesium sulfate and distilled to removd the solvent. The residue was purified by silica gel chromatography (developer: 10% diethyl ether/n-hexane) to give 1.8 g of the title compound as a colorless oil.

$^1$H-NMR (400 MHz, CDCl$_3$) δ(ppm); 1.28(s, 6H), 1.29(s, 6H), 1.70(s, 4H), 6.93(s, 1H), 7.46(s, 1H), 9.83(s, 1H), 10.61(s, 1H)

Ethyl 4-(3-hydroxy-1-propynyl)benzoate

2.5 g of tetrakis(triphenylphosphine)palladium (0) was added to 50 ml of a solution of 10 g of ethyl p-bromobenzoate in benzene at room temperture. The obtained mixture was stirred at that temperature for one hour, followed by the addition thereto of 2.5 g of propargyl alcohol, 0.84 g of cuprous iodide and 19 g of diethylamine. The obtained mixture was stirred at room temperature for 26 hours and filtered through Celite. Water (50 ml) was added to the filtrate and the obtained mixture was extracted with ethyl acetate. The organic phase was washed with a 10% aqueous solution of hydrochloric acid and a saturated aqueous solution of common salt, dried over anhydrous magnesium sulfate and distilled to remove the solvent. The residue was purified by silica gel chromatography (developer: 20% ethyl acetate/n-hexane) to give 3.1 g of the title compound as a pale-yellow solid.

m.p.; 58°–60° C. $^1$H-NMR (400 MHz, CDCl$_3$) δ(ppm); 1.38(t, J=7.2 Hz, 3H), 4.38(q, J=7.2 Hz, 2H), 4.52(d, J=6.0 Hz, 2H), 7.48(d, J=8.4 Hz, 2H), 7.99(d, J=8.4 Hz, 2H)

Ethyl 4-(3-bromo-1-propynyl)benzoate

1.7 g of carbon tetrabromide and 1.15 g of triphenylphosphine were added to 10 ml of a solution of 0.70 g of ethyl 4-(3-hydroxy-1-propynyl)benzoate in methylene chloride at room temperature. The obtained mixture was stirred at that temperature for 13 hours, followed by the addition thereto of 20 ml of water. The obtained mixture was extracted with ethyl acetate. The organic phase was washed with a saturated aqueous solution of common salt, dried over anhydrous magnesium sulfate and distilled to remove the solvent. The residue was purified by silica gel chromatography (developer: 5% diethyl ether/n-hexane) to give 1.0 g of the title compound as a pale-yellow oil. $^1$H-NMR (400 MHz, CDCl$_3$) δ(ppm); 1.38(t, J=7.2 Hz, 3H), 4.17(s, 2H), 4.36(q, J=7.2 Hz, 2H), 7.50(d, J=8.4 Hz, 2H), 7.99(d, J=8.4 Hz, 2H)

Ethyl 4-[3-(3-formyl-5,6,7,8-tetrahydro-5,5,8,8tetramethyl-2-naphthoxy)-1-propynyl]benzoate

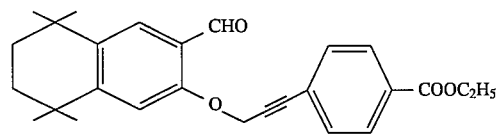

0.71 g of potassium carbonate and 1.0 g of ethyl 4-(3-bromo-1-propynyl)benzoate were added to 20 ml of a solution of 0.80 g of 3-formyl-5,6,7,8-tetrahydro-2-hydroxy-5, 5,8,8-tetramethylnaphthalene in anhydrous N,N-dimethyl formamide at room temperature. The obtained mixture was stirred at 50° C. for 30 minutes, followed by the addition thereto of 20 ml of water. The obtained mixture was extracted with ethyl acetate. The organic phase was washed with a saturated aqueous solution of common salt, dried over anhydrous magnesium sulfate and distilled to remove the solvent. The residue was purified by silica gel chromatography (developer: 20% diethyl ether/n-hexane) to give 0.87 g of the title compound as a pale-yellow solid.

m.p.; 114°–115° C. $^1$H-NMR (400 MHz, CDCl$_3$) δ(ppm); 1.28(s, 6H), 1.30(s, 6H), 1.38(t, J=7.2 Hz, 3H), 1.68–1.72(m, 4H), 4.37(q, J=7.2 Hz, 2H), 5.4(s, 2H), 7.11(s, 1H), 7.47(d, J=S.4 Hz, 2H), 7.82(s, 1H), 7.98(d, J=8.4 Hz, 2H), 10.41(s, 1H)

Ethyl 4-[3-(3-hydroxyiminomethyl-5,6,7,8-tetrahydro-5,5,8,8-tetramethyl-2-naphthoxy)-1-propynyl] benzoate

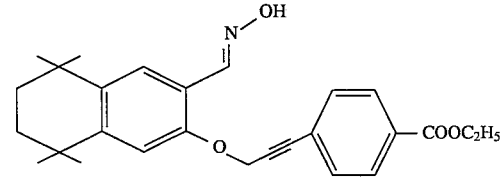

0.2 g of hydroxylamine hydrochloride and 0.26 g of sodium acetate were added to 15 ml of a solution of 0.51 g of ethyl 4-[3-(3-formyl-5,6,7,8-tetrahydro-5,5,8,8-tetramethyl-2-naphthoxy)-1-propynyl]benzoate in methanol at room temperature. The obtained mixture was stirred at 50° C. for 11 hours and distilled to remove the methanol, followed by the addition thereto of 20 ml of water. The obtained mixture was extracted with ethyl acetate. The organic phase was washed with a saturated aqueous solution of common salt, dried over anhydrous magnesium sulfate and distilled to remove the solvent. The residue was purified by silica gel chromatography (developer: 30% diethyl ether/ n-hexane) to give 0.33 g of the title compound as a pale-yellow oil. $^1$H-NMR (400 MHz, CDCl$_3$) δ(ppm); 1.28(s, 6H), 1.30(s, 6H), 1.36(t, J=7.2 Hz, 3H), 1.68(brs, 4H), 4.36(q, J=7.2 Hz, 2H), 4.94(s, 2H), 7.04(s, 1H), 7.47(d, J=8.4 Hz, 2H), 7.68(s, 1H), 7.98(d, J=8.4 Hz, 2H), 8.50(s, 1H)

Ethyl 4-(4,7,8,9,10-pentahydro-7,7,10,10-tetramethyl-5-oxoanthra[4,3-c]isoxazol-3-yl)benzoate

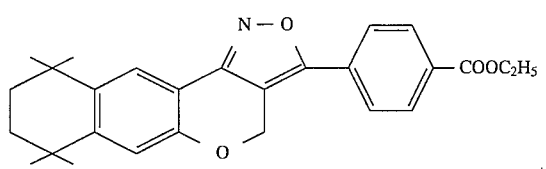

1.3 ml of a 6% aqueous solution of sodium hypochlorite was added to 20 ml of a solution of 0.33 g of ethyl 4-[3-(3-hydroxyiminomethyl-5,6,7,8-tetrahydro-5,5,8,8-tetramethyl-2-naphthoxy)-1-propynyl]-benzoate in methylene chloride at room temperature. The obtained mixture was stirred at that temperature for 2 hours, followed by the addition thereto of 20 ml of a saturated aqueous solution of common salt. The obtained mixture was extracted with methylene chloride. The organic phase was washed with a saturated aqueous solution of common salt, dried over anhydrous magnesium sulfate and distilled to remove the solvent. The residue was washed with ethanol to give 0.28 g of the title compound as a pale-yellow solid.

m.p.; 174°–175° C. $^1$H-NMR (400 MHz, CDCl$_3$) δ(ppm); 1.27(s, 6H), 1.31(s, 6H), 1.42(t, J=7.2 Hz, 3H), 1.70(s, 4H), 4.42(q, J=7.2 Hz, 2H), 5.44(s, 2H), 6.99(s, 1H), 7.70(d, J=8.4 Hz, 2H), 7.84(s, 1H), 8.18(d, J=8.4 Hz, 2H)

4-(4,7,8,9,10-Pentahydro-7,7,10,10-tetramethyl-5-oxoanthra[4,3-c]isoxazol-3-yl)benzoic acid

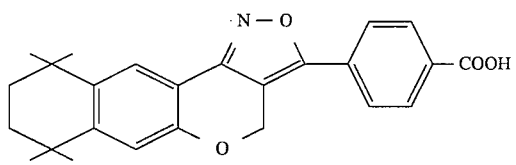

2 ml of a 5N aqueous solution of sodium hydroxide was added to 20 ml of a solution of 0.07 g of ethyl 4-(4,7,8,9,10-pentahydro-7,7,10,10-tetramethyl-5-oxoanthra[4,3-c]isoxazol-3-yl)benzoate in ethanol at room temperature. The obtained mixture was heated under reflux for 2 hours and cooled to room temperature by allowing to stand. The pH of the mixture was adjusted to 4 with dilute hydrochloric acid. The formed precilitate was recovered by filtration and washed with water to give 0.06 g of the title compound as a white solid.

m.p.; 292° C. (dec.) $^1$H-NMR (400 MHz, DMSO-d$_6$) δ(ppm); 1.23(s, 6H), 1.26(s, 6H), 1.63(s, 4H), 5.54(s, 2H), 7.04(s, 1H), 7.67(s, 1H), 7.75(d, J=8.4 Hz, 2H), 8.05(d, J=8.4 Hz, 2H)

EXAMPLE 114

(6,7,9,10,11,12-Hexahydro-9,9,12,12-tetramethyl-anthra[1,2-b]indo]-4-yl)carboxylic acid

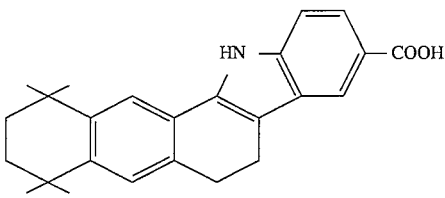

1.0 g of 3,4,5,6,7,8-hexahydro-5,5,8,8-tetramethyl-1(2H)-anthracenone and 0.8 g of 4-hydrazinobenzoic acid hydrochloride were suspended in 20 ml of glacial acetic acid. The obtained suspension was heated under reflux for 4 hours and cooled to room temperature by allowing to stand, followed by the addition thereto of 50 ml of water. The precipitated solid was recovered by filtration and washed with water and n-hexane successively to give 1.1 g of the title compound as a light-brown solid.

m.p.; 255°–256° C. $^1$H-NMR (400 MHz, DMSO-d$_6$) δ(ppm); 1.23(s, 6H), 1.28(s, 6H), 1.62(s, 4H), 2.82–2.98(m, 4H), 7.20(s, 1H), 7.40(d, J=9.0 Hz, 1H), 7.62(s, 1H), 7.68(dd, J =9.0, 2.6 Hz, 1H), 8.11(d, J=2.6 Hz, 1H)

EXAMPLE 115

(6,7,9,10,11,12-Hexahydro-1,9,9,12,12-pentamethy-lanthra [1,2-b]indo]-4-yl)carboxylic acid

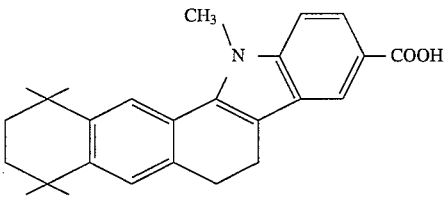

1.0 g of the compound prepared in the Example 114 was dissolved in 20 ml of N,N-dimethylformamide, followed by the addition thereto of 0.84 ml of methyl iodide and 1.1 g of potassium carbonate. The obtained mixture was stirred at 100° C. for 20 hours, cooled to room temperatare by allowing to stand, and extracted with 100 ml of ethyl acatate. The organic phase was washed with a saturated aqueous solution of common salt, dried over anhydrous magnesiun sulfate and concentrated under reduced pressure. The residue was purified by silica gel chromatography (developer: 3% ethyl acetate/n-hexane) to give 0.4 g of a white solid.

This solid was suspended in 30 ml of methanol, followed by the addition thereto of 10 ml of a 5N aqueous solution of sodium hydroxide. The obtained mixture was heated under reflux for 30 minutes and cooled to room temperature by allowing to stand, followed by the addition thereto of 20 ml of water. The pH of the resulting mixture was adjusted to 3 with dilute hydrochloric acid to precipitate a white solid. This solid was recovered by filtration and washed with water to give 0.4 g of the title compound.

81 m.p.; 162°–164° C. ¹H-NMR (400 MHz, DMSO-d$_6$) δ(ppm); 1.25(s, 6H), 1.30(s, 6H), 1.64(s, 4H), 2.85(s, 4H), 4.05(s, 3H), 7.31(s, 1H), 7.54(d, J=9.0 Hz, 1H), 7.60(s, 1H), 7.75(dd, J=9.0, 2.6 Hz, 1H), 8.17 ( d, J=2.6 Hz, 1H)

EXAMPLE 116

N-Phenyl-4-(4,5,7,8,9,10-hexadydro-1,7,7,10,10-pentamethylanthra[2,1-d]pyrazol-3-yl)benzamide

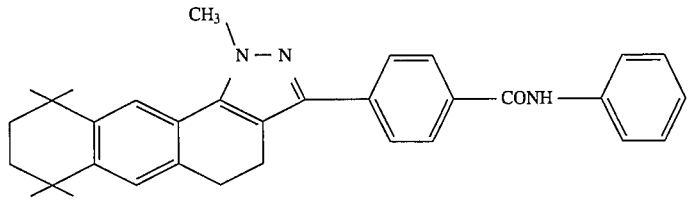

0.5 g of the 4-(4,5,7,8,9,10-hexahydro-1,7,7,10,10-pentamethylanthra[2,1-d]pyrazol-3-yl)benzoic acid prepared in the Example 7 was dissolved in 10 ml of N,N-dimethylformamide. Under cooling with ice, 0.21 ml of diethyl chlorophosphate and 0.2 ml of triethylamine were added to the solution and the obtained mixture was stirred for 30 minutes. The resulting mixture was further stirred at room temperature for 30 minutes, followed by the addition thereto of 0.17 g of aniline. The obtained mixture was stirred for 5 hours, followed by the addition thereto of 100 ml of ethyl acetate. The organic phase was washed with a saturated aqueous solution of sodium hydrogencarbonate and a saturated aqueous solution of common salt successively, dried over anhydrous magnesium sulfate and concentrated under reduced pressure. The residue was purified by silica gel chromatography (developer: 25% ethyl acetate/n-hexane) to give 0.2 g of the title compound as a pale-yellow solid.

82 m.p.; 269°–270° C. ¹H-NMR (400 MHz, CDCl$_3$) δ(ppm); 1.33(s, 6H), 1.36(s, 6H), 1.72(s, 4H), 2.90(s, 4H), 4.23(s, 6H), 7.16(t, J =7.6 Hz, 1H), 7.27(s, 1H), 7.39(t, J=7.6 Hz, 1H), 7.54(s, 1H), 7.68(d, J=8.0 Hz, 2H), 7.84(d, J=8.4 Hz, 2H), 7.89(brs, 1H), 7.94(d, J =8.4 Hz, 2H)

The compounds of Examples 117 and 118, of which structural formulas or the like will be described in Table 34, were prepared in the same manner as that of the Example 116.

TABLE 34

| Ex. | structural formula | ¹H-NMR(400MHz, CDCl$_3$)δ | m.p. (°C.) |
|---|---|---|---|
| 117 | (structure with CO—N(C$_2$H$_5$)$_2$) | 1.01~1.31(m, 6H), 1.30(s, 6H), 1.34(s, 6H), 1.62(s, 4H), 2.88(s, 4H), 3.22~3.33(m, 2H), 3.50~3.60(m, 2H), 4.23(s, 3H), 7.26(s, 1H), 7.43(d, J=8.4Hz, 2H), 7.53(s, 1H), 7.72(d, J=8.4Hz, 2H) | 187~188 |
| 118 | (structure with CO—N-morpholine) | 1.30(s, 6H), 1.34(s, 6H), 1.72(s, 4H), 2.90(s, 4H), 3.41~3.86(m, 8H), 4.23(s, 3H), 7.26(s, 1H), 7.46(d, J=8.4Hz, 2H), 7.53(s, 1H), 7.76(d, J=8.4Hz, 2H) | 182~184 |

EXAMPLE 119

Morpholinoethyl 4-[4,5,7,8,9,10-hexabydro-7,7,10,10-tetramethyl-1-(3-pyridylmethyl)anthra[1,2-d]pyrrol-3-yl)benzoate

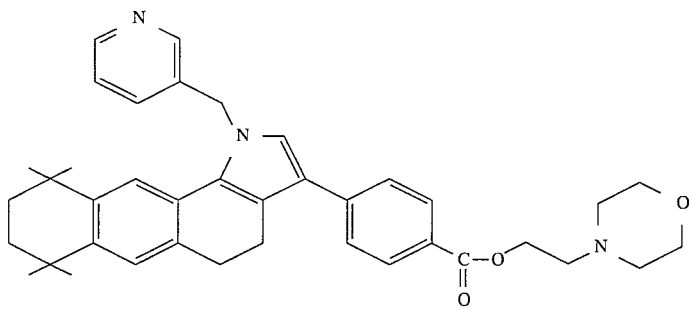

53 g of methyl 4-[4,5,7,8,9,10-hexahydro-7,7,10,10-tetramethyl-1-(3-pyridylmethyl)anthra[1,2-d]pyrrol-3-yl)benzoate was suspended in 150 ml of 4-morpholinoethanol. The suspension thus obtained was stirred under heating at 220° C. for 6 hours under a nitrogen stream and cooled to room temperature by allowing to stand, followed by the addition thereto of ethyl acetate. The organic phase was washed with a saturated aqueous solution of common salt, dried over anhydrous magnesium sulfate and concentrated under reduced pressure. The residue was purified by silica gel chromatography (developer: ethyl acetate). The purified product was washed with methanol to give 23.6 g of the title compound as a white solid.

m.p.; 214°–215° C. $^1$H-NMR (400 MHz, CDCl$_3$) δ(ppm); 0.96(s, 6H), 1.26(s, 6H), 1.56–1.65(m, 4H), 2.55–2.62(m, 4H), 2.80(t, J=6.0 Hz, 2H), 2.82–2.94(m, 4H), 3.71(t, J=4.8 Hz, 4H), 4.47(t, J=6.0 Hz, 2H), 5.50(s, 2H), 6.94(s, 2H), 7.18(s, 1H), 7.25–7.29(m, 1H), 7.35–7.40(m, 1H), 7.50(d, J=8.4 Hz, 2H), 8.03(d, J=8.4 Hz, 2H), 8.53–8.60(m, 2H)

The following Referential Examples relate to the preparation of the ketone compounds represented by the general formula (II):

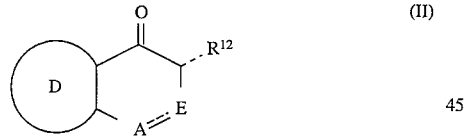

wherein the ring D, A, E and R$^{12}$ are each as defined above, which were used in the foregoing Examples as the raw materials.

REFERENTIAL EXAMPLE 1

3,5,6,7,8-Pentahydro-5,5,8,8-tetramethyl-4-thia-](2H)-anthracenone

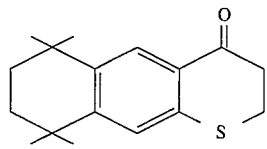

2-Chlorosulfonyl-5,6,7,8-tetrahydro-5,5,8,8-tetramethylnaphthalene

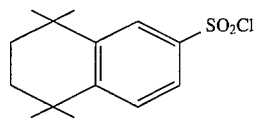

30 g of 1,2,3,4-tetrahydro-1,2,4,4-tetramethylnaphthalene was dropwise added in 20 minutes to 50 ml of chlorosulfonic acid cooled to 0° C. The obtained mixture was stirred for 30 minutes, further stirred at room temperature for 4 hours and poured onto ice-water. The obtained mixture was extracted with ethyl acetate. The organic phase was washed with water, dried over anhydrous magnesium sulfate and concentrated under reduced pressure. The residue was used in the subsequent reaction without further purification.

2-(5,6,7,8-Tetrahydro-5,5,8,8-tetramethylnaphthalene)thiol

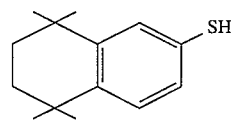

30 g of 2-chlorosulfonyl-5,6,7,8-tetrahydro-5,5,8,8-tetramethylnaphthalene was dissolved in 200 ml of ethanol, followed by the addition thereto of 50 g of zinc powder. 200 ml of concentrated hydrochloric acid was dropwise added to the obtained mixture in 30 minutes. The obtained mixture was heated under reflux for one hour, brought to room temperature and filtered through Celite to remove insolubles. The filtrate was distilled under reduced pressure to remove the solvent. The residue was dissolved in ethyl acetate. The obtained solution was washed with a saturated aqueous solution of common salt, dried over anhydrous magnesium sulfate and filtered to remove the drying agent. The filtrate was distilled under reduced pressure to remove the solvent. 30.5 g of the title compound was obtained as a brown oil. $^1$H-NMR (400 MHz, CDCl$_3$) δ(ppm); 1.24(s, 6H), 1.25(s, 6H), 1.65(s, 4H), 3.36(s, 1H), 7.03 (dd, J=8.9 Hz, 2.5 Hz, 1H), 7.17(d, J=8.9 Hz, 1H), 7.22(d, J=2.5 Hz, 1H)

3-[2-(5,6,7,8-Tetrahydro-5,5,8,8-tetramethylnaphth-yl)thio]propionic acid

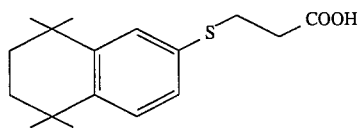

14 ml of methyl acrylate and 1.1 ml of a 28% solution of sodium methoxide in methanol were added to 26 g of 2-(5,6,7,8-tetrahydro-5,5,8,8-tetramethylnaphthalene)thiol. The obtained mixture was stirred at room temperature for one hour, followed by the addition thereto of 200 ml of ethyl acetate. The organic phase was washed with dilute hydrochloric acid, water, a saturated aqueous solution of sodium hydrogencarbonate and a saturated aqueous solution of common salt successively, dried over anhydrous magnesium sulfate and distilled under reduced pressure to remove the solvent. The residue was purified by silica gel chromatography (developer: 2% ethyl acetate/n-hexane) to give 24 g of a yellow oil.

This oil was dissolved in 100 ml of methanol, followed by the addition thereto of 100 ml of a 5N aqueous solution of sodium hydroxide. The obtained mixture was stirred at room temperature for 2 hours, followed by the addition thereto of 200 ml of water. The resulting mixture was acidified with dilute hydrochloric acid and extracted with ethyl acetate. The organic phase was washed with a saturated aqueous solution of common salt and dried over anhydrous magnesium sulfate.

Vacuum concentration was conducted and the obtained residue was washed with n-hexane. 15.4 g of the title compound was obtained as a white solid.

m.p.; 101° C. $^1$-NMR (400 MHz, CDCl$_3$) δ(ppm); 1.24(s, 6H), 1.26(s, 6H), 1.66(s, 4H), 2.66(t, J=7.0 Hz, 2H), 3.10(t, J=7.0 Hz, 2H), 7.14(dd, J=8.9 Hz, 2.5 Hz, 1H), 7.23(d, J=8.9 Hz, 1H), 7.32(d, J=2.5 Hz, 1H)

3,5,6,7,8-Pentahydro-5,5,8,8-tetramethyl-4-thia-1(2H)-anthracenone

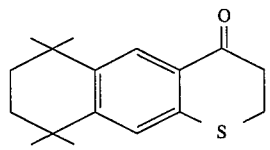

15.4 g of the carboxylic acid compound obtained above was dissolved in 100 ml of anlydrous benzene, followed by the addition thereto of 7.7 ml of thionyl chloride. The obtained mixture was heated under reflux for one hour, cooled to room temperature and concentrated under reduced pressure. The obtained residue was dissolved in 30 ml of carbon disulfide and the obtained solution was added to 100 ml of a suspension of 9.2 g of aluminum chloride in carbon disulfide in portions. The obtained mixture was stirred at room temperature for 2 hours and poured onto ice-water. The obtained mixture was extracted with 300 ml of ethyl acetate. The organic phase was washed with water, a saturated aqueous solution of sodium hydrogencarbonate and a saturated aqueous solution of common salt successively, dried over anhydrous magnesium sulfate and concentrated under reduced pressure. The residue was washed with n-hexane to give 9.6 g of the title compound as a pale-yellow solid.

m.p.; 144°–145° C. $^1$H-NMR (400 MHz, CDCl$_3$) δ(ppm); 1.25(s, 6H), 1.26(s, 6H), 1.66(s, 4H), 2.94 (t, J=9.0 Hz, 2H), 3.20 (t, J=9.0 Hz, 2H), 7.19(s, 1H), 8.08(s, 1H)

REFERENTIAL EXAMPLE 2

7,8,9,10-Tetrahydro-7,7,10,10-tetramethylnaphtho-[2,3-b]cyclohepta-1-one

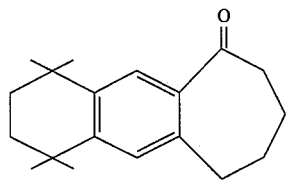

4-[2-(5,6,7,8-Tetrahydro-5,5,8,8-tetramethylnaph-thoyl)]butyric acid

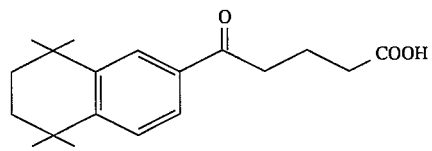

10 g of 1,2,3,4-tetrahydro-1,1,4,4-tetramethylnaphthalene and 6.0 g of glutaric anhydride were dissolved in 100 ml of methylene chloride to prepare a solution. Under cooling with ice, 14.2 g of aluminum chloride was added to the solution and the obtained mixture was stirred for 30 minutes. The mixture was further stirred at room temperature for 3.5 hours and poured onto ice-water. The obtained mixture was extracted with ethyl acetate. The organic phase was washed with a saturated aqueous solution of common salt, dried over anhydrous magnesium sulfate and distilled under reduced pressure to remove the solvent. The obtained residue was washed with n-hexane to give 5.1 g of the title compound as a white solid.

m.p.; 117°–118° C. $^1$H-NMR (400 MHz, CDCl$_3$) δ(ppm); 1.28(s, 6H), 1.30(s, 6H), 1.70(s, 4H), 2.03–2.13(m, 2H), 2.50(t, J=7.2 Hz, 2H), 3.04(t, J=7.2 Hz, 2H), 7.38(d, J=8.8 Hz, 1H), 7.70(dd, J=8.8 Hz, 2.5 Hz, 1H), 7.94(d, J=2.5 Hz, 1H)

5-[2-(5,6,7,8-Tetrahydro-5,5,8,8-tetramethylnaphth-yl)valeric acid

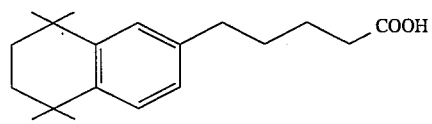

5.0 g of 4-[2-(5,6,7,8-tetrahydro-5,5,8,8tetramethylnaph-thoyl)]butyric acid was suspended in 100 ml of diethylene glycol, followed by the addition thereto of 3.3 g of sodium hydroxide and 2.5 g of hydrazine monohydrate. The obtained mixture was vigorously stirred at 180° C. under a nitrogen stream for 6 hours, cooled by allowing to stand, and poured into cool dilute hydrochloric acid. The obtained mixture was extracted with ethyl acetate. The organic phase was washed with a saturated aqueous solution of common salt, dried over anhydrous magnesium sulfate and distilled to remove the solvent. 4.3 g of the title compound was obtained as a yellow oil.

¹H-NMR (400 MHz, CDCl₃) δ(ppm); 1.25(s, 6H), 1.26(s, 6H), 1.60–1.76(m, 4H), 1.66(s, 4H), 2.38(t, J=7.2 Hz, 2H), 2.57(t, J=7.2 Hz, 2H), 6.92(dd, J=8.8 Hz, 2.5 Hz, 1H), 7.08(d, J=2.5 Hz, 1H), 7.20(d, J=8.8 Hz, 1H)

7,8,9,10-Tetrahydro-7,7,10,10-tetramethylnaphtho[2,3-b]cyclohepta-1-one

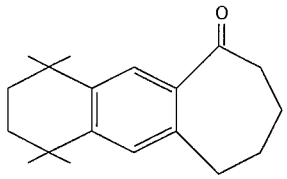

4.3 g of 5-[2-(5,6,7,8-tetrahydro-5,5,8,8-tetramethylnaphthyl)]valeric acid was dissolved in 100 ml of anhydrous benzene, followed by the addition thereto of 3.3 ml of thionyl chloride. The obtained mixture was heated under reflux for 40 minutes, cooled by allowing to stand and concentrated under reduced pressure. The residue was dissolved in 20 ml of carbon disulfide. The obtained solution was dropwise added to 100 ml of suspension of 4.0 g of aluminum chloride in carbon disulfide. The obtained mixture was heated under reflux for 30 minutes, cooled to room temperature by allowing to stand, and poured onto ice-water. The obtained mixture was extracted with ethyl acetate. The organic phase was washed with water, a saturated aqueous solution of sodium hydrogencarbonate and a saturated aqueous solution of common salt successively, dried over anhydrous magnesium sulfate, and distilled under reduced pressure to remove the solvent. 3.5 g of the title compound was obtained as a light-brown solid.

m.p.; 102°–105° C. ¹H-NMR (400 MHz, CDCl₃) δ(ppm); 1.28(s, 12H), 1.67(s, 4H), 1.76–1.90(m, 4H), 2.66–2.74(m, 2H), 2.83–2.92(m, 2H), 7.09(s, 1H), 7.71(s, 1H)

REFERENTIAL EXAMPLE 3

3,4,6,7,8-Pentahydro-6,6-dimethyl-9-thia-1(2H)anthracenone

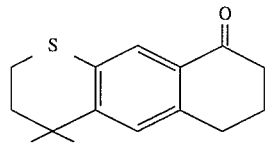

γ-Oxo-6-(4,4-dimethylthiochromanoyl)]butyric acid

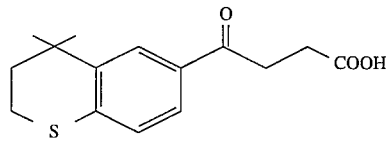

18.8 g of 4,4-dimethylthiochroman and 21 g of aluminum chloride were added to 150 ml of methylene chloride to prepare a mixture. Under cooling with ice, 18.1 ml of monoethyl succinate chloride was dropwise added to the mixture and the obtained mixture was stirred for 30 minutes. The resulting mixture was further stirred at room temperature for 6 hours and poured onto ice-water. The obtained mixture was extracted with 30 ml of ethyl acetate. The organic phase was washed with water, a saturated aqueous solution of sodium hydrogencarbonate and a saturated aqueous solution of common salt successively, dried over anhydrous magnesium sulfate and concentrated under reduced pressure. The obtained residue was dissolved in 100 ml of ethanol, followed by the addition thereto of 50 ml of a 5N aqueous solution of sodium hydroxide. The obtained mixture was stirred at room temperature for 3 hours, acidified with dilute hydrochloric acid and extracted with ethyl acetate. The organic phase was washed with a saturated aqueous solution of common salt, dried over anhydrous magnesium sulfate and distilled to remove the solvent. The obtained solid residue was recrystallized from ethyl acetate/n-hexane to give 11.4 g of the title compound as a colorless crystal.

m.p.; 116°–117° C. ¹H-NMR (400 MHz, CDCl₃) δ(ppm); 1.35(s, 6H), 1.96(t, J=9.0 Hz, 2H), 2.78(t, J=7.0 Hz, 2H), 3.04(t, J=9.0 Hz, 2H), 3.25(t, J=7.0 Hz, 2H), 7.15(d, J=8.9 Hz, 1H), 7.61(dd, J=8.9 Hz, 2.5 Hz, 1H), 8.00(d, J=2.5 Hz, 1H)

4-[6-(4,4-Dimethylthiochromanyl)]butyric acid

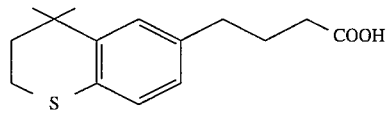

11.4 g of γ-oxo-6-(4,4-dimethylthiochromanyl)]butyric acid was suspended in 100 ml of diethylene glycol, followed by the addition thereto of 8.2 g of sodium hydroxide and 6 ml of hydrazine monohydrate. The obtained mixture was vigorously stirred at 140° C. under a nitrogen stream for 6 hours, cooled by allowing to stand, and poured into cool dilute hydrochloric acid. The obtained mixture was extracted with ethyl acetate. The organic phase was washed with a saturated aqueous solution of common salt, dried over anhydrous magnesium sulfate and concentrated under reduced pressure. 11.0 g of an oily residue was obtained and this residue was used in the subsequent reaction without further purification.

3,4,6,7,8-Pentahydro-6,6-dimethyl-9-thia-1(2H)anthracenone

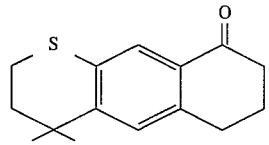

11.0 g of the crude 4-[6-(4,4-dimethylthiochromanyl)]butyric acid was dissolved in 100 ml of anhydrous benzene, followed by the addition thereto of 9 ml of thionyl chloride. The obtained mixture was heated under reflux for 40 minutes, cooled by allowing to stand, and concentrated under reduced pressure. The obtained residue was dissolved in 30 ml of carbon disulfide. The obtained solution was dropwise added to 100 ml of a suspension of 7.2 g of aluminum chloride in carbon-disulfide. The obtained mixture was heated under reflux for 4 hours, cooled to room temperature by allowing to stand, and poured onto ice-water. The obtained mixture was extracted with 200 ml of ethyl acetate. The organic phase was washed with water, a saturated aqueous solution of sodium hydrogencarbonate and a saturated aqueous solution of common salt successively, dried over anhydrous magnesium sulfate, and concentrated under reduced pressure. The obtained residue was washed with isopropyl ether to give 5.0 g of the title compound.

m.p.; 88°–89° C. ¹H-NMR (400 MHz, CDCl₃) δ(ppm); 1.32(s, 6H), 1.93(t, J=9.0 Hz, 2H), 2.05–2.14 (m, 2H), 2.59(t, J=8.8 Hz, 2H), 2.85(t, J =9.0 Hz, 2H), 3.02(t, J=8.8 Hz, 2H), 7.22(s, 1H), 7.75(s, 1H)

REFERENTIAL EXAMPLE 4

3,5,6,7,8-Pentahydro-5,5,8,8-tetramethyl-4-oxo-1(2H)anthracenone

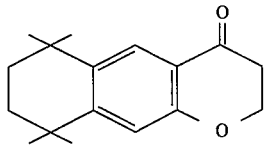

5,6,7,8-Tetrahydro-2-hydroxy-5,5,8,8-tetramethyl-3-N,N-dimethylaminoethynylcarbonylnaphthalene

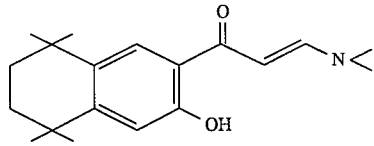

25 g of 3-acetyl-5,6,7,8-tetrahydro-2-hydroxy-5,5,8,8-tetramethylnaphthalene was dissolved in 100 ml of N,N-dimethylformamide, followed by the addition thereto of 27 ml of N,N-dimethylformamide dimethyl acetal. The obtained mixture was stirred under heating at 100° C. for 40 minutes, and cooled to room temperature by allowing to stand, followed by the addition thereto of 200 ml of ethyl acetate. The organic phase was washed with a saturated aqueous solution of common salt, dried over anhydrous magnesium sulfate, and distilled under reduced pressure to remove the solvent. The obtained residue was washed with n-hexane to give 13.4 g of the title compound as a yellow solid.

m.p.; 147°–149° C. ¹H-NMR (400 MHz, CDCl₃) δ(ppm); 1.26(s, 6H), 1.28(s, 6H), 1.67(s, 4H), 3.00(brs, 3H), 3.18(brs, 3H), 5.75(d, J=13.0 Hz, 1H), 6.85(s, 1H), 7.59(s, 1H), 7.86(d, J=13.0 Hz, 1H), 13.44(s, 1H)

5,6,7,8-Tetrahydro-5,5,8,8-tetramethyl-4-oxo-1(4H)anthracenone

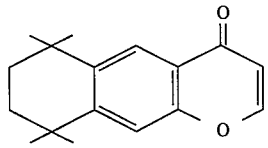

13.4 g of 5,6,7,8-tetrahydro-2-hydroxy-5,5,8,8-tetramethyl-3-N,N-dimethylaminoethynylcarbonylnaphthalene was added to dilute sulfuric acid (prepared from 30 ml of concentrated sulfuric acid and 200 ml of water) at room temperature. The obtained mixture was heated under reflux for 1.5 hours, cooled to room temperature by allowing to stand, and extracted with 200 ml of ethyl acetate. The organic phase was washed with water, a saturated aqueous solution of sodium hydrogencarbonate and a saturated aqueous solution of common salt successively, dried over anhydrous magnesium sulfate, and concentrated under reduced pressure. The obtained residue was washed with n-hexane to give 10 g of the title compound as a light-brown solid.

m.p.; 161°–163° C. ¹H-NMR (400 MHz, CDCl₃) δ(ppm); 1.32(s, 6H), 1.33(s, 6H), 1.73(s, 4H), 6.27(d, J=5.6 Hz, 1H), 7.36(s, 1H), 7.78(d, J=5.6 Hz, 1H), 8.12(s, 1H)

3,5,6,7,8-Pentahydro-5,5,8,8-tetramethyl-4-oxo-1(2H)anthracenone

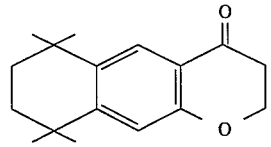

10 g of 5,6,7,8-tetrahydro-5,5,8,8-tetramethyl-4-oxo-1(4H)-anthracenone was dissolved in a mixture comprising 100 ml of ethanol and 100 ml of ethyl acetate, followed by the addition thereto of 1 g of 10% palladium/carbon. The obtained mixture was hydrogenated at room temperature under normal pressure for 1.5 hours. The reaction mixture was filtered to remove the catalyst. The filtrate was concentrated under reduced pressure and the obtained residue was purified by silica gel chromatography (developer: 5% ethyl acetate/n-hexane) to give 6.2 g of the title compound as a white solid.

m.p.; 100° C. ¹H-NMR (400 MHz, CDCl₃) δ(ppm); 1.26(s, 12H), 1.66(s, 4H), 2.77(t, J =6.4 Hz, 2H), 4.48(t, J=6.4 Hz, 2H), 6.89(s, 1H), 7.84(s, 1H)

REFERENTIAL EXAMPLE 5

3,4,5,6,7,8-Hexahydro-4,4,5,5,8,8-hexamethyl-1(2H)anthracenone

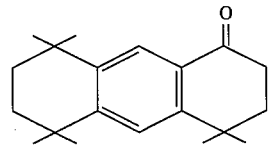

5-[2-(5,6,7,8-Tetrahydro-5,5,8,8-tetramethylnaphthyl)]-2-methyl-2-pentanol

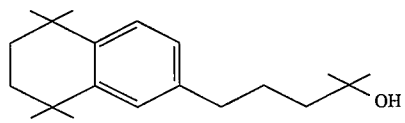

Under cooling with ice, 38 ml of a solution (3 mol/l) of methylmagnesium bromide in diethyl ether was dropwise added to 200 ml of a solution of 15 g of methyl 4-[2-(5,6,7,8-tetrahydro-5,5,8,8-tetramethylnaphthyl)]butyrate in anhydrous diethyl ether, and the obtained mixture was stirred for 10 minutes. The resulting mixture was further stirred at room temperature for 6 hours and cooled with ice. A saturated aqueous solution of ammonium chloride was carefully added to the reaction mixture to decompose excess reagent. The organic phase was washed with a saturated aqueous solution of sodium chloride, dried over anhydrous magnesium sulfate and distilled under reduced pressure to remove the solvent. 14 g of the title alcohol was obtained as a white solid.

m.p.; 75° C. $^1$H-NMR (400 MHz, CDCl$_3$) δ(ppm); 1.21(s, 6H), 1.26(s, 4H), 1.27(s, 6H), 1.48–1.56(m, 2H), 1.62–1.73(m, 3H), 1.65(s, 4H), 2.56(t, J=7.6 Hz, 2H), 6.96(dd, J=8.8 Hz, 2.5 Hz, 1H), 7.10(d, J=2.5 Hz, 1H), 7.20(d, J=8.8 Hz, 1H)

1,2,3,4,5,6,7,8-Octahydro-1,1,4,4,5,5-hexamethylanthracene

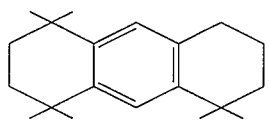

Under cooling with ice, 14 g of 5-[2-(5,6,7,8-tetrahydro-5,5,8,8-tetramethylnaphthyl)]-2-methyl-2-pentanol was added to 100 ml of a suspension of 10 g of aluminum chloride in nitromethane and the obtained mixture was stirred for 10 minutes. The resulting mixture was further stirred at room temperature for 3 hours and poured onto ice-water. The obtained mixture was extracted with 200 ml of ethyl acetate. The organic phase was washed with water, a saturated aqueous solution of sodium hydrogencarbonate and a saturated aqueous solution of common salt successively, dried over anhydrous magnesium sulfate, and distilled under reduced pressure to remove the solvent. 12 g of the title compound was obtained as a pale-yellow solid.

m.p.; 94°–95° C. $^1$H-NMR (400 MHz, CDCl$_3$) δ(ppm); 1.24(s, 6H), 1.25(s, 12H), 1.54–1.80(m, 4H), 1.64(s, 4H), 2.70(t, J=7.0 Hz, 2H), 6.93(s, 1H), 7.22(s, 1H)

3,4,5,6,7,8-Hexabydro-4,4,5,5,8,8-hexamethyl-1(2H)anthracenone

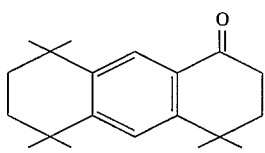

12 g of 1,2,3,4,5,6,7,8-octahydro-1,1,4,4,5,5-hexamethylanthracene was dissolved in a mixture comprising 80 ml of glacial acetic acid and 80 ml of acetone, followed by the addition thereto of 11 g of chromic anhydride under cooling with ice. The obtained mixture was stirred at room temperature for 10 hours and cooled with ice, followed by the addition thereto of an aqueous solution of sodium sulfite. The obtained mixture was stirred for 10 minutes. 300 ml of water was added to the resulting mixture to precipitate a solid. This solid was recovered by filtration and washed with water. 11 g of the title compound was obtained as a light-brown solid.

m.p.; 136°–138° C. $^1$H-NMR (400 MHz, CDCl$_3$) δ(ppm); 1.29(s, 12H), 1.36(s, 6H), 1.67(s, 4H), 1.97(t, J=7.0 Hz, 2H), 2.68(t, J=7.0 Hz, 2H), 7.32(s, 1H), 7.96(s, 1H)

REFERENTIAL EXAMPLE 6

3,4,5,6,7,8-Hexahydro-5,5-dimethyl-8-oxo-1(2H)anthracenone

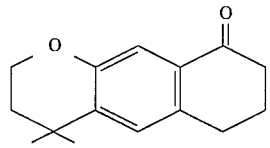

Ethyl γ-oxo-6-(4,4-dimethylchromanyl)]butyrate

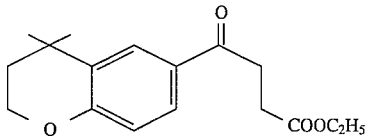

22 g of aluminum chloride and 22 g of monoethyl succinate chloride were added to 200 ml of a solution of 17.9 g of 4,4-dimethylchroman in methylene chloride at 0° C. The obtained mixture was stirred at room temperature for 24 hours and poured onto ice-water. The obtained mixture was extracted with ethyl acetate. The organic phase was washed with a saturated aqueous solution of common salt, dired over anhydrous magnesium sulfate, and distilled to remove the solvent. The obtained residue was purified by silica gel chromatography (developer: 304 ethyl acetate/n-hexane) to give 32 g of the title compound as a colorless oil.

$^1$H-NMR (400 MHz, CDCl$_3$) γ(ppm); 1.24(t, J=7.2 Hz, 3H), 1.35(s, 6H), 1.83–1.88(m, 2H), 3.24(t, J=7.2 Hz, 2H), 4.10–4.21(m, 2H), 4.22–4.28(m, 2H), 6.80(d, J=8.4 Hz, 1H), 7.71(dd, J=8.4 Hz, 2.4 Hz, 1H), 7.97(d, J=2.4 Hz, 1H)

γ-Oxo-6-(4,4-dimethylchromanyl)]propionic acid

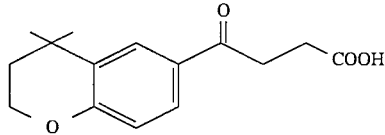

14 ml of a 5N aqueous solution of sodium hydroxide was added to 140 ml of a solution of 32 g of ethyl γ-oxo-6-(4,4-dimethylchromanyl)]butyrate in ethanol at room temperature. The obtained mixture was stirred at 50° C. for 5 hours, followed by the addition thereto of 100 ml of water and a 104 aqueous solution of hydrochloric acid. The obtained mixture was extracted with ethyl acetate. The organic phase was washed with a saturated aqueous solution of common salt, dried over anhydrous magnesium sulfate, and distilled to remove the solvent. The obtained solid (23 g) was used in the subsequent reaction without further purification.

m.p.; 110°–112° C. $^1$H-NMR (400 MHz, CDCl$_3$) δ(ppm); 1.28(s, 6H), 1.82–1.87(m, 2H), 2.77(t, J=7.2 Hz, 2H), 3.26(t, J=7.2 Hz, 2H), 4.23–4.28(m, 2H), 6.81(d, J=8.8 Hz, 1H), 7.71(dd, J=8.8 Hz, 2.4 Hz, 1H), 7.97(d, J=2.4 Hz, 1H)

4-[6-(4,4-Dimethylchromanyl)]butyric acid

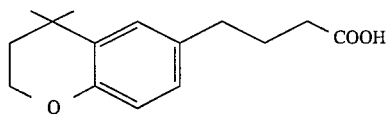

13.1 g of hydrazine monohydrate and 17 g of sodium hydroxide were added to 150 ml of a solution of 23 g of γ-oxo-6-(4,4-dimethylchromanyl)]butyric acid in diethylene glycol at room temperature. The obtained mixture was heated to 180° C., maintained at that temperature for 5 hours and poured into a 10% aqueous solution of hydrochloric acid. The obtained mixture was extracted with ethyl acetate. The organic phase was washed with a saturated aqueous solution of common salt, dried over anhydrous magnesium sulfate, and distilled to remove the solvent. The obtained residue was purified by silica gel chromatography (developer: 40% ethyl acetate/n-hexane) to give 19.5 g of the title compound as a pale-yellow oil.

$^1$H-NMR (400 MHz, CDCl$_3$) δ(ppm); 1.32(s, 6H), 1.84(t, J=7.2 Hz, 2H), 1.88–1.94(m, 2H), 2.38(t, J=7.2 Hz, 2H), 2.59(t, J=7.2 Hz, 2H), 6.70(d, J=8.8 Hz, 1H), 6.88(dd, J=8 Hz, 2.8 Hz, 1H), 7.04(d, J=2.8 Hz, 1H)

3,4,6,7,8,9-Hexahydro-5,5-dimethyl-8-oxo-1(2H)anthracenone

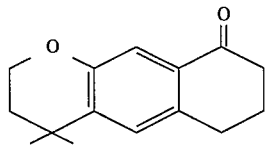

8.7 g of thionyl chloride was added to 80 ml of a solution of 9.2 g of 4-[6-(4,4-dimethylchromanyl)]butyric acid in 1,2-dimethoxyethane. The obtained mixture was heated under reflux for 2 hours and distilled to remove the solvent. The obtained residue was dissolved in 50 ml of carbon disulfide, followed by the addition of 0.35 g of aluminum chloride at 0° C. The obtained mixture was stirred at room temperature for one hour and poured onto ice-water. The obtained mixture was extracted with ethyl acetate. The organic phase was washed with a saturated aqueous solution of common salt, dried over anhydrous magnesium sulfate and distilled to remove the solvent. The obtained residue was purified by silica gel chromatography (developer: 10% ethyl acetate/n-hexane) to give 1.16 g of the title compound as a pale-yellow oil.

$^1$H-NMR (400 MHz, CDCl$_3$) δ(ppm); 1.32(s, 6H), 1.83(t, J=7.0 Hz, 2H), 2.06–2.14(m, 2H), 2.58(t, J=7.0 Hz, 2H), 2.86(t, J =7.0 Hz, 2H), 4.16(t, J=7.0 Hz, 2H), 7.12(s, 1H), 7.43(s, 1H)

REFERENTIAL EXAMPLE 7

7,8,9,10-Tetrahydro-7,7,10,10-tetramethylnaphtho[2,3-b]-5-oxo-cyclohepta-1-one

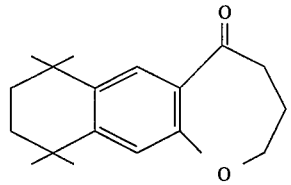

Ethyl 4-[2-(5,6,7,8-tetrahydro-5,5,8,8-tetramethyl-naphthoxy)]-2-butenoate

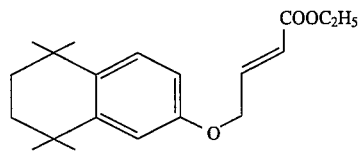

2.2 g of potassium carbonate and 2.4 g of ethyl 4-bromocrotonate were added to 30 ml of a solution of 2.2 g of 5,6,7,8-tetrahydro-5,5,8,8-tetramethyl-2-naphthol in N,N-dimethylformamide at room temperature. The obtained mixture was stirred at 50° C. for 6 hours, followed by the addition thereto of 20 ml of water. The obtained mixture was extracted with ethyl acetate. The organic phase was washed with a saturated aqueous solution of common salt, dried over anhydrous magnesium sulfate, and distilled to remove the solvent. The obtained residue was purified by silica gel chromatography (developer: 104 diethyl ether/n-hexane) to give 1.8 g of the title compound as a colorless oil.

$^1$H-NMR (400 MHz, CDCl$_3$) δ(ppm); 1.24(s, 6H), 1.26(s, 6H), 1.30(t, J=7.2 Hz, 3H), 1.56(s, 2H), 1.66(s, 2H), 4.00(d, J=6.0 Hz, 1H), 4.66(s, J=6.0 Hz, 2H), 6.22(dt, J=16 Hz, 1.4 Hz, 1H), 6.69(dd, J=8.8 Hz, 3.0 Hz, 1H), 6.84(d, J=3.0 Hz, 1H), 7.08(dr, J=16 Hz, 4 Hz, 1H), 7.22(d, J=8.8 Hz, 1H)

Ethyl 4-[2-(5,6,7,8-tetrahydro-5,5,8,8-tetramethyl-naphthoxy)]butyrate

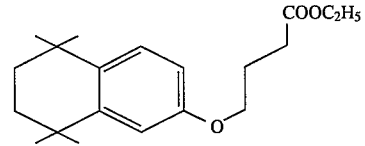

10.1 g of 10% palladium/carbon was added to 30 ml of a solution of 1.8 g of ethyl 4-[2-(5,6,7,8-tetrahydro-5,5,8,8-tetramethylnaphthoxy)]-2-butenoate in ethanol. The obtained mixture was stirred at room temperature under a hydrogen stream for 23 hours and filtered through Celite. The filtrate was distilled to remove the solvent. The obtained residue was purified by silica gel chromatography (developer: 10% diethyl ether/n-hexane) to give 1.04 g of the title compound as a colorless oil.

¹H-NMR (400 MHz, CDCl₃) δ(ppm); 1.22–1.29(m, 15H), 2.68(s, 4H), 2.08–2.16(m, 2H), 2.53(t, J=7.0 Hz, 2H), 3.99(t, J=7.0 Hz, 2H), 4.16(q, J=7.2 Hz, 2H), 6.71(dd, J=8.7 Hz, 3.0 Hz, 1H), 6.84(d, J=3.0 Hz, 1H), 7.24(d, J=8.7 Hz, 1H)

7,8,9,10-Hexahydro-7,7,10,10-tetramethylnaphtho-[2,3-b]-5-oxo-cyclohepta-1-one

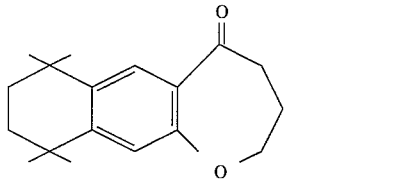

6 ml of a 5N aqueous solution of sodium hydroxide was added to 30 ml of a solution of 1.04 g of ethyl 4-[2-(5,6,7,8-tetrahydro-5,5,8,8-tetramethylnaphthoxy)]-butyrate in ethanol at room temperature. The obtained mixture was stirred at that temperature for 19 hours, followed by the addition thereto of 15 ml of water and a 10% aqueous solution of hydrochloric acid. The obtained mixture was extracted with ethyl acetate. The organic of common salt, dried over anhydrous magnesium sulfate and distilled to remove the solvent. The obtained residue (0.63 g) was dissolved in 30 ml of dimethoxyethane, followed by the addition thereto of 0.38 g of thionyl chloride at room temperature. The obtained mixture was heated under reflux for 4 hours and distilled to remove the solvent. The obtained residue was dissolved in 10 ml of carbon disulfide, followed by the addition thereto of 0.35 g of aluminum chloride at 0° C. The obtained mixture was stirred at room temperature for 2 hours and poured onto ice-water. The obtained mixture was extracted with ethyl acetate. The organic phase was washed with a saturated aqueous solution of common salt, dried over anhydrous magnesium sulfate and distilled to remove the solvent. The obtained solid residue was washed with methanol to give 0.10 g of the title compound as a pale-yellow solid.

m.p.; 124°–125° C. ¹H-NMR (400 MHz, CDCl₃) δ(ppm); 1.26(s, 12H), 1.66(s, 4H), 2.12–2.23(m, 2H), 2.86(t, J=7.0 Hz, 2H), 4.20(t, J=7.0 Hz, 2H), 6.98(s, 1H), 7.74(s, 1H)

REFERENTIAL EXAMPLE 8

7-Isopropoxy-6-isopropyl-1-tetralone

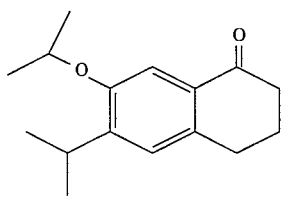

7-Hydroxy-6-isopropyl-1-tetralone

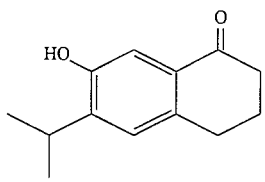

20 ml of ethanethiol was added to 100 ml of a suspension of 28 g of aluminium chloride in dichloromethane cooled with ice. The obtained mixture was stirred for 5 minutes, followed by the slowly, dropwise addition thereto of 50 ml of a solution of 15.3 g of 6-isopropyl-7-methoxy-1-tetralone in dichloromethane. After the completion of the dropwise addition, the obtained mixture was stirred for 3 hours at room temperature and poured onto ice-water. The obtained mixture was extracted with ethyl acetate. The organic phase was washed with water, a saturated aqueous solution of sodium hydrogencarbonate and a saturated aqueous solution of common salt successively, dried over anhydrous magnesium sulfate, and distilled to remove the solvent. The obtained solid residue was washed with n-hexane to give 8.5 g of the title compound as a white solid.

m.p.; 149°–150° C. ¹H-NMR (400 MHz, CDCl₃) δ(ppm); 1.25(d, J=6.5 Hz, 6H), 2.06–2.15(m, 2H), 2.63(t, J=7.0 Hz, 2H), 2.88(t, J=7.0 Hz, 2H), 3.29–3.38(m, 1H), 6.42(s, 1H), 7.05(s, 1H), 7.63(s, 1H)

7-Isopropoxy-6-isopropyl-1-tetralone

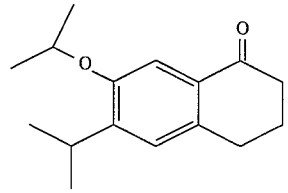

5.4 g of 7-Hydroxy-6-isopropyl-1-tetralone was dissolved in 50 ml of N,N-dimethylformamide, followed by the addition of 7.3 g of potassium carbonate and 4.3 ml of 2-bromopropane. The obtained mixture was stirred for 8 hours under heating, cooled to room temperature by allowing to stand and extracted with ethyl acetate. The organic phase was washed with a saturated aqueous solution of common salt, dried over anhydrous magnesium sulfate, and concentrated under reduced pressure. The obtained residue was purified by silica gel chromatography (developer: 5% ethyl acetate/n-hexane) to give 6.0 g of the title compound as a yellow oil.

¹H-NMR (400 MHz, CDCl₃) δ(ppm); 1.21(d, J=6.5 Hz, 6H), 1.33(d, J=6.5 Hz, 6H), 2.06–2.14(m, 2H), 2.60(t, J=7.0 Hz, 2H), 2.88(t, J=7.0 Hz, 2H), 3.28–3.38(m, 1H), 4.62–4.70(m, 1H), 7.03(s, 1H), 7.45(s, 1H)

REFERENTIAL EXAMPLE 9

7-(2,5-Dimethylpyrrolo-1-yl)-1-tetralone

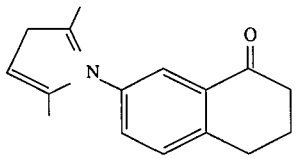

3.3 g of 7-Amino-1-tetralone and 7.0 g of 2,5-hexadione were dissolved in 30 ml of glacial acetic acid. The obtained solution was heated under reflux for 30 minutes, cooled to room temperature by allowing to stand, poured onto a saturated aqueous solution of sodium hydrogencarbonate and extracted with ethyl acetate. The organic phase was washed with a saturated aqueous solution of common salt, dried over anhydrous magnesium sulfate, and concentrated under reduced pressure. The obtained residue was purified by silica gel chromatography (developer: 5% ethyl acetate/n-hexane) to give 4.3 g of the title compound as a yellow solid.

m.p.; 119°–120° C. $^1$H-NMR (400 MHz, CDCl$_3$) δ(ppm); 2.03(s, 6H), 2.16–2.24(m, 2H), 2.70(t, J=7.0 Hz, 2H), 3.04(t, J=7.0 Hz, 2H), 5.89(s, 2H), 7.03(dd, J=8.9 Hz, 2.5 Hz, 1H), 7.36(d, J=8.9 Hz, 1H), 7.88(d, J=2.5 Hz, 1H)

REFERENTIAL EXAMPLE 10

6,8-Diisopropyl-1-tetralone

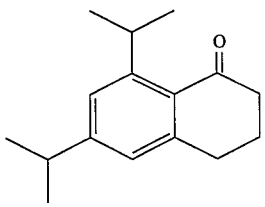

Methyl 3-[3,5-Diisopropyl-4-(1-phenyltetrazol-5-yloxy)benzoyl]propionate

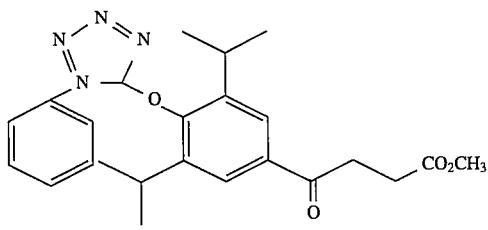

11 g of Methyl 3-(4-hydroxy-3,5-diisopropylbenzoyl)propionate was dissolved in 200 ml of N,N-dimethylformamide, followed by the addition of 8.15 g of 5-chloro-1-phenyl-1H-tetrazol and 10.4 g of potassium carbonate. The obtained mixture was stirred for 1 hour under heating, cooled to room temperature by allowing to stand and poured onto ice-water. The resultant mixture was extracted with ethyl acetate. The organic phase was washed with a saturated aqueous solution of common salt, dried over anhydrous magnesium sulfate, and distilled under reduced pressure to remove the solvent. The obtained residue was purified by silica gel chromatography (developer: 20% ethyl acetate/n-hexane) to give 14.1 g of the title compound as a white solid.

m.p.; 122°–123° C. $^1$H-NMR (400 MHz, CDCl$_3$) δ(ppm); 1.21(d, J=6.5 Hz, 12H), 2.78(t, J=7.0 Hz, 2H), 2.90–3.00(m, 2H), 3.35(t, J=7.0 Hz, 2H), 3.72(s, 3H), 7.52–7.67(m, 3H), 7.83(m, 4H)

Methyl 3-(3,5-diisopropylbenzoyl)propionate

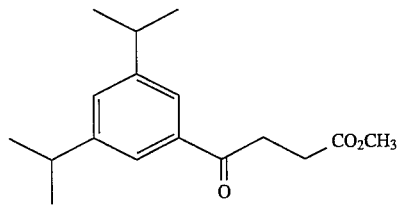

14.1 g of Methyl 3-[3,5-diisopropyl-4-(1-phenyltetrazol-5-yloxy)benzoyl]propionate was dissolved in 100 ml of benzene, followed by the addition of 10 g of 10% palladium/carbon. The obtained mixture was subjected to hydrogenation under a pressure of 3 kg/cm$^2$, at room temperature for 14 hours. The reaction mixture thus obtained was filtered to remove the catalyst. The filtrate was concentrated under reduced pressure. The obtained residue was purified by silica gel chromatography (developer: 3% ethyl acetate/n-hexane) to give 6.4 g of the title compound as a colorless oil.

$^1$H-NMR (400 MHz, CDCl$_3$) δ(ppm); 1.26(d, J=6.5 Hz, 12H), 2.76(t, J=7.0 Hz, 2H), 2.88–3.00(m, 2H), 3.32(t, J=7.0 Hz, 2H), 3.71(s, 3H), 7.28(d, J=2.4 Hz, 1H), 7.65(d, J=2.4 Hz, 2H)

6,8-Diisopropyl-1-tetralone

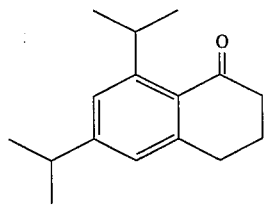

4.8 g of The title compound as a brown oil was prepared from 6.4 g of methyl 3-(3,5-diisopropylbenzoyl)propionate in the same manner as that of the Referential Example 2.

$^1$H-NMR (400 MHz, CDCl$_3$) δ(ppm); 1.22(d, J=6.5 Hz, 6H), 1.26(d, J=6.5 Hz, 6H), 2.02–2.09(m, 2H), 2.63(t, J=7.0 Hz, 2H), 4.10–4.20(m, 1H), 6.93(s, 1H), 7.17(s, 1H)

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A compound represented by the following formula (I) or a physiologically acceptable salt thereof:

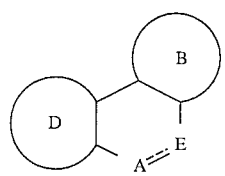
(I)

wherein
the ring D represents a group represented by the following formula:

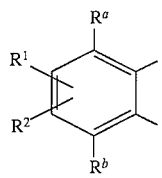

where $R^1$ and $R^2$ are the same or different and each represents a hydrogen atom, a $C_{1-6}$ alkyl group, a $C_{1-4}$ alkoxy group, a cycloalkyloxy group, a cycloalkyloxy group substituted with a cyclopropyloxy group, a cyclobutyloxy group, a cyclopentyloxy group, a cyclohexyloxy group or a cycloheptloxy group, a halogen atom, an aryl group, an aryl group substituted with a lower alkyl group, a halogen atom or a lower alkoxy group, an aryloxy group, an aryloxy group substituted with a lower alkyl group, a halogen atom or a lower alkoxy group or a heteroaryl group, or alternatively $R^1$ and $R^2$ together form a 5- to 7-membered cycloalkyl ring which is substituted with one or more $C_{1-6}$ alkyl groups or a 5- to 7-membered saturated heterocycle containing as the hetero atom S, O, SO, $SO_2$ or $NR^3$ where $R^3$ represents a hydrogen atom or a lower alkyl group, wherein the heterocycle may be substituted with one or more $C_{1-6}$ alkyl groups; and $R^a$ and $R^b$ are the same or different and each represents a hydrogen atom, a $C_{1-6}$ alkyl group or a $C_{1-4}$ alkoxy group;
A represents O, S, $SO_2$, $NR^3$ where $R^3$ is as described above, or $CR^4R^5$ where $R^4$ and $R^5$ are the same or different and each represents a hydrogen atom or a $C_{1-6}$ alkyl group;
E represents $(CH_2)_n$ wherein n is 0, 1 or 2, $CHCH_3$ or $C(CH_3)_2$;
the symbol ---- represents a single or double bond; and
the ring B represents a group represented by one of the following formulae:

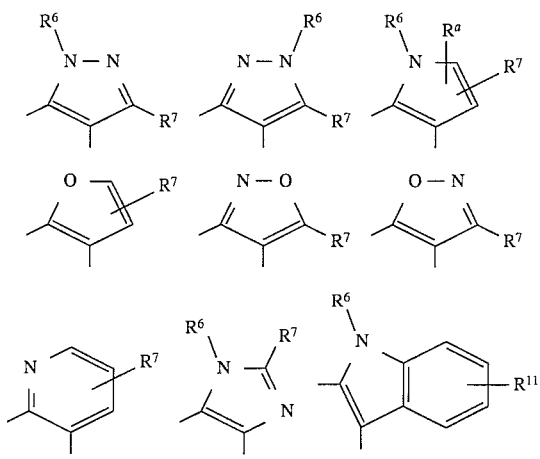

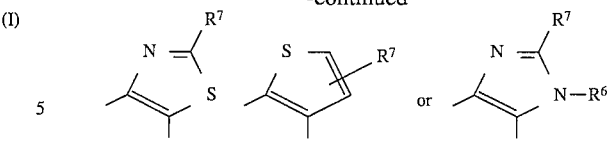

where $R^6$ represents a hydrogen atom, a $C_{1-6}$ alkyl group, an alkenylalkyl group, an alkynylalkyl group, a bridged cyclic hydrocarbon group, a cycloalkyl group, a cycloalkylalkyl group, a $C_{1-6}$ alkoxyalkyl group, an aryl group, a heteroaryl group, an arylalkyl group or a heteroarylalkyl group; $R^7$ represents a group represented by the following formula:

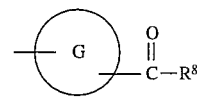

where the ring G represents a phenylene group or a 5- or 6-membered heterocyclic group having one or two hetero atoms; and $R^8$ represents a hydrogen atom, a hydroxyl group, a $C_{1-4}$ alkoxy group, a morpholylalkyloxy group or a group represented by the formula: $-NR^9R^{10}$ where $R^9$ and $R^{10}$ are the same or different and each represents a hydrogen atom, a hydroxyl group, a $C_{1-6}$ alkyl group, a $C_{1-4}$ alkoxy group, a hydroxyalkyl group, an aryl group or a hetroaryl group, or alternatively $R^9$ and $R^{10}$ may form a ring, which may contain a nitrogen atom, an oxygen atom or a sulfur atom, together with the nitrogen atom to which $R^9$ and $R^{10}$ are bonded, $R^a$ is as defined above and $R^{11}$ represents a group represented by the formula: $-COR^8$ where $R^8$ is as defined above.

2. The compound or the physiologically acceptable salt thereof according to claim 1, wherein the compound is represented by the following formula:

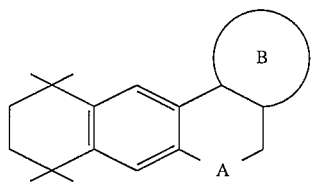

wherein A and the ring B are each as defined above.

3. The compound or the physiologically acceptable salt thereof according to claim 1, wherein the compound is represented by the following formula:

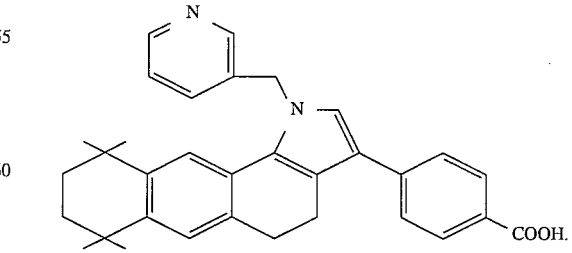

4. The compound or the physiologically acceptable salt thereof according to claim 1, wherein the compound is represented by the following formula:

5. The compound or the physiologically acceptable salt thereof according to claim 1, wherein the compound is represented by the following formula:

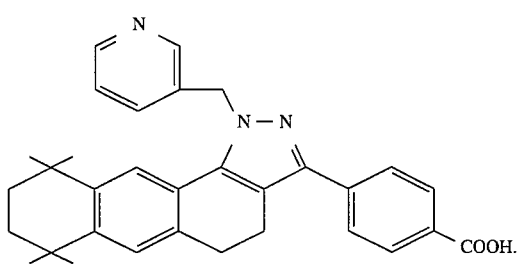

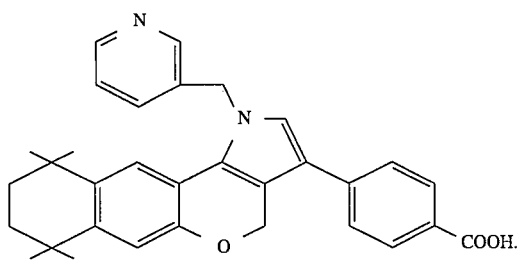

6. The compound or the physiologically acceptable salt thereof according to claim 1, wherein the compound is represented by the following formula:

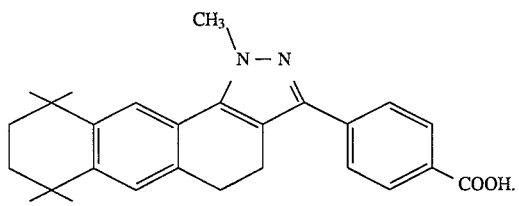

7. A pharmaceutical composition comprising a compound of claim 1 and a pharmaceutically acceptable carrier or diluent.

* * * * *